United States Patent [19]
Underiner et al.

[11] Patent Number: 5,866,576
[45] Date of Patent: Feb. 2, 1999

[54] EPOXIDE-CONTAINING COMPOUNDS

[75] Inventors: Gail Underiner, Brier; J. Peter Klein, Vashon; John Michnick, Seattle; Alistair Leigh, Brier; Anil Kumar, Seattle, all of Wash.

[73] Assignee: Cell Therapeutics, Inc., Seattle, Wash.

[21] Appl. No.: 778,563

[22] Filed: Jan. 3, 1997

Related U.S. Application Data

[63] Continuation of Ser. No. 167,600, Dec. 13, 1993, abandoned, which is a continuation-in-part of Ser. No. 991,655, Dec. 16, 1992, abandoned.

[51] Int. Cl.⁶ .................... A61K 31/505; C07D 239/02
[52] U.S. Cl. .................... 514/256; 514/396; 514/263; 544/242; 548/300.1; 548/311.1
[58] Field of Search .................... 544/269, 266, 544/267, 268, 270, 272, 273, 271, 242; 514/263, 256; 548/300.1, 311.1

[56] References Cited

U.S. PATENT DOCUMENTS

| | | | |
|---|---|---|---|
| 3,422,107 | 1/1969 | Mohler et al. | 514/263 |
| 3,737,433 | 6/1973 | Mohler et al. | 544/271 |
| 4,515,795 | 5/1985 | Hinze et al. | 514/263 |
| 4,576,947 | 3/1986 | Hinze et al. | 514/263 |
| 4,636,507 | 1/1987 | Kreutzer et al. | 514/263 |
| 4,833,146 | 5/1989 | Gebert et al. | 514/263 |
| 4,965,271 | 10/1990 | Mandell et al. | 514/263 |
| 5,039,666 | 8/1991 | Novick et al. | 517/37 |
| 5,096,906 | 3/1992 | Mandell et al. | 514/263 |
| 5,158,967 | 10/1992 | Hall | 514/374 |
| B1 3,737,433 | 3/1987 | Mohler et al. | 544/271 |

OTHER PUBLICATIONS

Akhmedov et al., *Chemical Abstract*, No. 99:158152e, "Study of the Reaction of Unsaturated Chlorine–Containing Epoxy Compounds with Secondary Amines," 1982.

Bianco et al., *Blood*, 76: Supplement 1 (522), p. 133a, "Pentoxifylline (PTX) and GM–CSF Decrease Tumor Necrosis Factor–Alpha (TNF–α) Levels in Patients Undergoing Allogeneic Bone Marrow Transplantation (BMT)", 1991.

Davis et al., *Applied Environment Microbial.*, 48:2, pp. 327–331, "Microbial Models of Mammalian Metabolism: Microbial Reduction and Oxidation of Pentoxifylline", Aug. 1984.

Jakubowski et al., *J. Org. Chem.*, 47, pp. 1221–1228, Total Syntheses of (±)–Cerulenin, (±)–Tetrahydrocerulenin, and Related Compounds, 1982.

*Primary Examiner*—Mukund J. Shah
*Assistant Examiner*—Pavanaram K Sripada
*Attorney, Agent, or Firm*—McDermott Will & Emery

[57] ABSTRACT

Disclosed are enantiomers, diastereomers, salts, solvates, hydrates and mixtures thereof, of formula I:

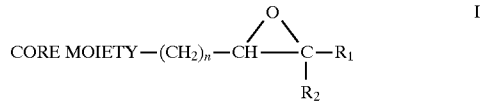

The core moiety is a monocyclic ring structure having five to six ring atoms and two nitrogen atoms at the 1 and 3 positions, n is an integer from 4 to 16, $R_1$ and $R_2$ are hydrogen, halogen or $C_{1-12}$ alkyl or alkenyl, and $(CH_2)_n$ may be optionally substituted by a hydroxyl, halogen, oxygen, a $C_{1-4}$ alkyl group or a dimethylamino group. The compounds and pharmaceutical composition thereof are useful in methods for treating an individual having a disease or treatment-induced toxicity mediated through a second messenger.

9 Claims, 28 Drawing Sheets

EPOXIDE-CONTAINING COMPOUNDS

CROSS-REFERENCE TO RELATED APPLICATION

This is a continuation application of Ser. No. 08/167,600 filed Dec. 13, 1993 now abandoned, which in turn is a continuation-in-part application of Ser. No. 07/991,655 filed Nov. 16, 1992 now abandoned.

TECHNICAL FIELD OF THE INVENTION

The invention relates to a class of epoxide-containing therapeutic compounds that act as drugs on the cellular and biochemical level to modulate cellular responses to noxious, pro-inflammatory stimuli. More specifically, the inventive compounds have at least one epoxide group on a side chain bonded to a core moiety.

BACKGROUND OF THE INVENTION

Pentoxifylline (1-(5-oxohexyl)-3,7-dimethylxanthine), abbreviated PTX, is a xanthine derivative which has seen widespread medical use for the increase of blood flow. PTX is disclosed in U.S. Pat. Nos. 3,422,107 and 3,737,433. Metabolites of PTX were summarized in Davis et al., *Applied Environment Microbiol.* 48:327, 1984. A metabolite of PTX is 1-(5-hydroxyhexyl)-3,7-dimethylxanthine, designated M1. M1 was also disclosed as increasing cerebral blood flow in U.S. Pat. Nos. 4,515,795 and 4,576,947. In addition, U.S. Pat. Nos. 4,833,146 and 5,039,666 disclose use of tertiary alcohol analogs of xanthine for enhancing cerebral blood flow.

Furthermore, U.S. Pat. No. 4,636,507 describes an ability of PTX and M1, to stimulate chemotaxis in polymorphonuclear leukocytes in response to a stimulator of chemotaxis. PTX and related tertiary alcohol substituted xanthines inhibit activity of certain cytokines to affect chemotaxis (U.S. Pat. No. 4,965,271 and U.S. Pat. No. 5,096,906). Administration of PTX and GM-CSF decrease tumor necrosis factor (TNF) levels in patients undergoing allogeneic bone marrow transplant (Bianco et al., *Blood* 76: Supplement 1 (522A), 1990). Reduction in assayable levels of TNF was accompanied by reduction in bone marrow transplant-related complications. However, in normal volunteers, TNF levels were higher among PTX recipients. Therefore, elevated levels of TNF are not the primary cause of such complications.

Therefore, there is a need in the art to discover effective therapeutic compounds that are safe and effective for human or animal administration and that maintain cellular homeostasis in the face of a variety of inflammatory or noxious stimuli. The invention results from investigations of such compounds.

SUMMARY OF THE INVENTION

We have found that the compounds described herein can be used to maintain homeostasis of a large variety of target cells in response to a variety of stimuli. In addition, the inventive compounds and compositions are suitable for normal routes of therapeutic administration and permit effective dosages to be provided.

The invention is directed to epoxide-containing alkyl side chains bonded to a core moiety useful in modulating cellular response to external or in situ primary stimuli, as well as to specific modes of administration of such compounds in effective amounts.

The inventive epoxide-containing compounds include enantiomers and/or diastereomers, salts, solvates, hydrates and mixtures thereof, the inventive compounds having the following formula I:

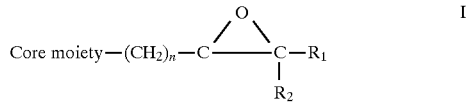

wherein n is an integer from about 4 to about 16, $R_1$ and $R_2$ are hydrogen, halogen or $C_{1-12}$ alkyl or alkenyl and the core moiety has a non-cyclic structure or is at least one five- to seven-membered cyclic structure. Preferably, n is an integer from about 4 to about 12, more preferably from about 4 to about 10. $(CH_2)_n$ may be substituted by a hydroxyl, halogen, oxygen, a $(C_{1-4})$ alkyl group or a dimethylamino group. The alkyl or alkenyl groups may also be substituted by a hydroxy, halo or dimethylamino group and/or interrupted by an oxygen atom, or $C_{1-4}$ alkyl. Exemplary halogens include bromine, chlorine, fluorine and iodine.

A non-cyclic core moiety may be, for example, acetamide, amide, amine, amino acid (one or two), carboxyl, ester, halogen atom, terminal hydrogen atom, hydroxyl, glutaric acid, glycine derivative, ketone, phosphate, phosphonate, sulfate, sulfonate, sulfone, sulfoxide, simple ionic functional group, thiol or thiolester. Exemplary core moiety amino acids may include one or more of the following: alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine and valine. The non-cyclic core moiety may preferably be a dipeptide comprising two amino acids selected from the foregoing exemplary list. Exemplary core halogen atoms include bromine, chlorine, fluorine and iodine.

A core moiety may have from one to three, five- to six-membered ring structures in a predominantly planar configuration. Preferably, an epoxide-containing functional group is bonded to a ring nitrogen if one exists. For example, the core moiety may be selected from the group consisting of substituted or unsubstituted barbituric acid; benzamide; benzene; biphenyl; cyclohexane; cyclohexanedione; cyclopentanedione; lactam; glutarimide; homophthalimide; hydrophthalimide; imidazole; imidazole amide; indomethacin; isocarbostyril; lumazine; napthlalene; phenol; pteridine; pthalimide; piperidine; pyridine; pyrimidine; pyrrole amide; quinolizinedione; quinazolinone; quinolone; recorsinol; salicylic acid and derivatives thereof; stilbene; succinimide; theobromine; thymine; triazine; tricyclododecane; uric acid; uracil; vitamins A, E or K; or xanthine.

Preferred cyclic cores include substituted or unsubstituted glutarimide, methylthymine, methyluracil, thymine, theobromine, uracil and xanthine, most preferably halogen-substituted xanthine. Exemplary preferred cores include: N-methylbenzamide, 1,3-cyclohexanedione, 1,3-cyclopentanedione; 1,3-dihydroxynaphthalene; 1-methyllumazine; methylbarbituric acid; 3,3-dimethylglutarimide; orotic acid; orthophenol; tetra or hexahydrophthalimide; 2-piperidone; prostacyclin; 2-hydroxypyridine; methyldihydroxypyrazolopyrimidine, specifically, 1,3-dimethyldihydroxypyrazolo[4,3-d] pyrimidine; methylpyrrolopyrimidine; 1-methylpyrrolo [2,3-d] pyrimidine; 1,3-dihydroxynapthalene; 1-pyrrole amides; 2-pyrrole amides; 3-pyrrole amides; 1,2,3,4-tetrahydroisoquinolone; 1-methyl-2,4(1H,3H)-quinolizinedione (1-methylbenzoyleneurea); quinazolin-4 (3H)-one; sulindac; dihydrothymine; alkyl-substituted (C1–6) thymine; 2,4-dioxohexahydro-1,3,5tetrazine; methylthymine; alkyl-substituted (C1–6) uracil; uracil fused to naphthalene; 6-aminouracil; 1-methyldihydrouracil; 1-methyluracil; 5- and/or 6-position substituted uracils (such as, for example, 5-bromouracil); B-ionone as vitamin A; 2,6,6-trimethyl-1-cyclohexene-1-acetaldehyde as vitamin A; tetralone to vitamin K; 1,7-dimethylxanthine, 3,7-dimethylxanthine; 3-methylxanthine; 3-methyl-7-methylpivaloylxanthine; 8-substituted xanthines (having substituents such as nitrogen or sulfur); and 7-methylhypoxanthine.

Preferably, an epoxide-containing group is bonded to a nitrogen of the core moiety, most preferably, the core moiety is xanthine and the epoxide-containing group is bonded to an $N_1$ xanthine nitrogen and $N_3$ and $N_7$ xanthine nitrogens are independently substituted by a member selected from the group consisting of hydrogen, methyl, fluoro, chloro and amino.

The invention includes a method for modulating an immune response or a cellular response to external or in situ primary stimuli comprising administering an effective amount of an inventive compound. Particularly, on a cellular or biochemical level, the inventive compounds have been found to inhibit a specific phospholipid-based pathway that amplifies a signal within a cell. This pathway tends to be activated in response to noxious or inflammatory stimuli. The inventive compounds also decrease proliferation of tumor cells in response to an activated oncogene; stimulate hematopoiesis in the presence of agents which inhibit hematopoiesis, such as chemotherapeutic agents; suppress the activation of T-cells in the presence of antigen and the secretion of antibodies by B-cells in the presence of antigen; suppress the activation of macrophage or endothelial cells by endotoxins, tumor necrosis factor (TNF), interleukin-1 (IL-1) or granulocyte macrophage colony stimulating factor (GM-CSF); enhance the resistance of mesenchymal cells to TNF; inhibit the proliferation of smooth muscle cells, endothelial cells, fibroblasts and other cell types in response to growth factors, such as platelet derived growth factor (PDGF), PDGF-AA, PDGF-BB, fibroblast growth factor (FGF), epidermal growth factor (EGF), etc.; inhibit the activation of T-cells and viral replication in response to human immunodeficiency virus; inhibit the proliferation of kidney mesangial cells in response to IL-1; prevent suppression of Steel factor (also called stem cell factor, mast cell growth factor and kit ligand), granulocyte colony stimulating factor (G-CSF), oncostatin M or interleukin-6 (IL-6) in bone marrow stromal cells in response to TNF; suppress expression of adhesion molecules in endothelial cells and suppress adhesion of inflammation cells to endothelial cells; suppress proliferation of kidney mesangial cells in response to IL-1, mip-1α, PDGF or FGF; prevent toxicity in kidney glomerular or tubular cells in response to cyclosporin A or amphotericin B; prevent cytotoxic effects in gastrointestinal or pulmonary epithelial cells in response to a cytotoxic drug or radiation; enhance the antitumor effects in tumor cells in response to a nonalkylating antitumor agent; suppress the production of metalloproteases in synovial cells, other fibroblasts and a glomerular epithelial cell in response to inflammatory stimuli, such as TNF, IL-1 and the like; inhibit production of osteoclast-activating factor (OAP) by osteoclasts in response to IL-1; inhibit degranulation of mast cells and basophils in response to IgE; modulate signal transduction of the neurotransmitters epinephrine and acetylcholine in neural pathways utilizing these transmitters, block activation of platelet activating factor in inflammation cells, block release of TNF and IL-1 in various cell types in response to inflammatory stimuli, block activation and proliferation of lymphocytes and other cell types to IL-1 and interleukin-2 (IL-2), and the like, including the clinical manifestations of these cellular and biochemical events.

In vitro, the inventive compounds: 1) block IL-1 signal transduction through the Type 1 receptor as shown, for example, by preventing IL-1 and IL-1 plus PDGF (platelet derived growth factor) induction of proliferation of smooth muscle and kidney mesengial cells; 2) suppress regulation of adhesion molecules as shown, for example, by blocking VCAM in endothelial cells of CD18 in neutrophils; 3) inhibit TNF, LPS and IL-1 induced metalloproteases (an inflammation model); 4) block LPS, TNF or IL-1 induced cellular activation (for prevention and treatment of septic shock); 5) suppress T cell and B cell antigen activation by cross-linking CD3 complex; 6) inhibit mast cell activation by IgE; and 7) suppress malignant phenotype in transformed cells and tumor cell lines.

The inventive compounds, inter alia, inhibit signal transduction mediated through the Type I IL-1 receptor, and are therefore considered as IL-1 antagonists. Dinarello and Wolff, "The Role of Interleukin-1 in Disease," *N. Engl. J. Med.* 328, 106 (Jan. 14, 1993), describe the role of IL-1 as "an important rapid and direct determinant of disease. In septic shock, for example, IL-1 acts directly on the blood vessels to induce vasodilatation through the rapid production of platelet activating factor and nitric oxide, whereas in autoimmune disease it acts by stimulating other cells to produce cytokines or enzymes that then act on the target tissue." Ibid. The article describes a group of diseases mediated by IL-1, including many of the foregoing diseases.

In still another aspect, the invention is directed to a pharmaceutical composition comprising an inventive compound and an effective amount of an agent which reduces the activity of the enzyme P-450, such as a quinolone, to increase the pharmacokinetic half-life of an inventive compound.

BRIEF DESCRIPTION OF THE DRAWINGS

As shown in FIG. 2, both drugs inhibited thymocyte proliferation is a dose-dependent fashion.

Figure 5:
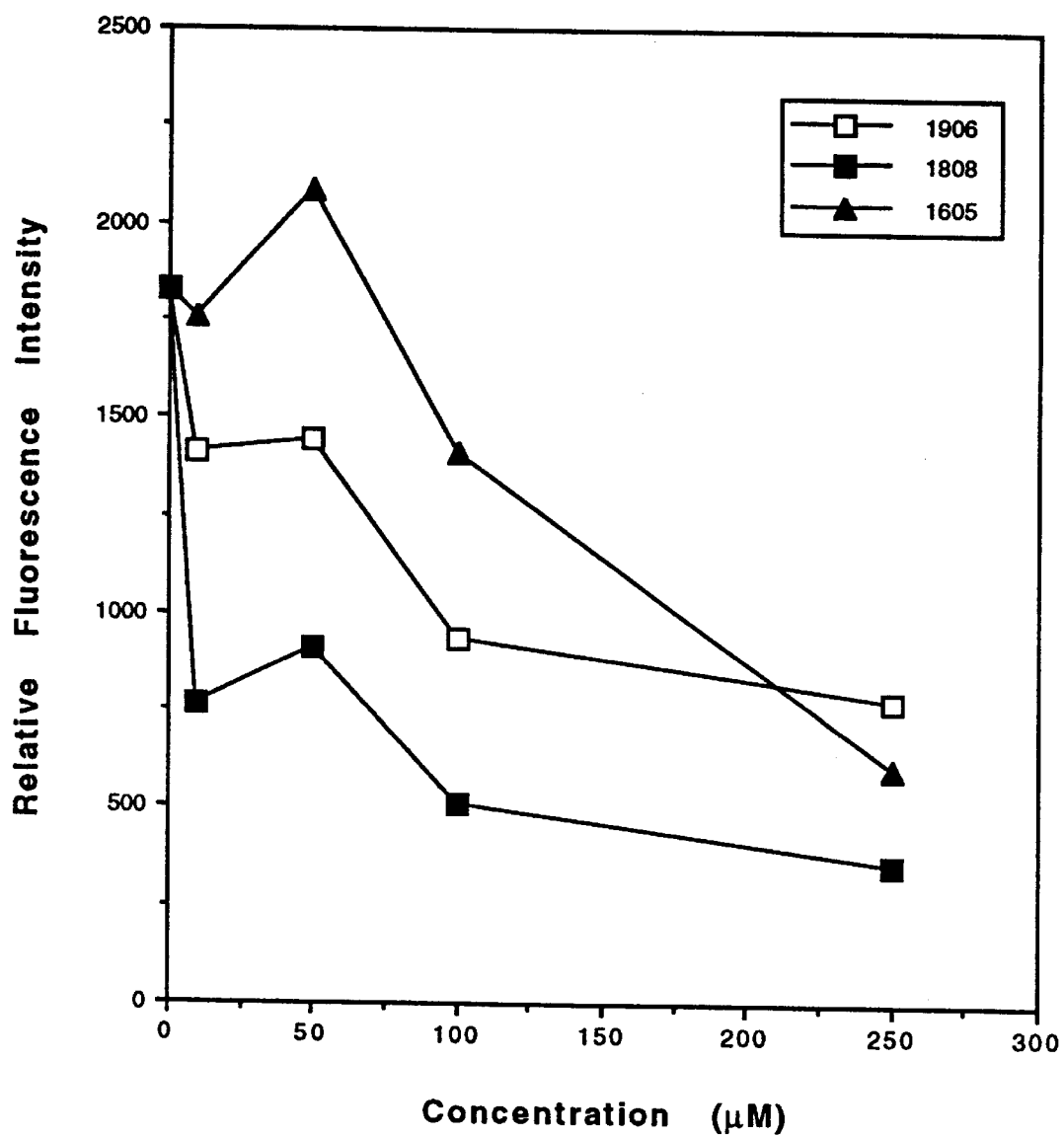

FIG. 5 shows the effect of 1605, 1808 and 1906 to inhibit adhesion of U937 cells to activated human umbilical vein endothelial cells (HUVEC). HUVEC cells were activated with 20 ng/ml of TNF for 12 hrs. Drug was added to each culture (except for controls) one hour prior to adding TNF. U937 cells, preloaded with the fluorescent dye BCECF, were added to each culture well and then washed. Cell adhesion was determined on a fluorescence plate reader, showing a decrease in cell adhesion caused by all three drugs in a dose dependent fashion.

Figure 6:
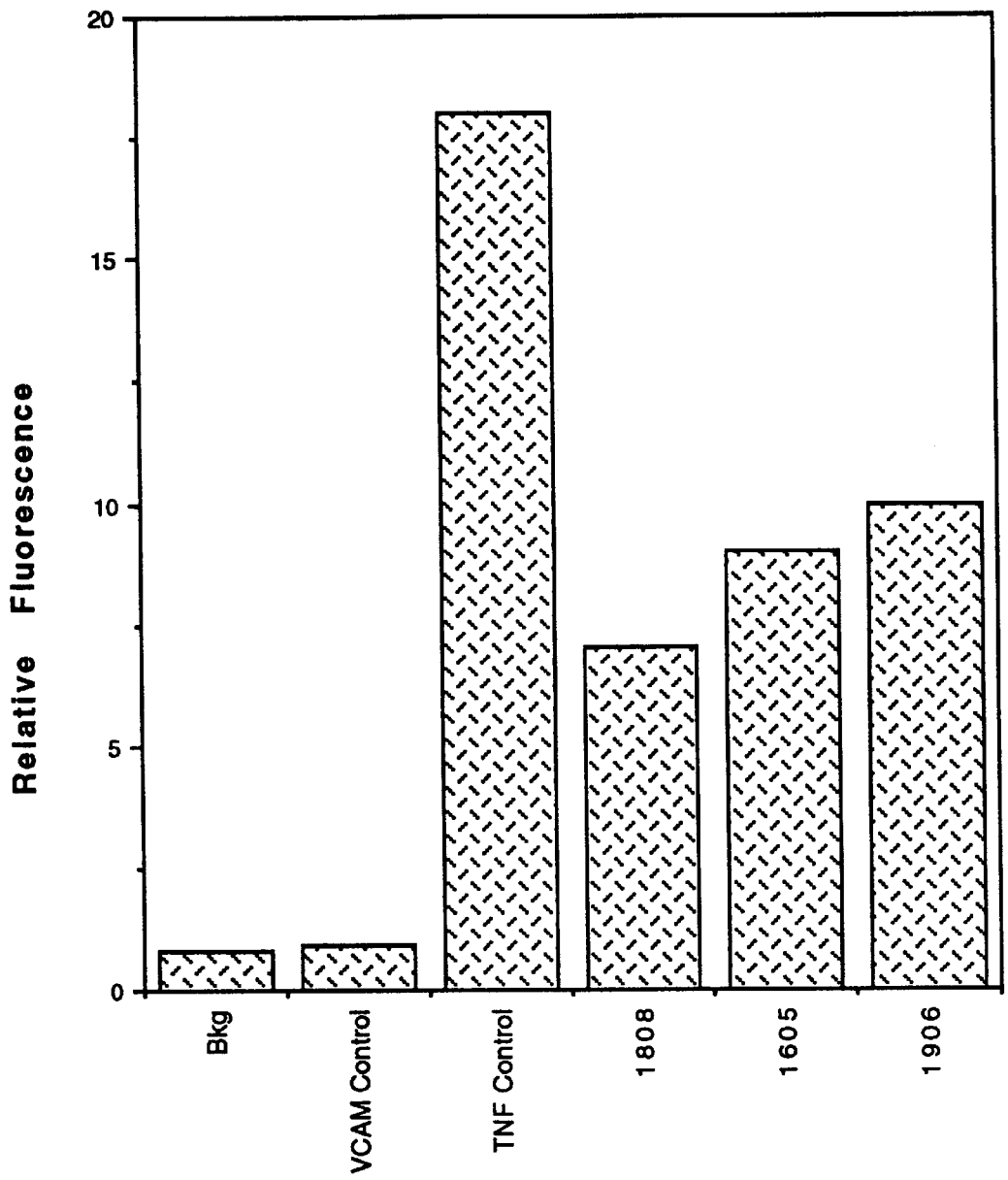

FIG. 6 shows the effects of 1605, 1808 and 1906 to inhibit cell surface expression of VCAM in human umbilical vein endothelial cells (HUVEC). The HUVEC cells were stimulated with 20 ng/ml TNF-α for 20 hrs and then stained for immunofluorescence using a monoclonal antibody recognizing VCAM, followed by a goat anti-mouse antibody conjugated to phycoerythrin. The cells were analyzed for antibody binding using flow cytometry. FIG. 6 shows an analysis of mean relative fluorescence intensity of 10,000 cells, analyzed by flow cytometry. The mean fluorescence levels were decreased by all three drugs from control levels (TNF treatment, no drug).

FIGS. 7A, 7B, 7C, 7D and 7E illustrates dose response curves obtained in a murine thymocyte proliferation assay, co-stimulated by Concanavalin A (ConA) and interleukin-2 alpha (IL-2) for inventive compounds nos. 1410, 1439, 1541, 1553, 1553S, 1560, 1565, 2548R, 2548S and 2562.

FIGS. 8A, 8B, 8C and 8D report results for inventive compounds nos. 1409 and 1560 in an assay for determining inhibitive characteristics (and cytotoxicity) of the inventive compounds in on PDGF-stimulated Balb/3T3 cell proliferation.

FIGS. 9A, 9B, 9C and 9D report data for inventive compound no. 3524 obtained in a TNF adherence assay using the Jurkat, Ramos, HT-29 and NCI-H460 cell lines, respectively. As shown in these four figures, the compound tested reduces the percentage of Jurkat, Ramos, HT-29 or NCI-H460 cells which adhere to the HUVECs.

Figure 9A:
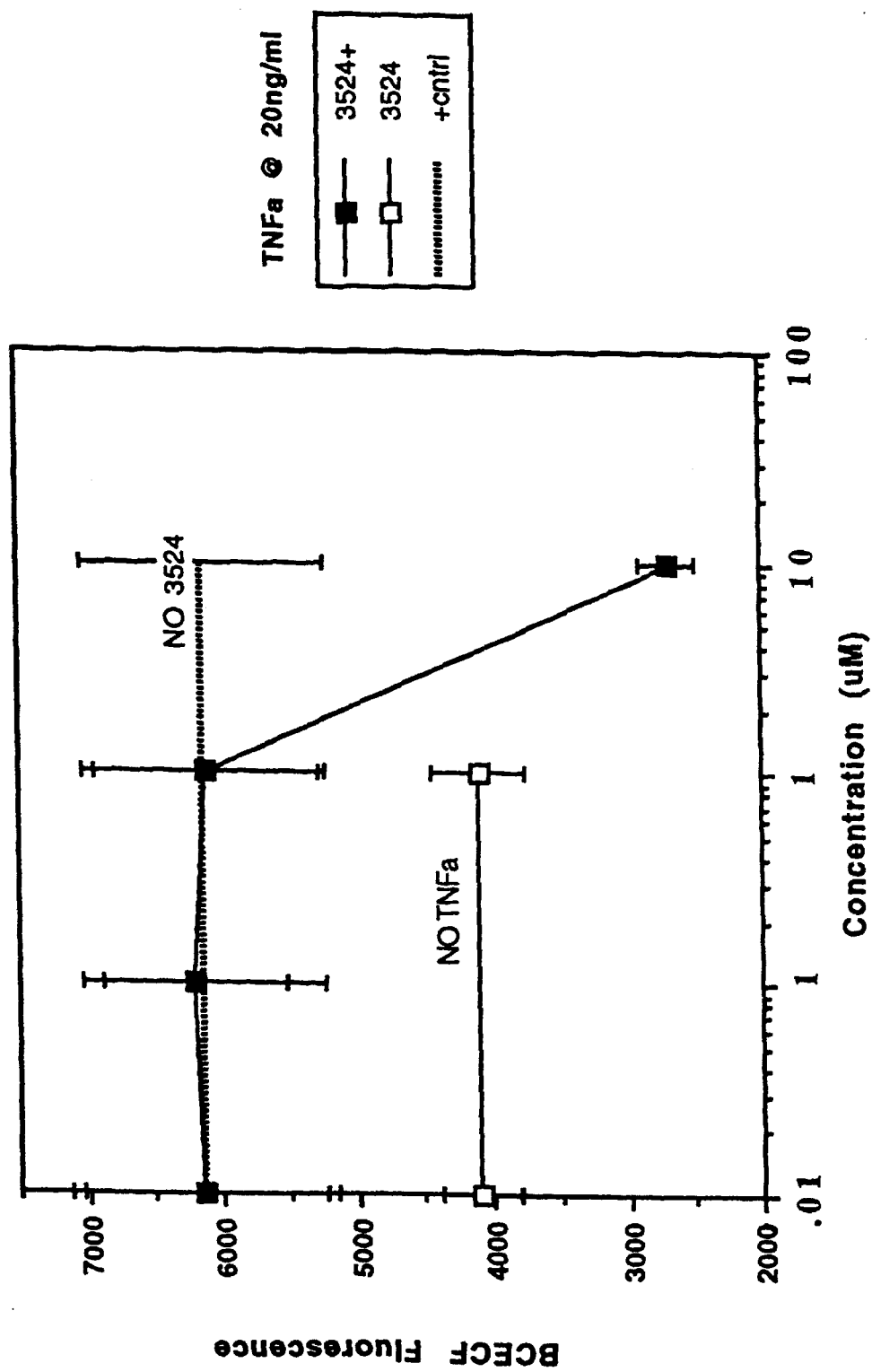
Figure 9B:
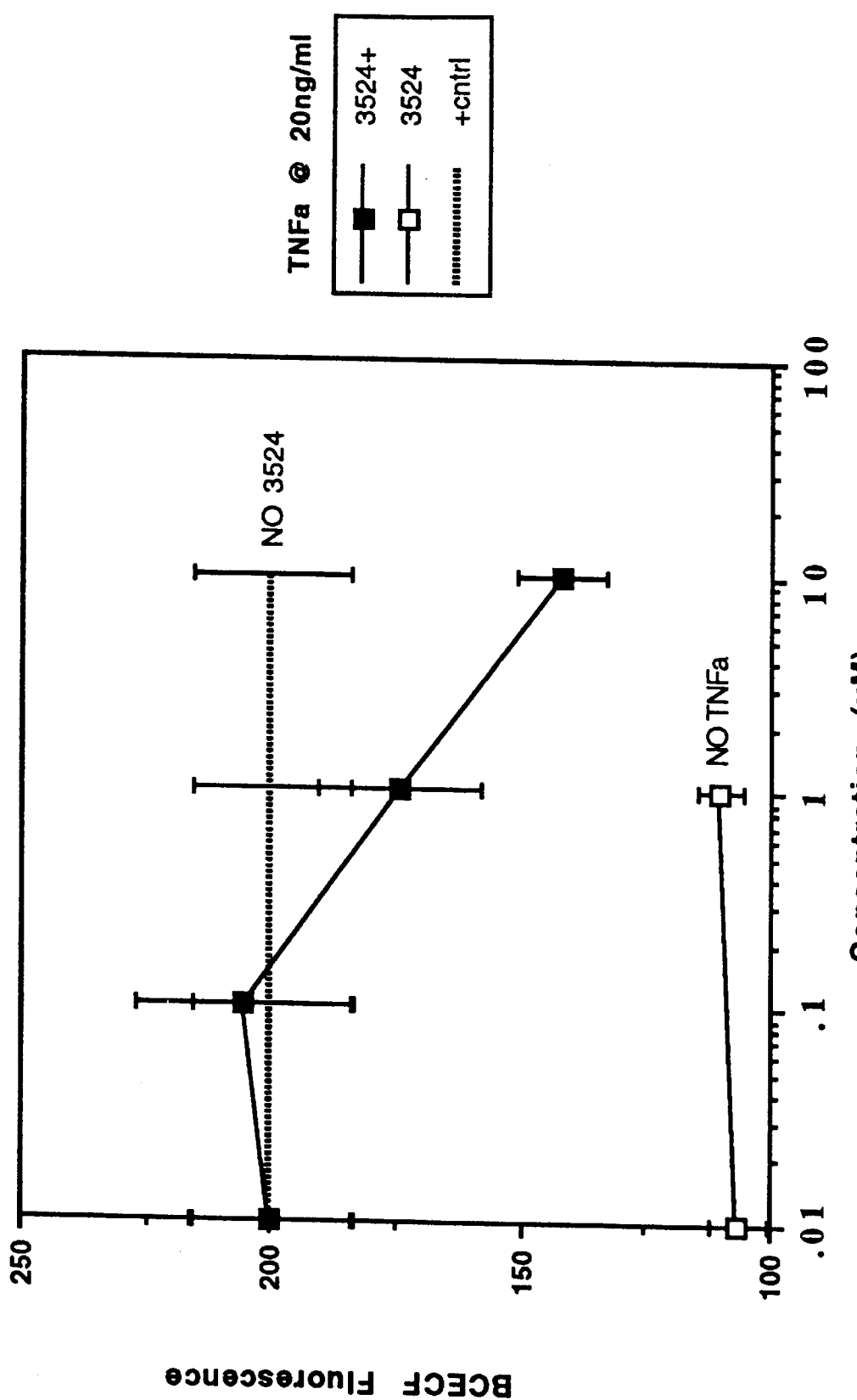
Figure 9C:
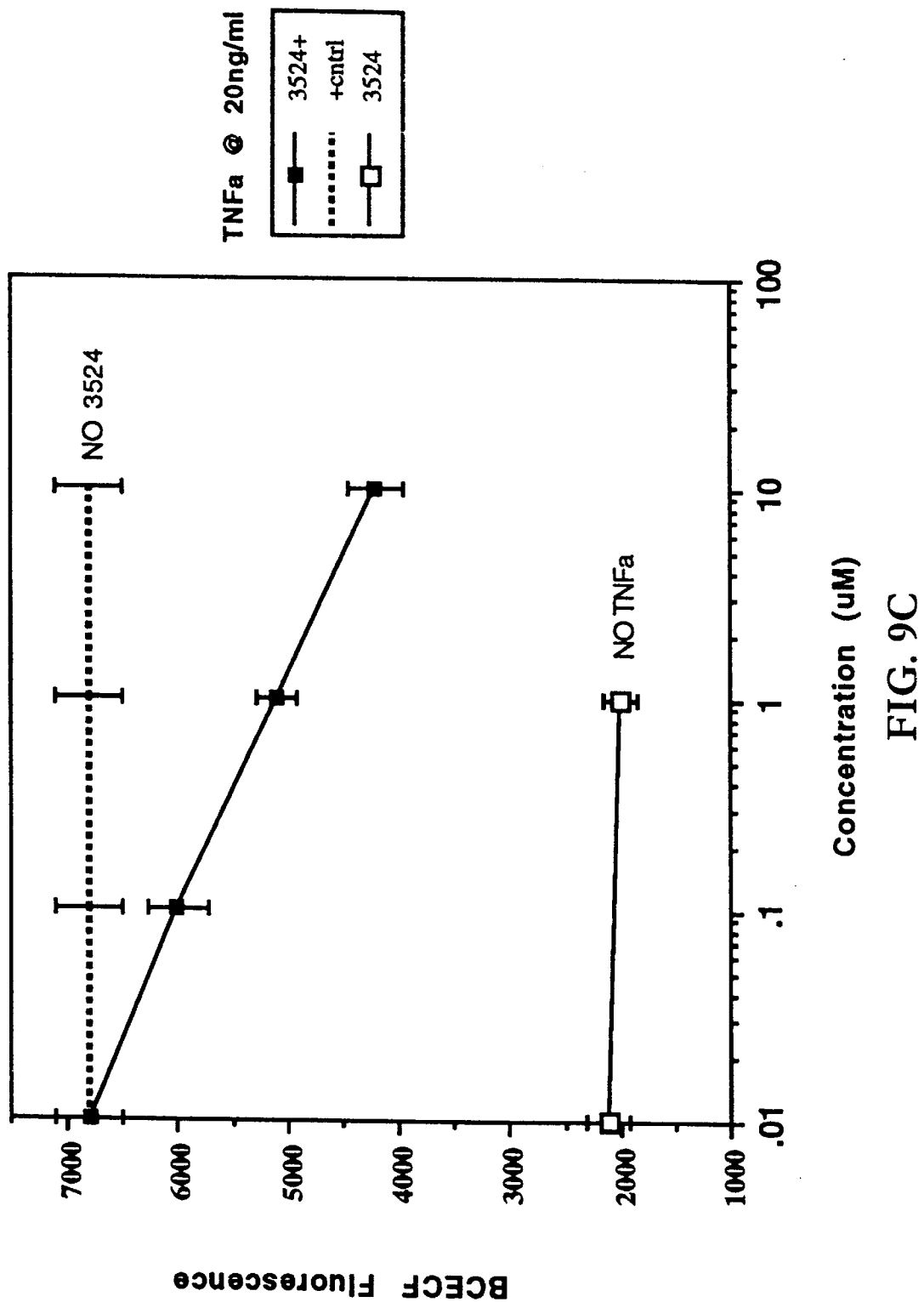
Figure 9D:
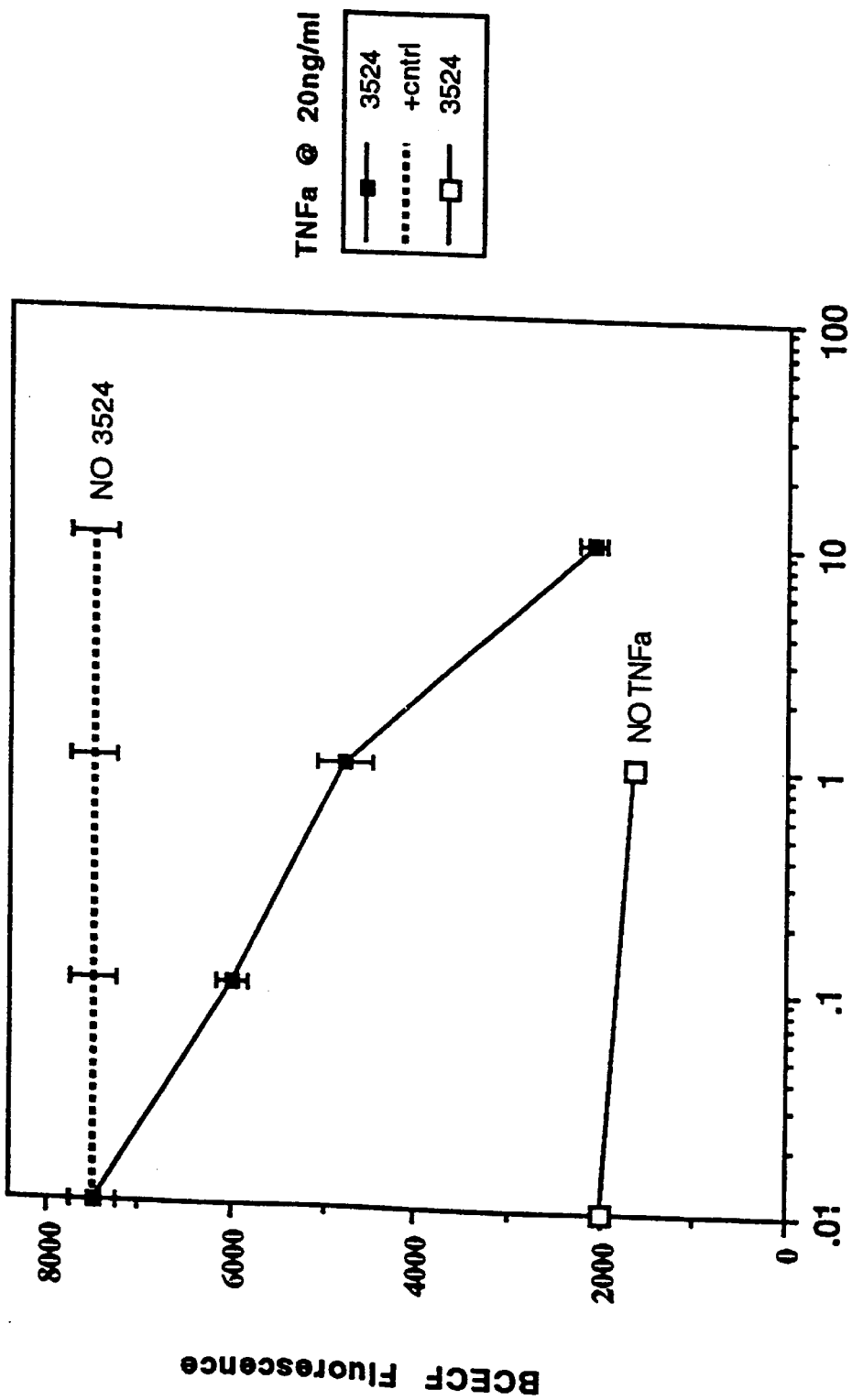
Figure 9E:
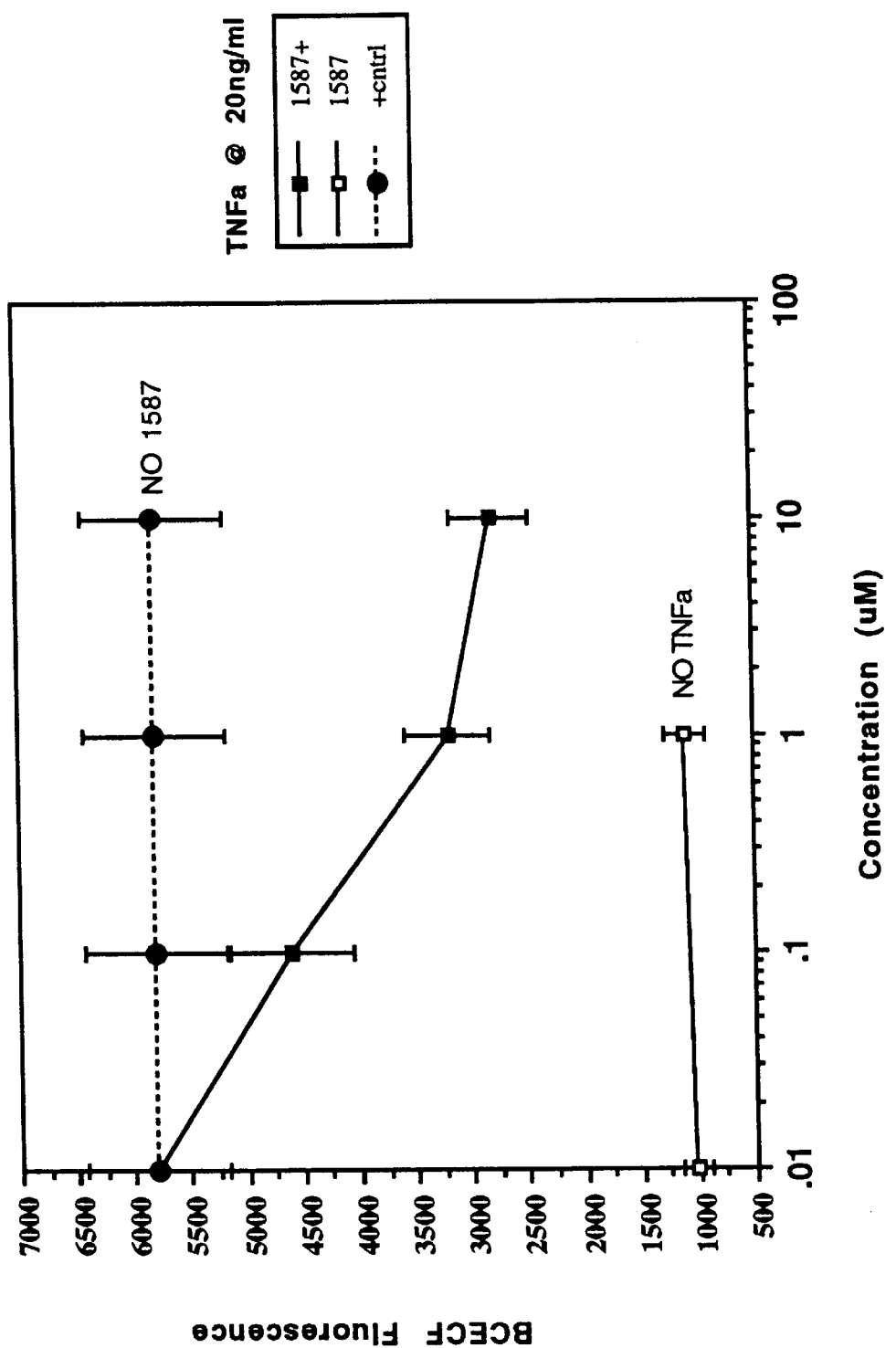
Figure 9F:
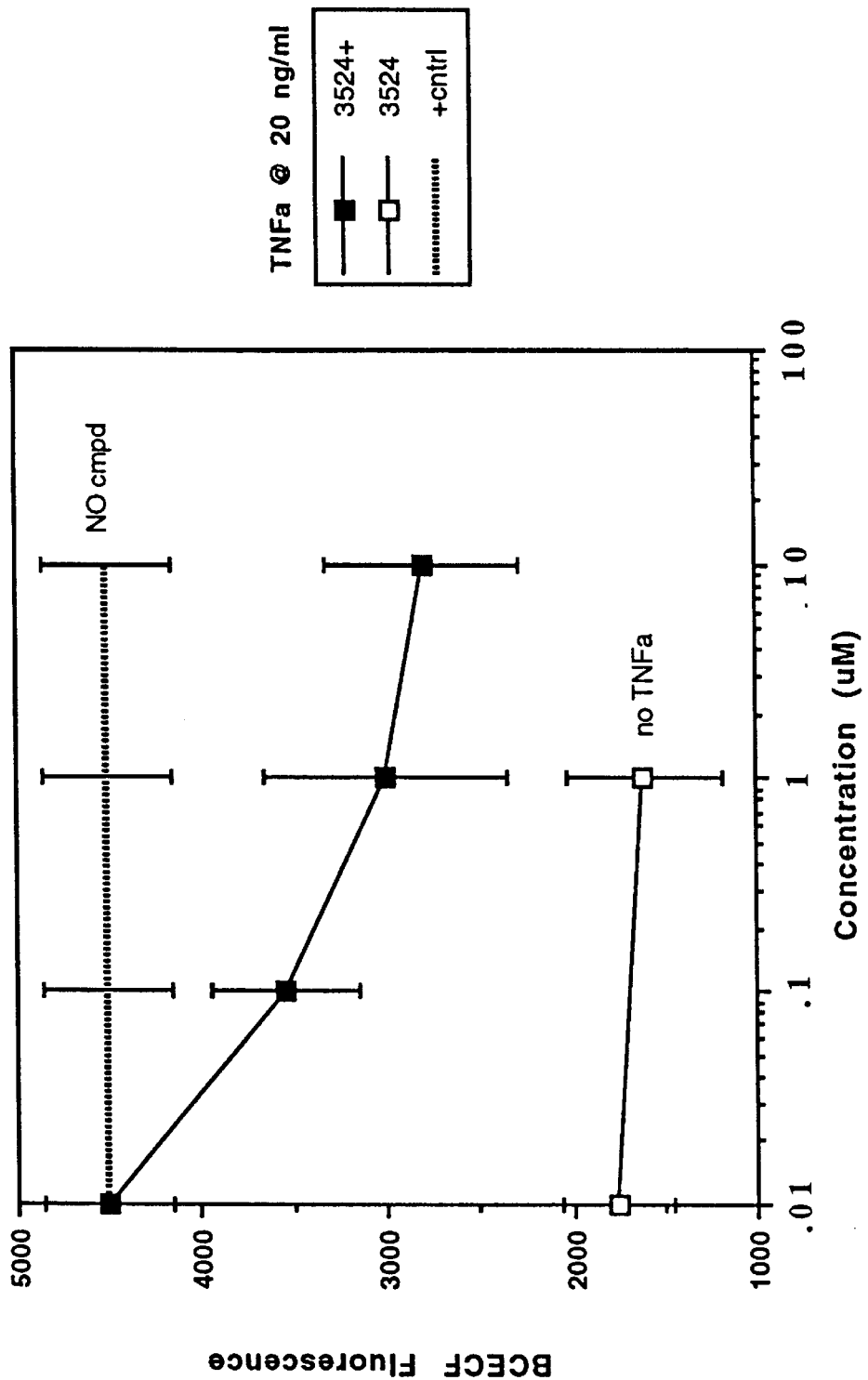

FIGS. 9E and 9F report data for inventive compounds nos. 1587 and 3524 in reducing percent adherence of THP-1 cells to HUVECs in a TNF adherence assay.

Figure 9G:
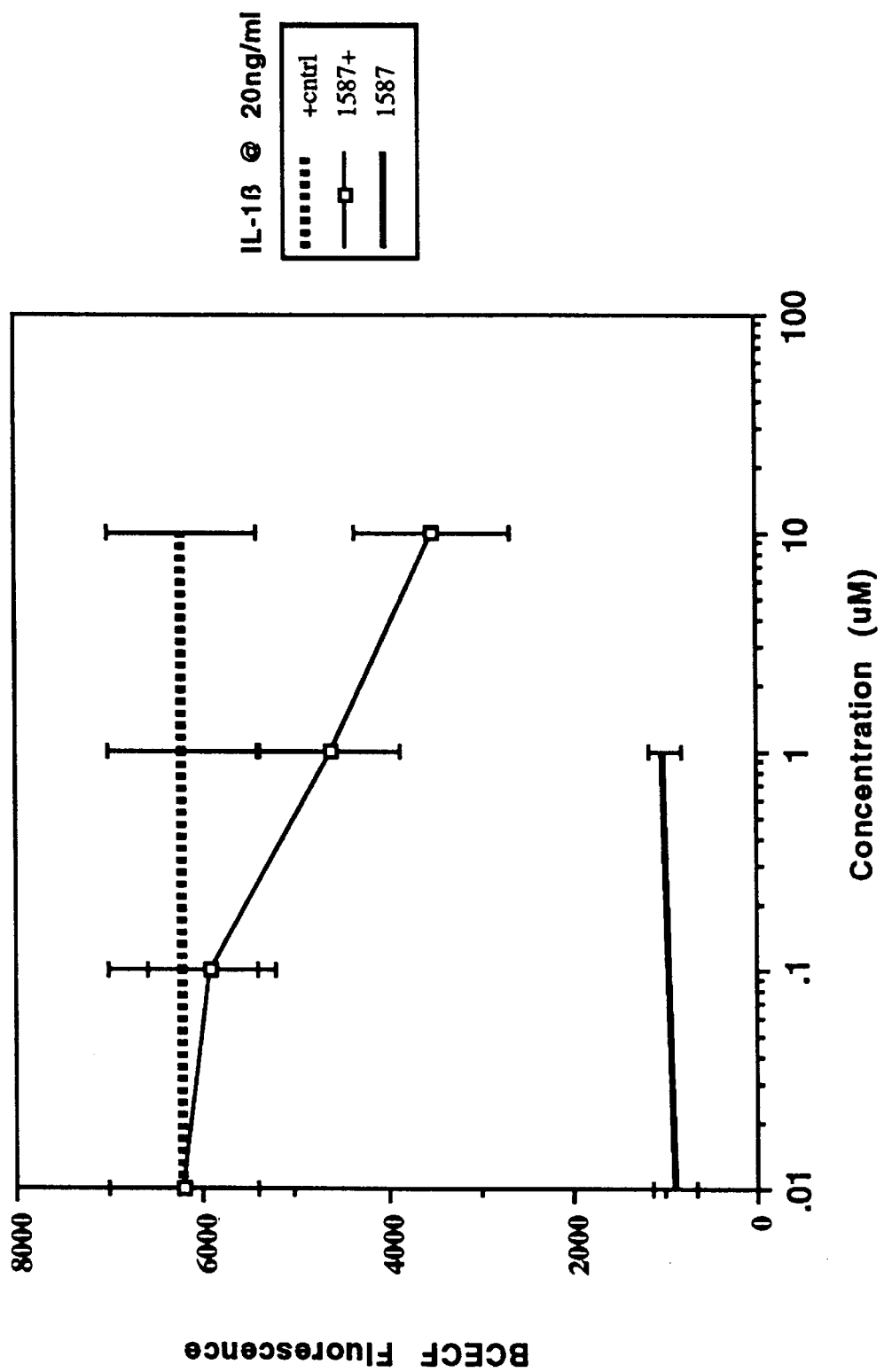
Figure 9H:
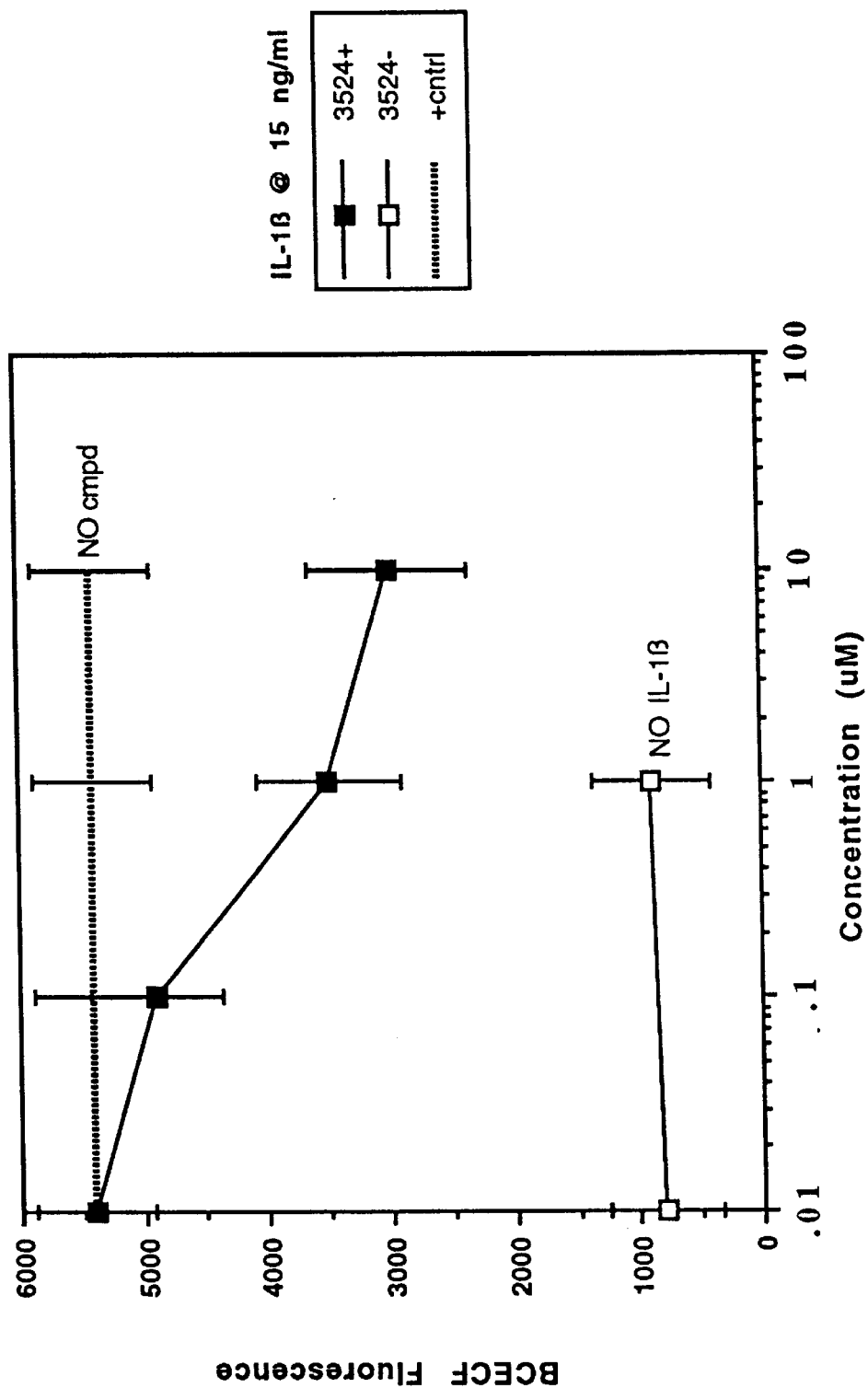

FIGS. 9G and 9H report data obtained in an assay used to determine inhibitive activity of the inventive compounds on adherence of THP-1 cells to IL-1β-stimulated HUVECs.

Figure 10:
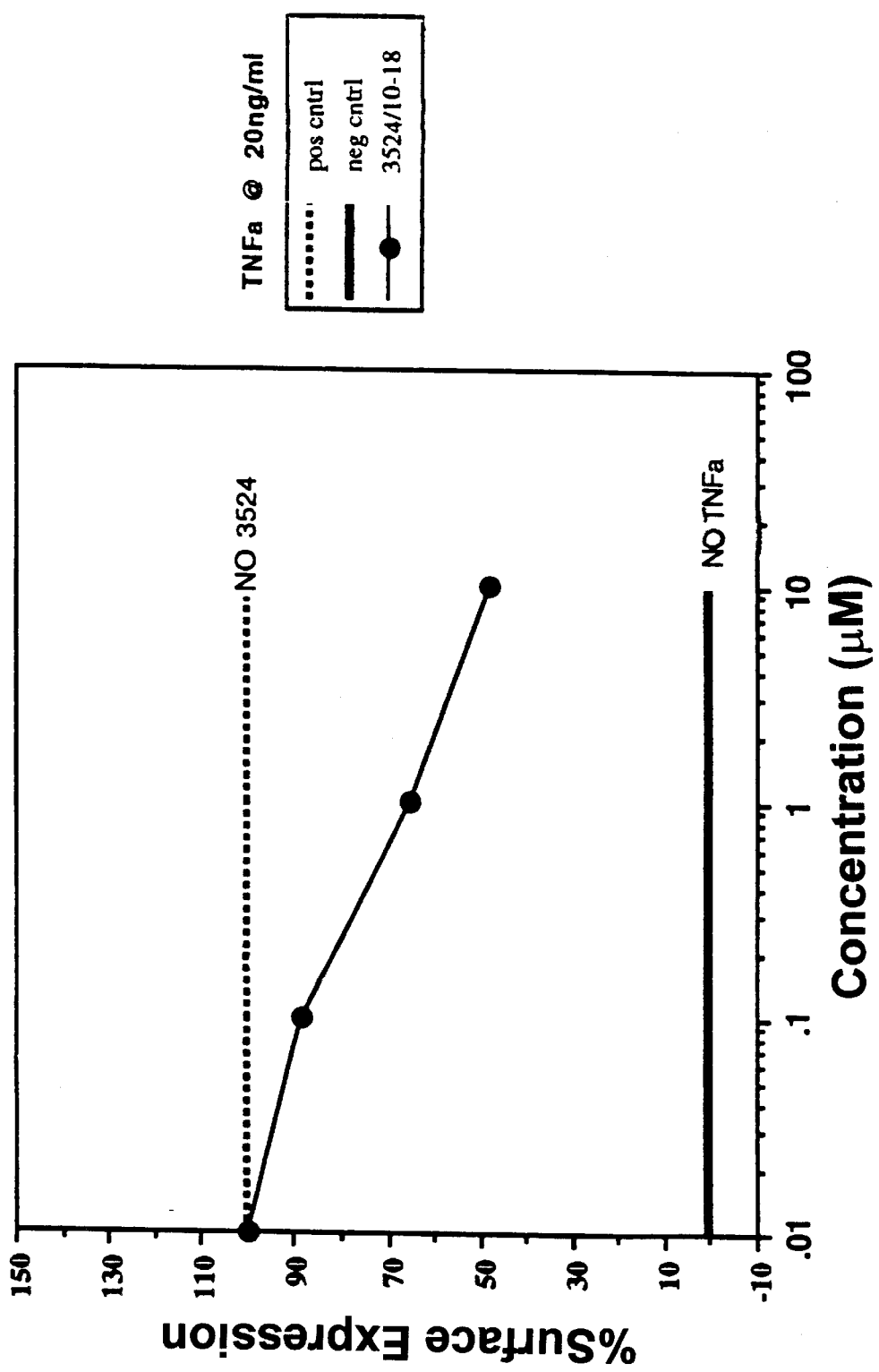

FIG. 10 illustrates results obtained in an assay measuring an ability of the inventive compounds to inhibit vascular cell adhesion molecule (VCAM) expression on HUVEC.

Figure 11:
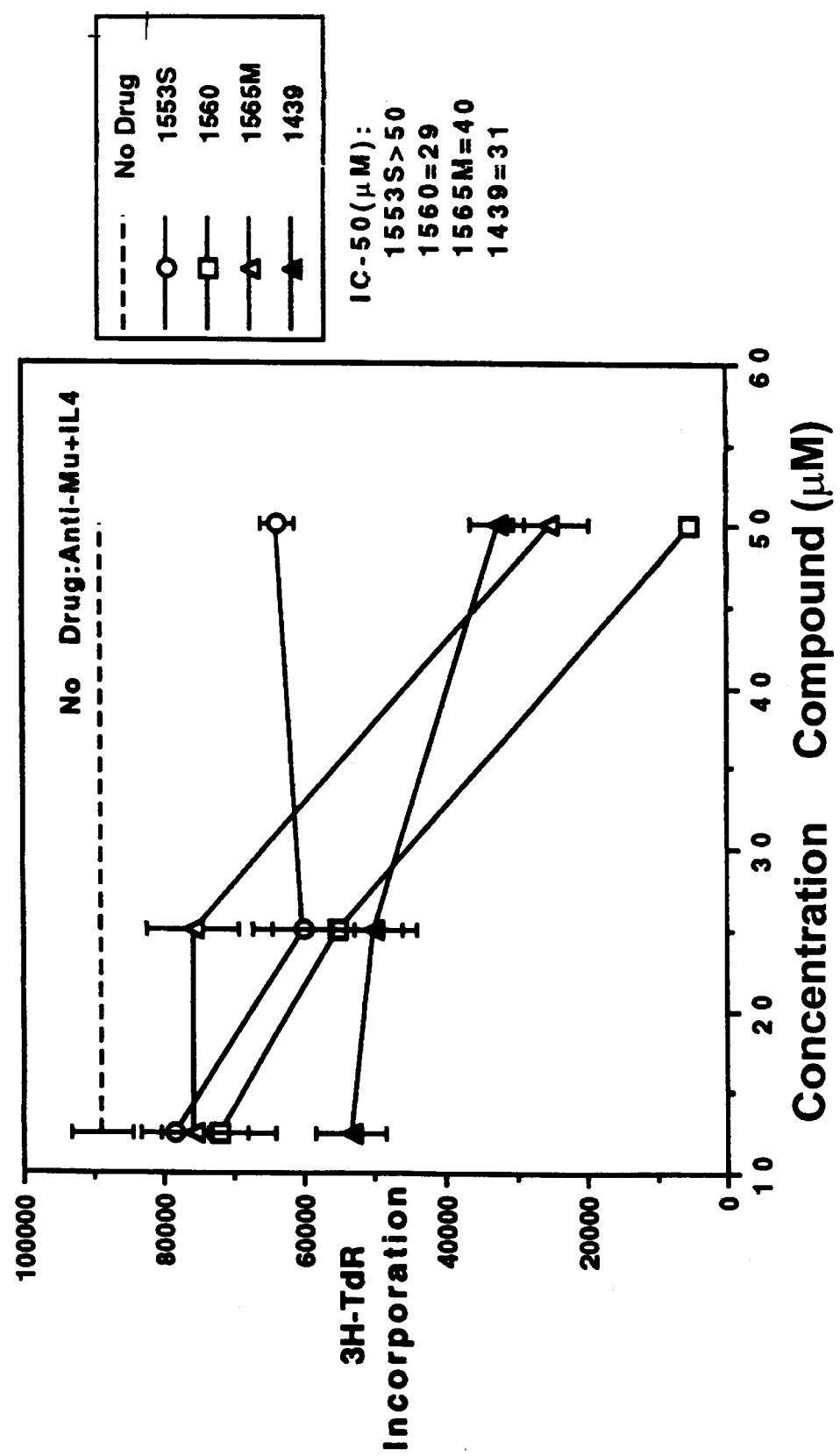

FIG. 11 reports data obtained in a murine splenocyte proliferation assay, the splenocytes being co-stimulated by anti-mu and interleukin-4, for determining inhibitive effects of the inventive compounds.

Figure 12:
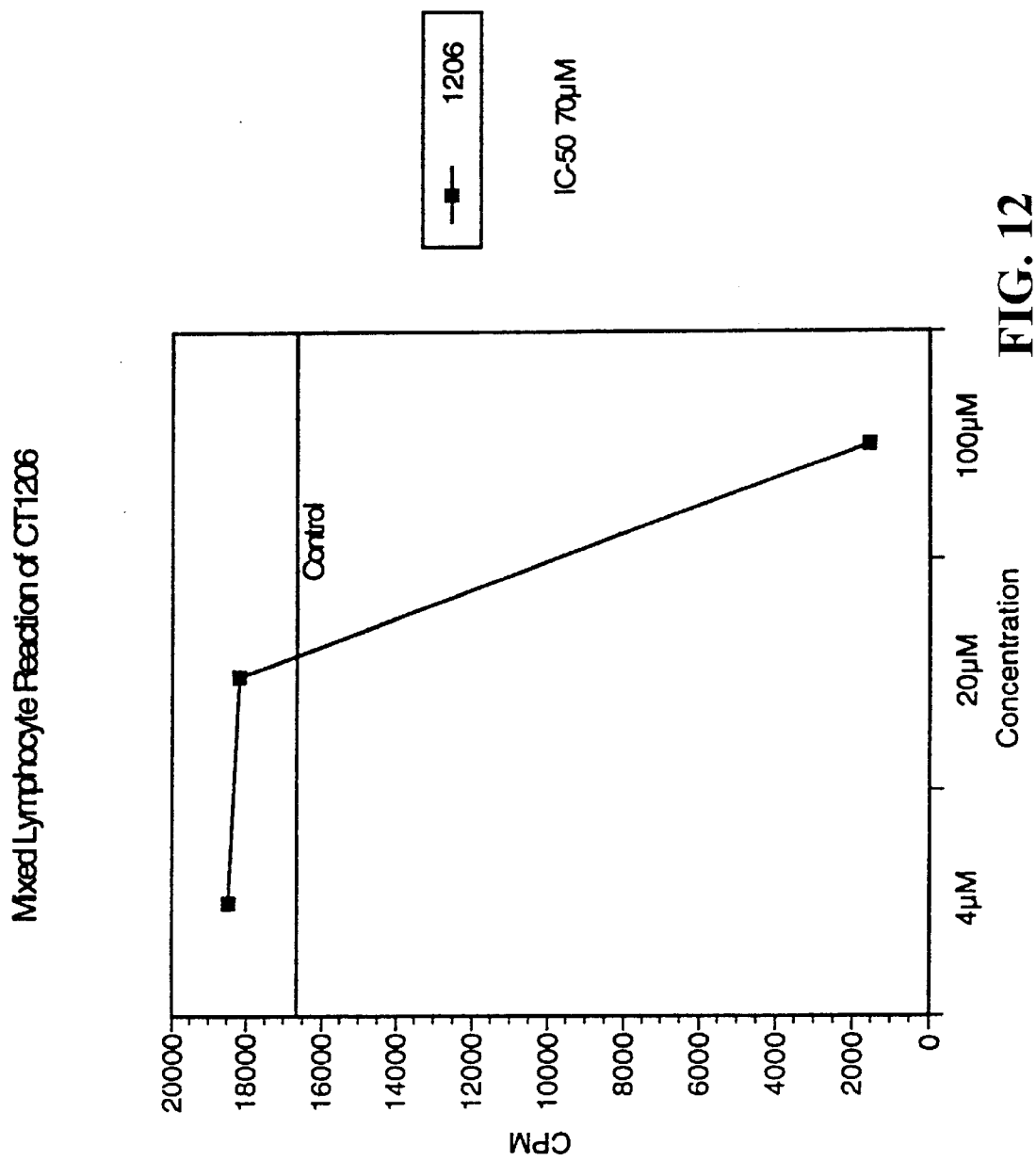

FIG. 12 shows inhibitive results for representative inventive compounds in a mixed lymphocyte reaction assay.

Figure 13:
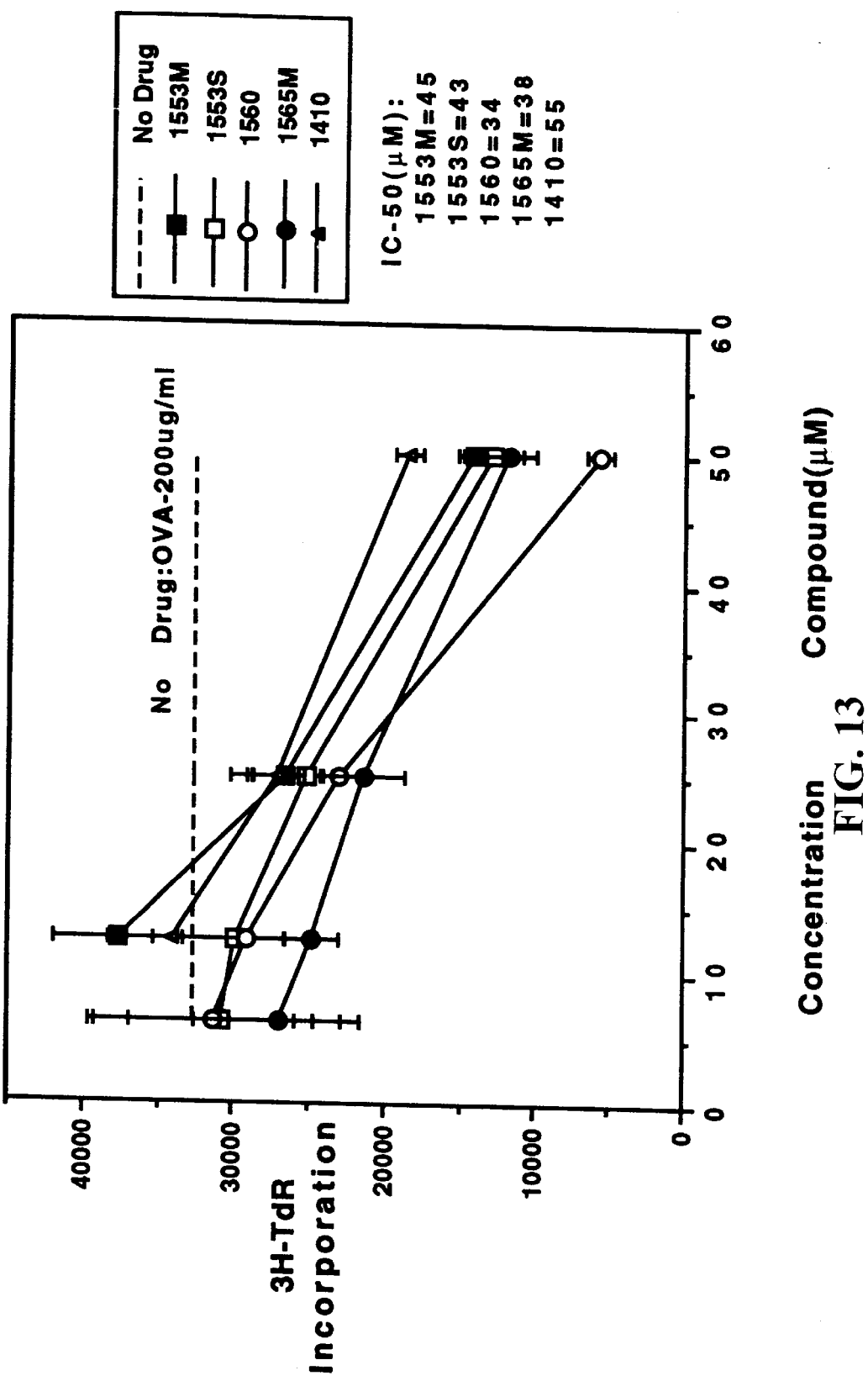

FIG. 13 reports inhibitive results obtained for inventive compounds nos. 1410, 1553 (racemic), 1553(S), 1560 and 1565 on ovalbumin-induced proliferation in murine lymph cells.

Figure 14:
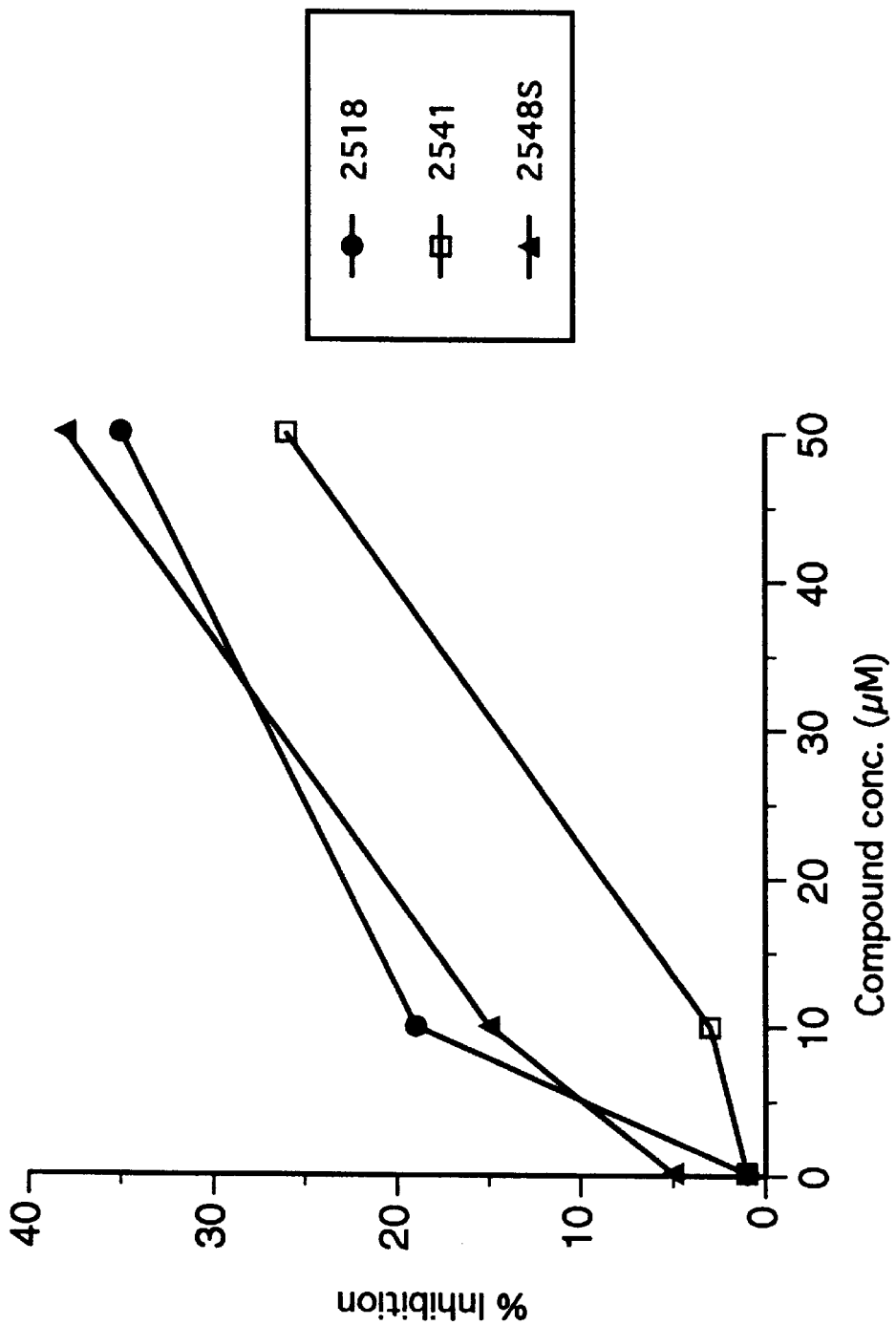

FIG. 14 shows data, plotted as percent inhibition of the maximal response (TNF-α levels in the supernatant) vs. concentration of inventive compound, illustrating the inhibitive effects of the inventive compounds tested on LPS-induced TNF release using whole human blood.

DETAILED DESCRIPTION OF THE INVENTION

The invention is directed to a defined genus of inventive compounds which can control cellular behavior by a particular phase of a secondary messenger pathway system (Bursten et al., *J. Biol. Chem.* 266:20732, 1991). The second messengers are lipids or phospholipids and use the following abbreviations:

PE=phosphatidyl ethanolamine
LPE=lysophosphoethanolamine
PA=phosphatidic acid
LPA=lysophosphatidic acid
DAG=diacylglycerol
LPLD=lysophospholipase-D
LPAAT=lysophosphatidic acid acyl transferase
PAPH=phosphatidic acid phosphohydrolase
PLA2=phospholipase A-2.
PLD=phospholipase D
PAA=phosphoarachidonic acid
PLA-2=phospholipase A2
PC=phosphatidyl choline "remodeled" PA, cyclic pathway=PAA, LPA, PA and DAG intermediates substituted with L-saturated, 2-linoleoyl or 1,2-dileolyl/1,2-sn-dilinoleoyl at the indicated sn-1 and sn-2 positions.

"Classical PI Pathway"=PI, DAG, PA intermediates substituted with 1-stearoyl, 2-arachidonoyl fatty acyl side chains.

"PLD-generated PA"=PE, PC, LPA, PA and DAG intermediates substituted with, e.g., 1,2-sn-dioleoyl-, 1-alkyl, 2-linoleoyl-, and 1-alkyl, 2-docosahexaneoyl-side chains.

Lysophosphatidic acid transferase (LPAAT) effects the synthesis of phosphatidic acid (PA) from lysophosphatidic acid (LPA) by incorporation of an acyl group from acyl CoA. Hydrolysis of the phosphate moiety by PA phosphohydrolase (PAPH) results in the formation of DAG. These aspects of the pathway appear to be activated immediately (within a minute) upon stimulation by a primary stimulus (e.g., a cytokine such as interleukin-1 or TNF) acting at a receptor on a cellular surface. An immediate detectable effect is an elevation of levels of PA and DAG. Administration of the compounds of the invention reverse this elevation.

The compounds of the invention, include inhibitors of subspecies of LPAAT in PAPH enzymes with substrate specificity for intermediates with 1,2-diunsaturated and 1-alkyl, 2-unsaturated subspecies. One representative example of such an inhibitor (although not within the genus of inventive compounds) is PTX. PTX blocks PAPH in a specific activation pathway that does not involve PI but rather derives from a PA that is largely composed of 1,2-diunsaturated and 1-alkyl,2-unsaturated subspecies. This was shown, for example, by the demonstration that human mesangial cells stimulated with TNF produce DAG from PI and regenerate PI in the absence and the presence of PTX. In the latter system there is no evidence to suggest that PA or DAG are derived from sources other than PI. It should be emphasized that the compounds of the invention affect that subset of PAPH and LPAAT that relates to substrates with unsaturated fatty acids other than arachidonate in the sn-2 position, not the housekeeping forms of these enzymes that serve the PI pathway.

Compounds of the Invention

The inventive epoxide-containing compounds include enantiomers and/or diastereomers, salts, solvates, hydrates and mixtures thereof and have the following formula I:

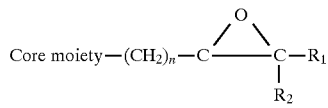

wherein n is an integer from about 4 to about 16, $R_1$ and $R_2$ are hydrogen, halogen or $C_{1-12}$ alkyl or alkenyl and the core moiety has a non-cyclic structure or is at least one five- to seven-membered cyclic structure. Preferably, n is an integer from about 4 to about 12, more preferably from about 4 to about 10. $(CH_2)_n$ may be substituted by a hydroxyl, halogen, oxygen, a $(C_{1-4})$ alkyl group or a dimethylamino group. The alkyl or alkenyl groups may also be substituted by a hydroxy, halo or dimethylamino group and/or interrupted by an oxygen atom or $C_{1-4}$ alkyl. Exemplary halogens include bromine, chlorine, fluorine and iodine.

A non-cyclic core moiety may be, for example, acetamide, amide, amine, amino acid (one or two), carboxyl, ester, halogen atom, terminal hydrogen atom, hydroxyl, glutaric acid, glycine derivative, ketone, phosphate, phosphonate, sulfate, sulfonate, sulfone, sulfoxide, simple ionic functional group, thiol or thiolester. Exemplary core moiety amino acids may include one or more of the following: alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine and valine. The non-cyclic core moiety may preferably be a dipeptide comprising two amino acids selected from the foregoing exemplary list. Exemplary core halogen atoms include bromine, chlorine, fluorine and iodine.

A core moiety may have from one to three, five- to six-membered ring structures in a predominantly planar configuration. Preferably, an epoxide-containing functional group is bonded to a ring nitrogen if one exists. For example, the core moiety may be selected from the group consisting of substituted or unsubstituted barbituric acid; benzamide; benzene; biphenyl; cyclohexane; cyclohexanedione; cyclopentanedione; lactam; glutarimide; homophthalimide; hydrophthalimide; imidazole; imidazole amide; indomethacin; isocarbostyril; lumazine; napthlalene; phenol; pteridine; pthalimide; piperidine; pyridine; pyrimidine; pyrrole amide; quinolizinedione; quinazolinone; quinolone; recorsinol; salicylic acid and derivatives thereof; stilbene; succinimide; theobromine; thymine; triazine; tricyclododecane; uric acid; uracil; vitamins A, E or K; or xanthine.

Preferred cyclic cores include substituted or unsubstituted glutarimide, methylthymine, methyluracil, thymine, theobromine, uracil and xanthine, most preferably halogen-substituted xanthine. Exemplary preferred cores include: N-methylbenzamide, 1,3-cyclohexanedione, 1,3-cyclopentanedione; 1,3-dihydroxynaphthalene; 1-methyllumazine; methylbarbituric acid; 3,3-dimethylglutarimide; orotic acid; orthophenol; tetra or hexahydrophthalimide; 2-piperidone; prostacyclin; 2-hydroxypyridine; methyldihydroxypyrazolopyrimidine, specifically, 1,3-dimethyldihydroxypyrazolo[4,3-d]pyrimidine; methylpyrrolopyrimidine; 1-methylpyrrolo[2,3-d] pyrimidine; 1,3-dihydroxynapthalene; 1-pyrrole amides; 2-pyrrole amides; 3-pyrrole amides; 1,2,3,4-tetrahydroisoquinolone; 1-methyl-2,4(1H,3H)-quinolizinedione (1-methylbenzoyleneurea); quinazolin-4(3H)-one; sulindac; dihydrothymine; alkyl-substituted (C1–6) thymine; 2,4-dioxohexahydro-1,3,5tetrazine; methylthymine; alkyl-substituted (C1–6) uracil; uracil fused to naphthalene; 6-aminouracil; 1-methyldihydrouracil; 1-methyluracil; 5- and/or 6-position substituted uracils (such as, for example, 5-bromouracil); B-ionone as vitamin A; 2,6,6-trimethyl-1-cyclohexene-1-acetaldehyde as vitamin A; tetralone to vitamin K; 1,7-dimethylxanthine, 3,7-dimethylxanthine; 3-methylxanthine; 3-methyl-7-methylpivaloylxanthine; 8-substituted xanthines (having substituents such as nitrogen or sulfur); and 7-methylhypoxanthine.

Preferably, an epoxide-containing group is bonded to a nitrogen of the core moiety, most preferably, the core moiety is xanthine and the epoxide-containing group is bonded to an $N_1$ xanthine nitrogen and $N_3$ and $N_7$ xanthine nitrogens are independently substituted by a member selected from the group consisting of hydrogen, methyl, fluoro, chloro and amino.

Synthesis of the Inventive Compounds

The invention includes a method for preparing the inventive compounds. An exemplary method for preparing the inventive compounds is discussed below and in the following examples. In a synthesis according to the invention, a compound containing a desired core (intended as a "core moiety" in compounds of the invention) undergoes a reaction to produce an anion of the core-containing compound and subsequently reacting the anion with a substituted olefin to displace a targeted group on the olefin, resulting in an intermediate product. In a preliminary reaction, a predetermined amount of a core-containing compound is reacted with a suitable base, a solvent and a substituted olefin, the substituted olefin having at least one functional group which may be substituted in a displacement reaction by the desired core-containing compound.

Preferred bases include, but are not limited to, sodium hydride, sodium amide, sodium alkoxide, lithium hydride, potassium hydride, lithium amide and potassium amide. An especially preferred base is sodium hydride. Preferred solvents may be dimethylsulfoxide, dimethylformamide, or an alcohol. Exemplary preferred alcohols include, but are not limited to, methanol, ethanol or isopropanol. Any substituted olefin comprising a chain structure of the inventive compounds may be used in the preliminary reaction according to the invention. Preferred olefins may be ω-substituted olefins. Preferred substituted olefins include, but are not limited to halo-substituted, alkyl sulfonyloxy, and aryl sulfonyloxy olefins and may be toluene sulfonyloxy or methane sulfonyloxy olefins.

The intermediate product, having a composite structure of the core-containing compound and substituted olefin, may then be converted to a corresponding epoxide. In the method according to the invention, the intermediate product may be reacted with an organic peracid to obtain a desired epoxide. Preferred exemplary organic peracids include aryl and alkyl peracids like 3-chloroperoxybenzoic acid, peracetic acid and/or halo-substituted peracids, such as trifluoroperacetic acid. Other exemplary acids are peroxybenzoic acid, performic acid and the like. An especially preferred peracid is 3-chloroperoxybenzoic acid.

Alternatively, the intermediate product may be converted first to a corresponding diol by reacting the intermediate product with a suitable oxidizing agent. Preferred oxidizing agents include, but are not limited to, osmium tetroxide. Preferred oxidizing agents, such as osmium tetroxide may require a catalytic amount of the oxidizing agent in the presence of a regenerating agent. Exemplary, regenerating agents may be 4-methylmorpholine-N-oxide and trimethylamine-N-oxide. An especially preferred regenerating agent is 4-methylmorpholine-N-oxide. In a subsequent halogenation reaction, the resulting diol is converted to a haloester using a halogenating agent in the presence of an organic acid. Exemplary halogenating agents include hydrogen bromide and hydrogen chloride. Preferred organic acids may be formic acid, acetic acid and propionic acid. The resulting haloester is subsequently reacted with a basic ester-hydrolyzing reagent to obtain a desired epoxide product according to the invention. Preferred ester-hydrolyzing agents include, but are not limited to metal alkoxides and metal hydroxides. Especially preferred metal alkoxides are sodium methoxide, ethoxide, isopropoxide and pentoxide. A preferred metal hydroxide is sodium hydroxide.

Alternatively, the inventive compounds may be prepared by reacting a compound having at least one epoxide substituent with a predetermined amount of a compound containing a desired core (intended as a "core moiety" in compounds of the invention) with a suitable base and a solvent. The compound having at least one epoxide substituent has at least one other, appropriately-substituted functional group, which may be substituted in a displacement reaction by the core-containing compound. Other functional groups may include, but are not limited to, for example, halogen atoms.

The compounds of the invention may be provided as enantiomeric or diastereomeric mixtures or in resolved or partially resolved forms. Standard procedures are used for resolving optical isomers. Different enantiomeric variants (e.g., stereoisomers and chiral forms) of the inventive compound may have different drug activities, based upon their differential ability to inhibit PAPH and LPAAT. An optical isomer, substantially free of the corresponding enantiomer and/or diastereomers, is at least about 85% of a relevant optical isomer, preferably at least about 95% relevant optical isomer and especially at least about 99% or higher relevant optical isomer. Most preferably an amount of other optical forms is undetectable.

The invention further comprises a pharmaceutical composition comprising one or a plurality of inventive compounds and a pharmaceutically acceptable carrier or excipient. The cells to be treated with an inventive compound or inventive pharmaceutical composition may either be contacted with the compound of the invention in in vitro culture, in an extra corporeal treatment, or by administering the compound of the invention or pharmaceutical composition thereof to a subject whose cells are to be treated.

The invention provides a pharmaceutical composition comprising an inventive compound and a pharmaceutically acceptable excipient. The pharmaceutical composition may be formulated for oral, parenteral or topical administration to a patient.

The invention further provides a pharmaceutical composition comprising an inventive compound and a pharmaceutically acceptable excipient, the pharmaceutical composition being formulated for oral, parenteral or topical administration to a patient. A pharmaceutical composition may alternatively comprise one or a plurality of inventive compounds and a pharmaceutically acceptable carrier or excipient. Treatment of individuals with an inventive compound or pharmaceutical composition may include contacting with the inventive compound in vitro culture, in an extra corporeal treatment, or by administering (oral, parenteral or topical) the inventive compound or pharmaceutical composition to a subject whose cells are to be treated.

Exemplary, preferred compounds of the invention include both R and S enantiomers and racemic mixtures of the following compounds:

1103 N-(5,6-Oxidohexyl) phthalimide

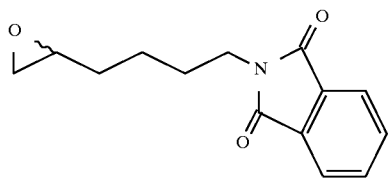

1105 N-(8,9-Oxidononyl) phthalimide

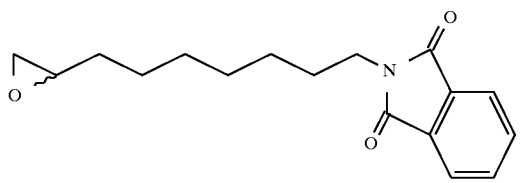

1109 N-(10,11-Oxidoundecyl) phthalimide

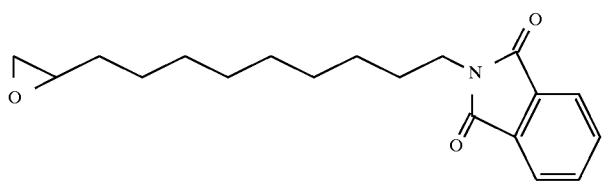

-continued

| | | |
|---|---|---|
| 1114 | N-(10,11-Oxidoundecyl) homophthalimide | 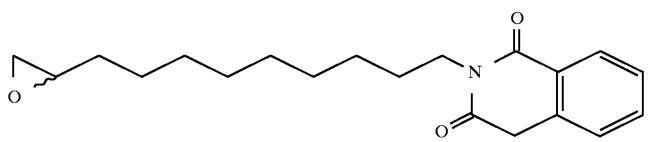 |
| 1206 | 1-(5,6-Oxidohexyl)-3-methylbenzoyleneurea | 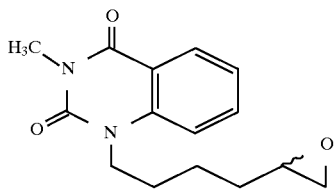 |
| 1216 | 3-(10,11-Oxidoundecyl) quinazoline-4(3H)-one | 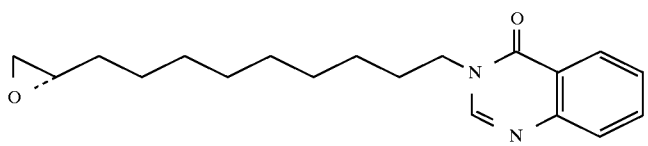 |
| 1301 | N-(5,6-Oxidohexylamido) glutaric acid, methyl ester | 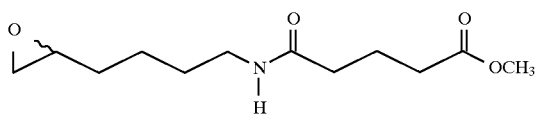 |
| 1308 | 1,2-Oxido-11-(N-methylacetamido) undecane | 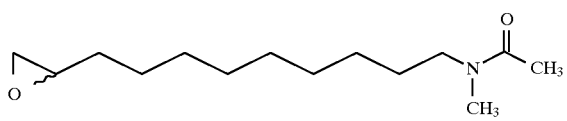 |
| 1310 | 1,2-Oxido-11-undecanol | 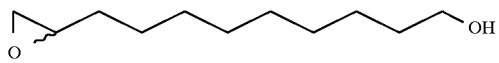 |
| 1316 | 10,11-Oxidoundecanoic acid amide | 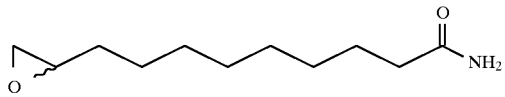 |
| 1317 | 10,11-Oxidoundecanoic acid N-methyl amide | 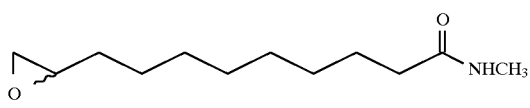 |
| 1318 | 10,11-Oxidoundecanoic acid N,N-dimethyl amide | 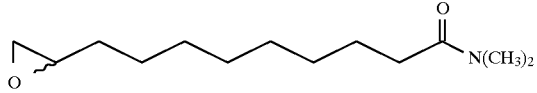 |
| 1321 | N-(10,11-Oxidoundecyl) diacetamide | 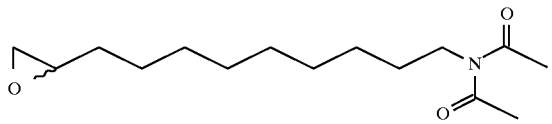 |
| 1409 | 1-(8,9-Oxidononyl)-3-methyl-7-methylpivaloylxanthine | 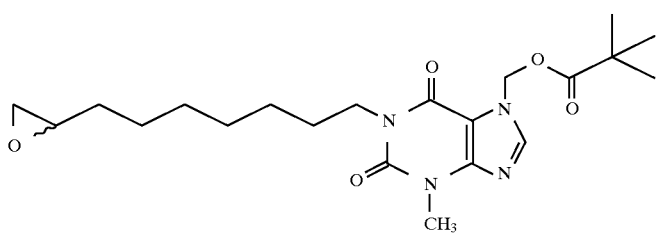 |

-continued
| | | |
|---|---|---|
| 1410 | 1-(5,6-Oxidononyl)-3-methyl-7-methylpivaloylxanthine | 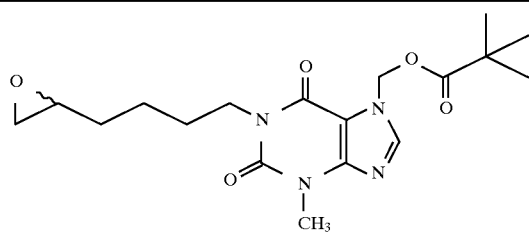 |
| 1412 | 1-(11,10-Oxidoundecyl)-3-methyl-7-methylpivaloylxanthine | 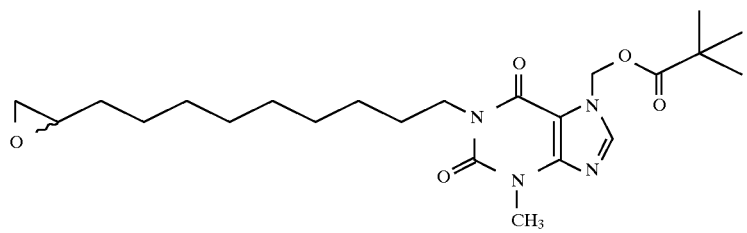 |
| 1413 | 1-(11,10-Oxidoundecyl)-3-methylxanthine | 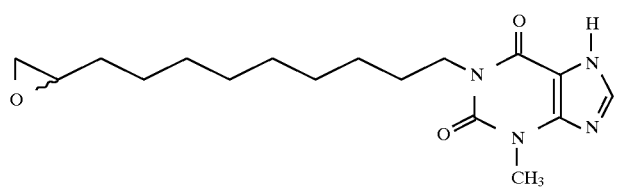 |
| 1423 | 7-(10,11-Oxidoundecyl)-1,3-dimethylxanthine | 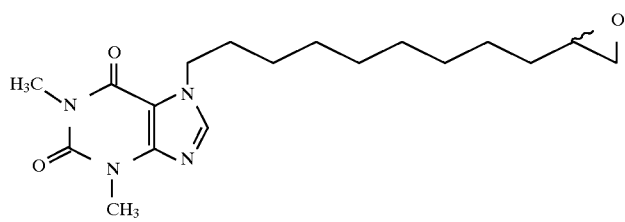 |
| 1426 | 3-(11,10-Oxidoundecyl)-1-methyl-2,4-dioxotetrahydropteridine | 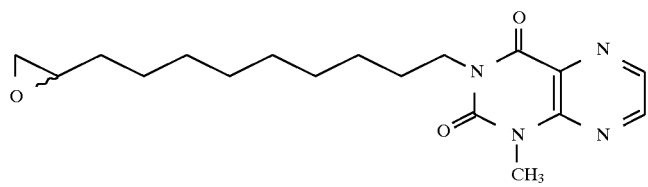 |
| 1439 | 1-(5,6-Oxidohexyl)-3-methylxanthine | 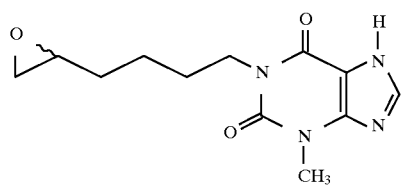 |
| 1509 | 1-(6,7-cis-Oxidononyl)-3,7-dimethylxanthine (10:1 cis:trans) | 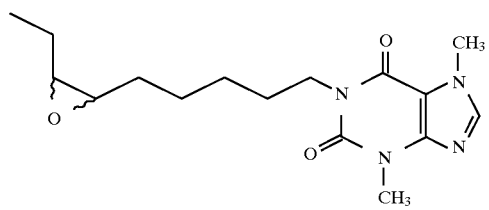 |
| 1541 | 1-(5,6-Oxidohexyl)-3,7-dimethylxanthine | 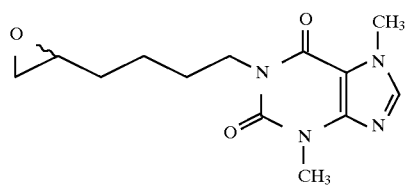 |

| | | |
|---|---|---|
| 1553 | 1-(7,8-Oxidooctyl)-3,7-dimethylxanthine | 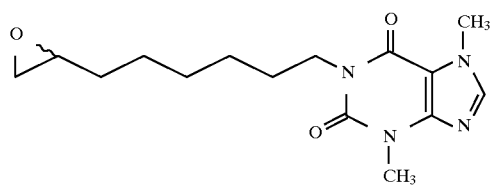 |
| 1553 (S) | 1-(7(S)-7,8-Oxidooctyl)-3,7-dimethylxanthine | 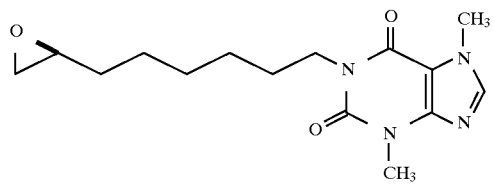 |
| 1555 | 1-(4,5-Oxidohexyl)-3,7-dimethylxanthine | 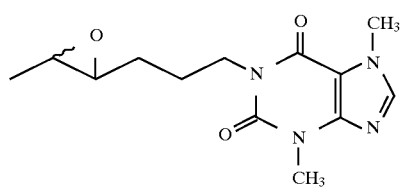 |
| 1560 | 1-(8,9-Oxidononyl)-3,7-dimethylxanthine | 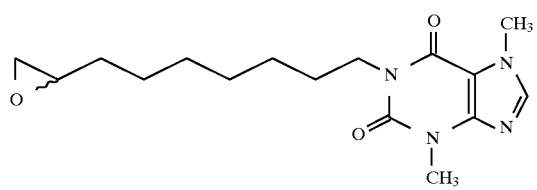 |
| 1565 | 1-(9,10-Oxidodecyl)-3,7-dimethylxanthine | 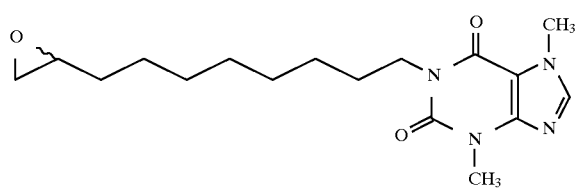 |
| 1569 | 1-(6,7-trans-Oxidononyl)-3,7-dimethylxanthine | 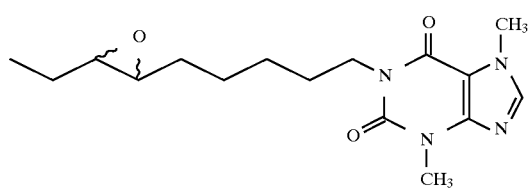 |
| 1586 | 1-(6,7-Oxidoheptyl)-3,7-dimethylxanthine | 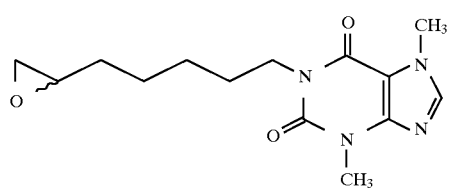 |
| 1588 (R) | 1-(3-(R)-Methyl-7-methyl-(6,7-oxidooctyl)-3,7-dimethylxanthine | 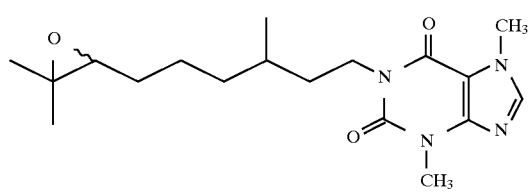 |

-continued
| | | |
|---|---|---|
| 1588 (S) | 1-(3-(S)-Methyl-7-methyl-(6,7-oxidooctyl)-3,7-dimethylxanthine | 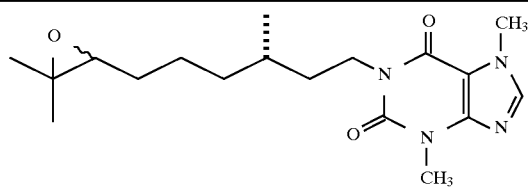 |
| 1593 | 1-(4,5-Oxidopentyl)-3,7-dimethylxanthine | 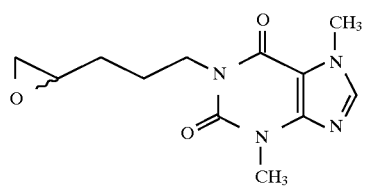 |
| 1594 | 1-(7,8-Oxidoundecyl)-3,7-dimethylxanthine | 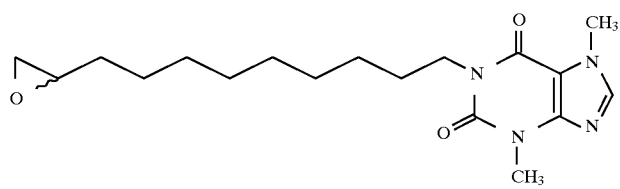 |
| 1605 | N-(5,6-Oxidohexyl) glutarimide | 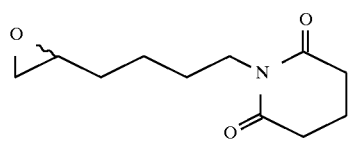 |
| 1606 | N-(8,9-Oxidononyl) glutarimide | 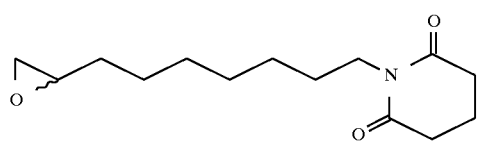 |
| 1611 | N-(10,11Oxidoundecyl) glutarimide | 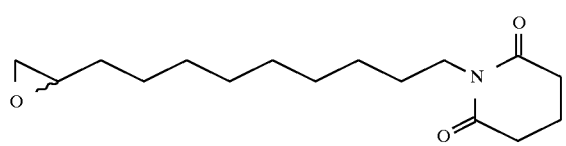 |
| 1618 | N-(10,11-Oxidoundecyl)-2-piperidone | 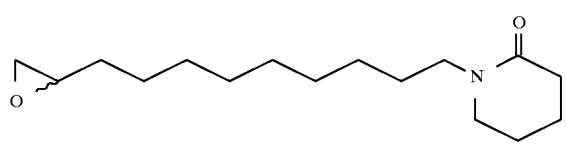 |
| 1619 | N-(5,6-Oxidohexyl) piperidine | 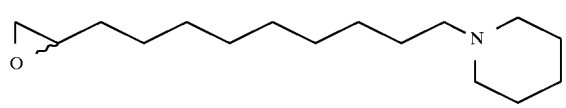 |
| 1625 | N-(10,11-Oxidoundecyl) succinimide | 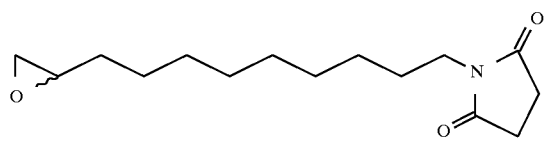 |
| 1705 | (10,11-Oxidoundecyl) benzene | 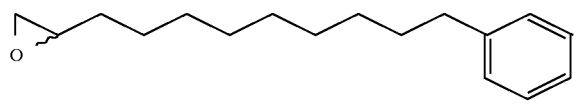 |
| 1708 | N-(10,11-Oxidoundecyl)-N-methylbenzamide | 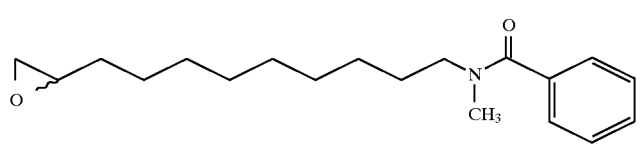 |

-continued
| | | |
|---|---|---|
| 1804 | 3-(8,9-Oxidononyl)-1-methyluracil | 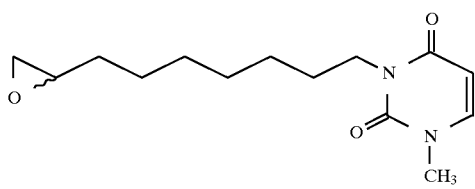 |
| 1808 | 3-(5,6-Oxidohexyl)-1-methyluracil | 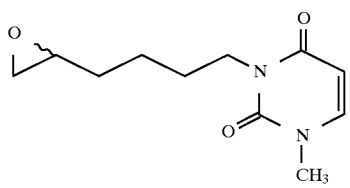 |
| 1820 | 3-(5,6-Oxidoheyl)-1-methyldihydrouracil | 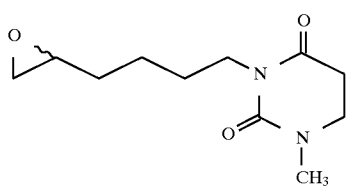 |
| 1822 | 3-(10,11-Oxidoundecyl)-1-methyldihydrouracil | 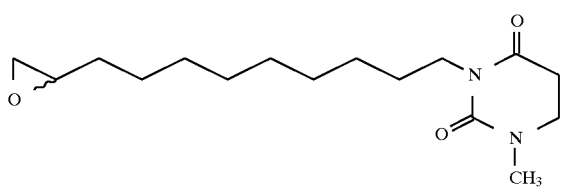 |
| 1830 | 3-(11,10-Oxidoundecyl)-1-methyluracil | 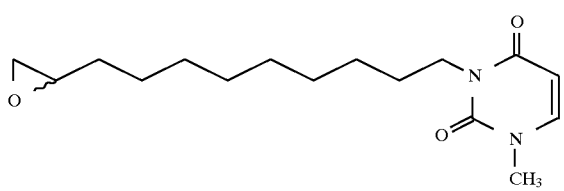 |
| 1906 | 3-(5,6-Oxidohexyl)-1-methylthymine | 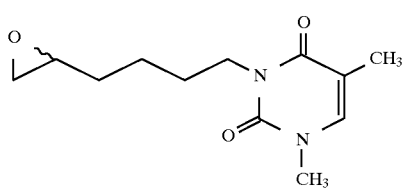 |
| 1910 | 3-(8,9-Oxidononyl)-1-methylthymine | 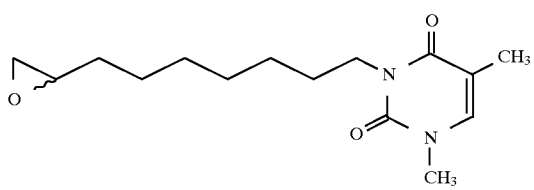 |
| 1932 | 3-(11,10-Oxidoundecyl)-1-methylthymine | 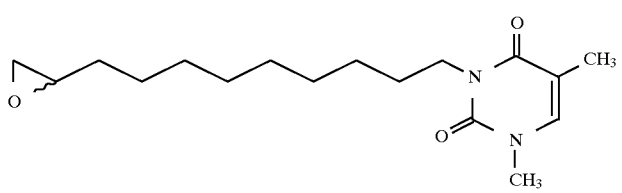 |

-continued
| | | |
|---|---|---|
| 2513 | 1-(3,4-Oxidobutyl)-3,7-dimethylxanthine | 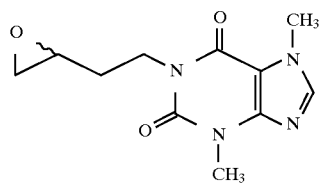 |
| 2518 | 1-(11,12-Oxidodecyl)-3,7-dimethylxanthine | 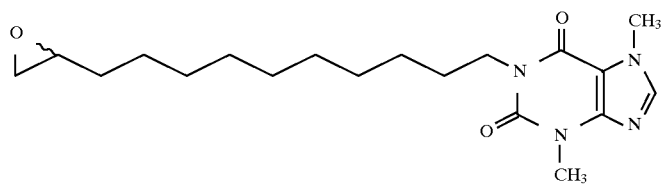 |
| 2541 | 1-(9,10-Oxidooctadecyl)-3,7-dimethylxanthine | 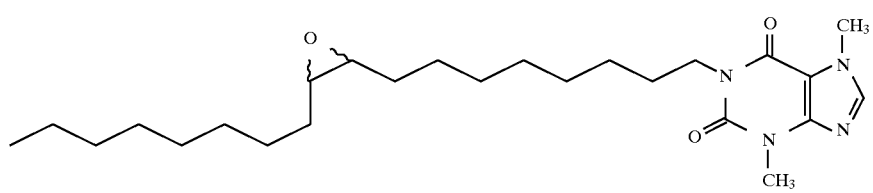 |
| 2548 (R) | 1-(4-(R)-Methyl-7,8-oxido-8-methylnonyl)-3,7-dimethylxanthine | 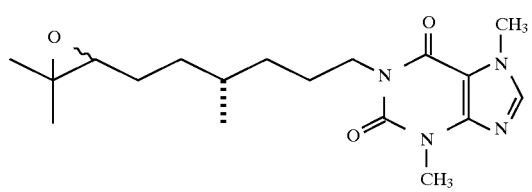 |
| 2548 (S) | 1-(4-(S)-Methyl-7,8-oxide-8-methylnonyl)-3,7-dimethylxanthine | 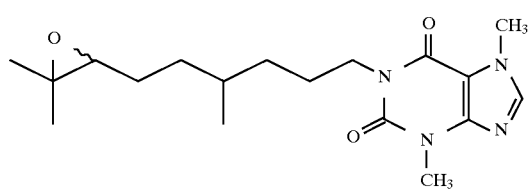 |
| 2552 | 1-(3,7-dimethyl-2,3,6,7-dioxidooctyl)-3,7-dimethylxanthine | 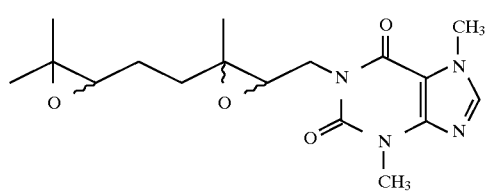 |
| 2562 | 1-(12,13-Oxidotridecyl)-3,7-dimethylxanthine | 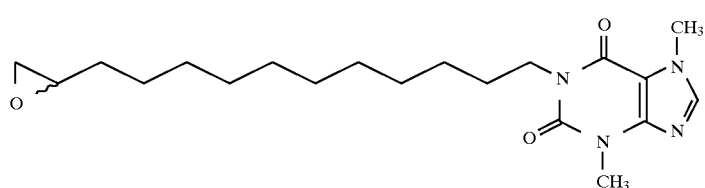 |
| 2563 | 1-(7,8-cis-Oxidodecyl)-3,7-dimethylxanthine | 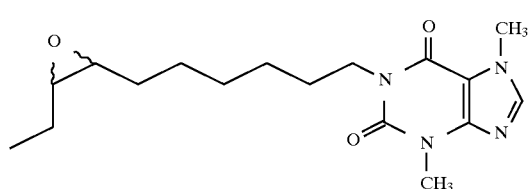 |

| | | |
|---|---|---|
| 3503 | 1-(13,14-Oxidotetradecyl)-3,7-dimethylxanthine | 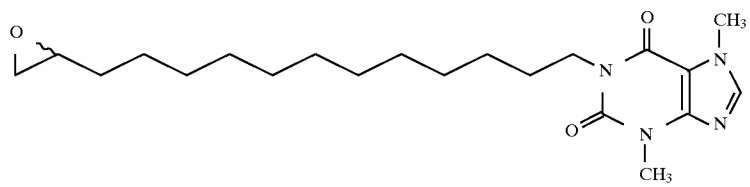 |
| 3516 | 1-(16,17-Oxidoheptadecyl)-3,7-dimethylxanthine | 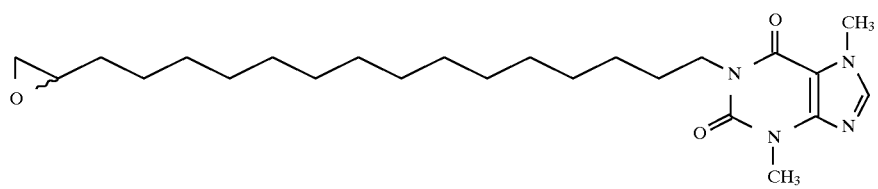 |

Uses of the Inventive Compounds and Pharmaceutical Formulations

The compounds of the invention provide a mechanism to maintain homeostasis in cells contacted by primary stimuli through mitigating the effects of these primary stimuli on the secondary signaling pathways invoked within seconds of the primary stimulus.

The foregoing in vitro effects give rise to inventive pharmaceutical compositions comprising an effective amount of at least one of the inventive compounds or a pharmaceutically acceptable salt, hydrate or solvate thereof and at least one pharmaceutically acceptable excipient or carrier. Because the inventive compounds, inter alia, inhibit cellular signaling, mediated for example by the IL-1 Type I receptor and are IL-1 antagonists, the inventive pharmaceutical compositions are useful for: 1) protecting and treating endotoxic shock and sepsis induced by gram positive or negative bacteria; 2) inhibiting, treating or preventing tumor cell growth, such as cancer; 3) stimulating hematopoiesis inhibited by cytoreductive therapies (e.g., chemotherapy or radiotherapy); 4) treating or preventing autoimmune diseases, such as insulin dependent diabetes mellitus (IDDM), arthritis (including rheumatoid arthritis), multiple schlerosis, Alzheimers disease, glomerular nephritis, Graves disease, and atheroschlerosis; 5) treating or preventing male pattern baldness by stimulation of hair growth through reversal of an apoptotic process; 6) preventing hair loss caused by cytoreductive therapies; 7) preventing the symptoms of ARDS (acute respiratory distress syndrome) caused by trauma; 8) treating or preventing asthma, inflammatory bowel disease, acute and myelogenous leukemia, transplant rejection, psoriasis, osteoporosis, periodontal disease, autoimmune thyroiditis, alcoholic hepatitis, premature labor secondary to uterine infection and even sleep disorders; and 9) preventing synergistic immunosuppression in GVHD (graft versus host disease).

Excessive or unregulated TNF (tumor necrosis factor) production may play a role in mediating or exacerbating a number of diseases including rheumatoid arthritis, rheumatoid spondylitis, osteoarthritis, gouty arthritis and other arthritic conditions, sepsis, septic shock, endotoxic shock, gram negative sepsis, toxic shock syndrome, adult respiratory distress syndrome, cerebral malaria, chronic pulmonary inflammatory disease, silicosis, pulmonary sarcoidosis, bone resorption diseases, reperfusion injury, graft versus host reaction, allograft rejections, fever, myalgias due to infection such as influenza, cachexia secondary to infection, AIDS or malignancy, AIDS, other viral infections (e.g., CMV, influenza, adenovirus, herpes family), keloid formation, scar tissue formation, Crohn's disease, ulcerative colitis, or pyresis. The inventive compounds or pharmaceutically acceptable salts thereof can be used in the manufacture of a medicament for the prophylactic or therapeutic treatment of any disease state in a human or other mammal, which is exacerbated or signaled 1) through the specific phospholipid-based messenger pathway that amplifies signals within a cell, and 2) by excessive or unregulated production of messenger inflammatory cytokines such as TNF or IL-1. With regard to TNF messenger signaling, there are several disease states in which excessive or unregulated monocyte/macrophage TNF production exacerbates or causes the disease. These include, for example, neurodegenerative diseases such as Alzheimers disease, endotoxemia or toxic shock syndrome (Tracey et al., Nature 330:662, 1987 and Hinshaw et al., Circ. Shock 30:279, 1990); cachexia (Dezube et al., Lancet 355:662, 1990), and adult respiratory distress syndrome (Miller et al., Lancet 2(8665):712, 1989). The inventive compounds may be used topically in the treatment of prophylaxis of topical disease states mediated or exacerbated by excessive TNF or IL-1, such as viral infections (herpes or viral conjunctivitis), psoriasis, fungal or yeast infections (ringworm, athletes foot, vaginitis, dandruff, etc.) or other dermatologic hyperproliferative disorders. High TNF levels have been implicated in acute malaria attacks (Grau et al., N. Engl. J. Med. 320:1585, 1989), chronic pulmonary inflammatory diseases such as silicosis and asbestosis (Piguet et al., Nature 344:245, 1990, and Bissonnette et al., Inflammation 13:329, 1989), and reperfusion injury (Vedder et al., Proc. Natl. Acad. Sci. USA 87:2643, 1990). Therfore, the inventive compounds may preferably be used to stimulate hematopoiesis, prevent and treat septic shock, treat acute and chronic inflammatory disease, treat or prevent an autoimmune disease, treat a fungal or yeast infection, and stimulate hair growth (when applied topically, as confirmed in in vivo results on nude mice).

The inventive compounds are useful as an adjuvant to inhibit toxic side effects of drugs. These side effects include, for example, side effects of: 1) interleukin-2 (IL-2); 2) cyclosporin A and FK506; and 3) amphotericin B. The inventive compounds also inhibit antigen-induced T cell activation, like cyclosporin or FK506, but, unlike cyclosporin or FK506, do not: 1) prevent generation of NK and LAK cells; 2) suppress IL-2 release from T cells; or 3) suppress IL-8 release.

Metalloproteases mediate tissue damage such as glomerular diseases of the kidney, joint destruction in arthritis, and lung destruction in emphysema, and play a role in tumor metastases. Three examples of metalloproteases include a 92 kD type V gelatinase induced by TNF, IL-1 and PDGF plus bFGF, a 72 kD type IV collagenase that is usually constitutive and induced by TNF or IL-1, and a stromelysin/PUMP-1 induced by TNF and IL-1. The inventive compounds can inhibit TNF or IL-1 induction of the 92 kD type V gelatinase inducable metalloprotease. Moreover, the inventive compounds can reduce PUMP-1 activity induced by 100 U/ml of IL-1. Accordingly, the inventive compounds prevent induction of certain metalloproteases induced by IL-1 or TNF and are not involved with constitutively produced proteases (e.g., 72 kD type IV collagenase) involved in normal tissue remodeling.

For example, the compounds of the invention are used in connection with patients undergoing bone marrow transplantation (BMT), regardless of whether the BMT is matched allogeneic, mismatched allogeneic, or autologous. Patients receiving autologous transplants are aided by treatment with compounds of the invention even though they do not necessarily need to be administered immunosuppressive agents, since they do not develop graft-versus-host disease (GVHD). However, the toxic effect of the chemotherapy or radiation therapy used in connection with the disease, in response to which the transplantation has been performed, constitutes a negative stimulus with regard to the patients' cells.

In general, all patients undergoing BMT require doses of chemotherapy with or without total body irradiation that exceed the lethal dose for normal bone marrow recovery. This provides the rationale for using either stored patient marrow or donor marrow to rescue the patient. In general, chemotherapy and radiation are delivered to the patient for 7–10 consecutive days before the new or stored bone marrow is infused. The day on which the marrow is given to the patient is referred to as day 0 of the transplant. Previous days on which the patient received chemo/radiation are designated by negative numbers. Subsequent days are referred to by positive numerals. The median time in which negative responses in BMT recipients occurs is within the first 100 days after transplant. Therefore, statistically, if patients survive through day 100, their chances for continued survival are significantly enhanced. The inventive compounds are able to increase the percentage of patients who survive. The percentage of fatalities within the first 100 days that is considered acceptable is 15–20% for "good risk" patients and 30–40% for "high risk". These fatalities are due to the direct effects of high doses of chemo/radiation. In addition, GVHD contributes to the death rate in allogeneic marrow recipients.

Other indications for which it is useful to administer the compounds of the invention include the presence of a tumor burden, a hormone-related disorder, a neurological disorder, an autoimmune disease, inflammation, restenosis, hypertension, unwanted immune response, viral infection, nephritis, mucositis, and various allergic responses. Prevention of allergic responses include prevention of acute allergic response and thus moderation or prevention of rhinorrhea, serious drainage, diffuse tissue edema, and generalized pruritus. Other symptoms of chronic allergic response include, as well as the foregoing, dizziness, diarrhea, tissue hyperemia, and lacrimal swelling with localized lymphocyte infiltration. Allergic reactions are also associated with leukotriene release and the distal effects thereof, including asthmatic symptoms including development of airway obstruction, a decrease in FEV 1, changes in vital capacity, and extensive mucus production.

Other suitable subjects for the administration of compounds of the invention, include patients being administered toxic agents for the treatment of tumors, such as chemotherapeutic agents or irradiation therapy, as well as treatment with biological response modifiers such as IL-2 and tumor suppressing cells such as lymphokine activated killer cells (LAK) and tumor-infiltrating lymphocytes (TIL cells); patients suffering from neoplasias generally, whether or not otherwise treated including acute and chronic myelogenous leukemia, hairy cell leukemia, lymphomas, megakaryocytic leukemia, and the like; disease states caused by bacterial, fungal, protozoal, or viral infection; patients exhibiting unwanted smooth muscle cell proliferation in the form of, for example, restenosis, such as patients undergoing cardiac surgery; patients who are afflicted with autoimmune diseases, thus requiring deactivation of T and B cells, and patients who have neurological disorders.

The compounds of the invention further are able to decrease the enhanced levels of a relevant PA and DAG resulting from stimulation of synaptosomes with acetylcholine and/or epinephrine. This suggests that the effects of the compounds of the invention are to both enhance the release of inhibitory neural transmitters such as dopamine, and to modulate the distal "slow current" effects of such neurotransmitters.

Thus, the drugs of the invention are also useful to raise the seizure threshold, to stabilize synapses against neurotoxins such as strichnine, to potentiate the effect of anti-Parkinson drugs such as L-dopa, to potentiate the effects of soporific compounds, to relieve motion disorders resulting from administration of tranquilizers, and to diminish or prevent neuron overfiring associated with progressive neural death following cerebral vascular events such as stroke. In addition, the compounds of the invention are useful in the treatment of norepinephrine-deficient depression and depressions associated with the release of endogenous glucocorticoids, to prevent the toxicity to the central nervous system of dexamethasone or methylprednisolone, and to treat chronic pain without addiction to the drug. Further, the compounds of the invention are useful in the treatment of children with learning and attention deficits and generally improve memory in subjects with organic deficits, including Alzheimer's patients.

While dosage values will vary, therapeutic efficacy is achieved when the compounds of the invention are administered to a human subject requiring such treatment as an effective oral, parenteral, or intravenous sublethal dose of about 200 mg to about 5000 mg per day, depending upon the weight of the patient. A particularly preferred regimen for use in treating leukemia is 4–50 mg/kg body weight. It is to be understood, however, that for any particular subject, specific dosage regimens should be adjusted to the individual's need and to the professional judgment of the person administering or supervising the administration of the inventive compounds.

Coadministration With a P-450 Inhibitor

The coadministration in vivo of the compounds of the invention along with an inhibitor of P-450 results in an enhanced effect due to a longer half life of the inventive compounds. This in vivo effect is due to inhibition of a degradation pathway for the compounds of the invention. For example, NIH3T3-D5C3 cells can be used to compare effects of an inventive compound alone or in combination with a P-450 inhibitor by comparing transformation phenotype control, incubation with an inventive compound, and coincubation of an inventive compound with the P-450 enzyme inhibitor.

Compounds that inhibit P-450 include, for example, (mg range daily dosage) propranolol (20–100), metaprolol (20–100); verapamil (100–400), diltiazem (100–400), nifedipine (60–100); cimetidine (400–2,400); ciprofloxacin (500–2000), enoxacin (500–2,000), norfloxacin (500–2000), ofloxacin (500–2,000), pefloxacin (500–2,000); erythromycin (100–1,000), troleandomycin (100–1,000); ketoconizole (100–2,000), thiabenzadole (100–1,000); isoniazid (100–1000); mexiletine (100–1,000); and dexamethasone (1–100 mg).

For combination therapy, the compounds of the invention and a P-450 inhibitor can be administered individually or in a single composition. A suitable formulation will depend on the nature of the disorder to be treated, the nature of the medicament chosen, and the judgment of the attending physician. In general, the inventive compounds are formulated either for injection or oral administration, although other modes of administration such as transmucosal or transdermal routes may be employed. Suitable formulations for these compounds can be found, for example, in *Remington's Pharmaceutical Sciences* (latest edition), Mack Publishing Company, Easton, Pa.

Depending on the inventive compound selected, the level of dosage can be appreciably diminished by coadministration of a P-450 inhibitor, such as a quinolone. Alternatively, a strong synergistic effect may be obtained with such a quinolone.

The invention, illustrated by the following examples, should not be deemed limited by these examples in any way. In these examples PTX means pentoxifylline.

EXAMPLE 1

This example illustrates a synthesis of N-(5,6-Oxidohexyl)phthalimide (inventive compound no. 1103). 1-bromo-5-hexene (6.52 g, 40 mmol) was added to a potassium phthalimide (7.4 g, 40 mmol) suspension in 50 mL of dimethyl sulfoxide and stirred overnight. After 12 hours of stirring at room temperature, the reaction was poured into a separatory funnel containing 300 mL of water and extracted with dichloromethane (5×200 mL). The organic extracts were combined, washed with water (100 mL) and brine (100 mL), dried over anhydrous magnesium sulfate and concentrated under reduced pressure. The crude product obtained was further purified by flash chromatography over silica gel (eluant: 10% acetone/hexane) to yield 9.2 g (100% yield) of N-(5-Hexenyl)phthalimide (inventive compound no. 1101).

A solution of N-(5-Hexenyl)phthalimide (1.145 g, 5 mmol), prepared as described above, and m-chloroperoxybenzoic acid (2.58 g, 7.5 mmol, 50% by wt) in dichloromethane (30 mL) was stirred for 5 hours. The reaction mixture was diluted with 80 mL of dichloromethane and washed successively with 20% aqueous sodium sulphite solution (20 mL), saturated sodium bicarbonate solution (20 mL), water and brine solutions. The organic layer was dried over anhydrous magnesium sulfate and concentrated under reduced pressure. The crude product obtained was further purified by flash chromatography over silica gel (using an eluant of 50% hexane and ethyl acetate) to yield 0.918 g (75% yield) of N-(5,6-Oxidohexyl)phthalimide.

EXAMPLE 2

This example illustrates a synthesis of N-(9,8-Oxidononyl)phthalimide (inventive compound no. 1105). 1-bromo-8-nonene (8.2 g, 40 mmol) was added to a suspension of potassium phthalimide (7.4 g, 40 mmol) in 50 mL of dimethyl sulfoxide and stirred overnight. After 12 hours of stirring at room temperature, the reaction product was poured into a separatory funnel containing 300 mL of water and extracted with dichloromethane (5×200 mL). Organic extracts were combined, washed with water (100 mL) and brine (100 mL), dried over anhydrous magnesium sulfate and concentrated under reduced pressure. The crude product obtained was further purified by flash chromatography over silica gel (using an eluant of 10% acetone/hexane) to yield 7.6 g (70.4% yield) of N-(8-Nonenyl)phthalimide (inventive compound no. 1101).

A solution of N-(8-Nonenyl)phthalimide (1.355 g, 5 mmol), prepared in accordance with the above process, and m-chloroperoxybenzoic acid (2.58 g, 7.5 mmol, 50% by wt) in dichloromethane (30 mL) was stirred for 5 hours. The reaction mixture was diluted with 80 mL of dichloromethane and washed successively with 20% aqueous sodium sulphite solution (20 mL), saturated sodium bicarbonate solution (20 mL), water and brine solutions. The organic layer was dried over anhydrous magnesium sulfate and concentrated under reduced pressure. The crude product obtained was further purified by flash chromatography over silica gel (using an eluant of 50% hexane/ethyl acetate), yielding 1.03 g (70% yield) N-(9,8-Oxidononyl)phthalimide.

EXAMPLE 3

This example illustrates a synthesis of N-(10,11-Oxidoundecyl)phthalimide (inventive compound no. 1109). To a suspension of potassium phthalimide (4.17 g, 22.5 mmol) in dimethylsulfoxide (30 mL) was added 11-undecenyl bromide (available through MTM) (5.0 g, 21.5 mmol) and the reaction mixture stirred for 16 hours at 60° C. The mixture was then poured into water (80 mL) and extracted with ethyl acetate (3×70 mL). The combined extracted organic portions were washed with water (3×100 mL), dried with magnesium sulfate and evaporated, resulting in a cream-colored solid. Purification by column chromatography (using ethyl acetate/hexane) yielded (5.50 g, 86%) N-(10-Undecenyl)phthalimide (inventive compound no. 1107) as a white solid.

A solution of N-(10-Undecenyl)phthalimide (4.97 g, 16.6 mmol), prepared as discribed above, 4-methylmorpholine-N-oxide (8.62 mL, 60% by wt in water, 50.0 mmol) and potassium osmate dihydrate (58 mg, 0.16 mmol) in 100 mL acetone/water (1:1 by wt) was stirred for 16 hours. Water (100 mL) and sodium sulfite (10 g) were added and the resulting solution stirred for an additional hour. The resulting reaction mixture was extracted with dichloromethane (3×80 mL) and the organic phase dried using magnesium sulfate and evaporated to obtain 3.93 g (71% yield) of N-(10,11-Dihydroxyundecyl)phthalimide (inventive compound no. 1108).

N-(10,11-Dihydroxyundecyl)phthalimide (2.35 g, 7.10 mmol) was stirred for 3 hours with HBr (6.90 mL of a 30% solution in acetic acid, 21.3 mmol). The mixture was then added over 10 minutes to a solution of water (50 mL), ice (25 g) and $NaHCO_3$ (15 g) and stirred for an additional 30 min. The resulting reaction product was extracted with dichloromethane (3×70 mL) and the combined organic phase was dried using magnesium sulfate and evaporated, yielding a residue of N-(10-acetoxy-11-bromoundecyl) phthalimide.

Without further purification, this crude product was treated in methanol (10 mL) with a solution of sodium methoxide (prepared from sodium—0.23 g, 10.0 mmol—and 10 mL methanol). After 60 minutes the reaction mixture containing treated crude product was added to water (30 mL) and extracted with dichloromethane (100 mL, 2×50 mL). The extracted organic portions were combined, dried and evaporated, yielding 2.00 g (89% yield) N-(10,11-Oxidoundecyl)phthalimide (inventive compound no. 1109) as a white solid.

EXAMPLE 4

This example illustrates a synthesis of N-(10,11-Oxidoundecyl)homophthalimide (inventive compound no. 1114). A mixture of homophthalic acid (54.0 g; 0.3 mole) and finely powdered urea (19.82 g; 0.33 mole) were heated to 175–185° C. until no more ammonia evolves, evidenced by pH paper. The crude product was refluxed with methanol (500 mL) and homophthalimide isolated by filteration (29 g; 60%). Sodium hydride(95%) (576 mg, 24 mmol) was added to a solution of homophthalimide (3.2 g, 20 mmol) in anhydrous dimethylsulfoxide (75 mL). After 20 minutes of stirring, 1-bromoundec-10-ene (5.6 g, 24 mmol) was added. After 16 hours of stirring at room temperature, the reaction mixture was poured into a separatory funnel containing 500 mL of water and extracted with ethyl acetate (3×100 mL). The organic extracts were combined, washed with water (100 mL) and brine (100 mL), dried over anhydrous magnesium sulfate and concentrated under reduced pressure. The crude product obtained was further purified by flash chromatography over silica gel using petroleum ether/5% ethyl acetate eluant to yield 2.2 g (35.5% yield) N-(10-Undecenyl)homophthalimide.

A solution of olefin N-(10-Undecenyl)homophthalimide (1.4 g, 4.5 mmol), and m-chloroperoxybenzoic acid (2.3 g, 6.7 mmol) (50% by wt) in dichloromethane (50 mL) was stirred for 5 hours. The reaction mixture was diluted with 80 mL of dichloromethane and washed successively with 20% aqueous sodium sulphite solution (20 mL), saturated sodium bicarbonate solution (20 mL), water (50 mL) and brine solutions (50 mL). The organic layer was dried over anhydrous magnesium sulfate and concentrated under reduced pressure. The crude product obtained was further purified by flash chromatography over silica gel using 75% hexane/ethyl acetate eluant to yield 1.38 g (94% yield) N-(10,11-Oxidoundecyl)homophthalimide.

EXAMPLE 5

This example illustrates a synthesis of 1-(5,6-Oxidohexyl)-3-methylbenzoyleneurea (inventive compound no. 1206). Sodium metal (0.071 g, 3.1 mmol) was dissolved in methanol (3.1 mL) to prepare a 1.0 molar solution of sodium methoxide. 1-(5-Acetoxy-6-bromohexyl)-3-methylbenzoylene (1.17 g, 2.9 mmol) was dissolved into methanol (25 mL) and added to the sodium methoxide solution over 5 minutes. After stirring for 1 hour, 50 mL of water were added to the solution. The acqueous phase was extracted using three 25 mL aliquots of dichloromethane. The organic phase was dried over sodium sulfate, filtered and the solvent removed under vacuum yielding 0.77 g (97% yield) of white, solid 1-(5,6-Oxidohexyl)-3-methylbenzoyleneurea).

EXAMPLE 6

This example illustrates a synthesis of 3-Methyl-7-methylpivaloyl-1-(8,9-oxidononyl)xanthine (inventive compound no. 1409). A mixture of 3-methylxanthine (Aldrich, 1.00 g, 6.0 mmol), sodium hydride (145 mg, 6.0 mmol) and dimethyl sulfoxide (20 mL) was stirred until homogeneous (0.5 hours). Chloromethylpivalate (865mL, 904 mg, 6.0 mmol) was added and the reaction stirred for 18 hours. The reaction mixture was poured into water (70 mL) and then extracted with 25% ethanol/dichloromethane (4×60 mL). The combined organic extracts were dried over sodium sulfate and evaporated under vacuum to a volume of 40 mL. This solution was cooled in icewater, whereupon a thick white precipitate was formed. The solid was filtered off under suction and dried under vacuum to yield 1.43 g (90% yield) 3-methyl-7-(methylpivaloyl)xanthine (inventive compound no. 1404).

A mixture of 3-methyl-7-(methylpivalyl)xanthine (2.14 g, 7.6 mmol) and sodium hydride (183 mg, 7.6 mmol) in dimethyl sulfoxide (30 mL) were stirred for 15 minutes, after which period, 9-bromo-1-nonene (1.56 g, 7.6 mmol) was added. After stirring at ambient temperature for 2 days, the reaction mixture was poured into water (50 mL) and extracted with dichloromethane (3×50 mL). The combined organic portions were washed with water (2×20 mL) and saturated aqueous sodium chloride solution (30 mL). The solvent was removed under vacuum to give a thick oil. Chromatography (silica, ethyl acetate/20% hexane) of this residue yields 1.46 g (48% yield) of a white, solid, 3-methyl-7-methylpivaloyl-1-(8-nonenyl)xanthine (inventive compound no. 1411).

A mixture of 3-methyl-7-methylpivaloyl-1-(8-nonenyl) xanthine (910 mg, 2.3 mmol), 3-chloroperbenzoic acid (1.16 g of a 50% mixture, 3.4 mmol), and sodium bicarbonate (857 mg, 10 mmol) in dichloromethane (15 ml) and water (10 mL) was stirred for 18 hours at ambient temperature. A saturated aqueous solution of sodium bisulfite was added (15 mL) and stirring is continued for 30 minutes. The layers are separated and the aqueous layer extracted with dichloromethane (3×30 mL). The combined organic layers were combined and washed with saturated aqueous sodium bicarbonate solution (20 mL), water (20 mL) and saturated aqueous sodium chloride solution (20 mL) and then dried over sodium sulfate. Solvent was evaporated under vacuum. Chromotography of this residue using silica and a dichloromethane/5% ethanol eluant yielded 660 mg (68% yield) 3-methyl-7-methylpivaloyl-1-(8,9-oxidononyl) xanthine (inventive compound no. 1409).

EXAMPLE 7

This example illustrates a synthesis of 1-(8,9-Oxidohexyl)-3-methyl-7-methylpivaloylxanthine (inventive compound no. 1410). A mixture of 3-methylxanthine (Aldrich, 1.00 g, 6.0 mmol), sodium hydride (145 mg, 6.0 mmol) and dimethyl sulfoxide (20 mL) was stirred until homogeneous (0.5 hours). Chloromethylpivalate (865 mL, 904 mg, 6.0 mmol) was added and the reaction stirred for 18 hours. The reaction mixture was poured into water (70 mL) and then extracted with 25% ethanol/dichloromethane (4×60 mL). The combined organic extracts were dried over sodium sulfate and evaporated under vacuum to a volume of 40 mL. This solution was cooled in icewater, whereupon a thick white precipitate formed. The solid was filtered off under suction and dried under vacuum to yield 1.43 g (90% yield) 3-methyl-7-(methylpivaloyl)xanthine (inventive compound no. 1404).

Sodium hydride (86 mg, 3.6 mmol) was added to a stirring solution of 3-methyl-7-(methylpivaloyl)xanthine 1404 (1.00 g, 3.6 mmol) in dimethyl sulfoxide (25 mL). After 15 minutes, 6-bromo-1-hexene (589 mg, 3.6 mmol) was added and stirring continued for 72 hours. The reaction mixture was then poured into water (70 mL) and extracted with dichloromethane (2×100 mL) and 20% ethanol/ dichloromethane (1×100 mL). The combined organic layers were washed with saturated aqueous sodium chloride solution (50 mL) and dried over magnesium sulfate. The solvent was evaporated under vacuum to give a thick oil. Chromotograpy of the resulting thick oil using silica and ethyl acetate yielded 870 mg (67% yield) 1-(5-hexenyl)-3-methyl-7-(methylpivaloyl)xanthine (inventive compound no. 1441)

A mixture of 1-(5-hexenyl)-3-methyl-7-(methylpivaloyl) xanthine (440 mg, 1.2 mmol) and m-chloroperoxybenzoic acid (828 mg of 50% m-chloroperoxybenzoic by wt, 2.4 mmol) in dichloromethane (10 mL) and sodium bicarbonate (807 mg, 9.2 mmol) in water (10 mL) was stirred for 20 hours. Sodium metabisulfite (1.0 g, 5.3 mmol) was added. After 30 minutes, the reaction mixture was extracted with dichloromethane (3×10 mL). The combined organic portions were washed with saturated aqueous sodium bicarbonate solution (10 mL) and the solvent was evaporated under vacuum. Chromatography of the residue on silica using 10% pet ether/ethyl acetate eluant yielded 146 mg (32% yield) 1-methyl-7-(methylpivaloyl)-3-(5,6-oxidohexyl)xanthine (inventive compound no. 1410).

EXAMPLE 8

This example illustrates a synthesis of 1-(11,10-Oxidoundecanyl)-3-methyl-7-methylpivalylxanthine (inventive compound no. 1412). A mixture of 3-methylxanthine (Aldrich, 1.00 g, 6.0 mmol), sodium hydride (145 mg, 6.0 mmol) and dimethyl sulfoxide (20 mL) was stirred until homogeneous (0.5 hours). Chloromethylpivalate (865 mL, 904 mg, 6.0 mmol) was added and the reaction stirred for 18 hours. The reaction mixture was poured into water (70 mL) and then extracted with 25% ethano/dichloromethane (4×60 mL). The combined organic extracts were dried over sodium sulfate and evaporated under vacuum to a volume of 40 mL. This solution was cooled in icewater, whereupon a thick white precipitate formed. The solid was filtered off under suction and dried under vacuum to yield 1.43 g (90% yield) 3-methyl-7-(methylpivaloyl)xanthine (inventive compound no. 1404).

Sodium hydride (76.8 mg, 3.2 mmol) was added to a solution of 3-methyl-7-pivaloylxanthine (0.84 g; 3 mmol) and 11-bromoundec-10-ene (0.745 g; 3.2 mmol) in 15 mL of dimethyl sulfoxide and stirred overnight. After 12hours of stirring at room temperature, the reaction was poured into a separatory funnel containing 30 mL of water and extracted with dichloromethane (5×50 mL). The organic extracts were combined, washed with water (30 mL) and saturated aqueous sodium chloride solution (30 mL), dried over anhydrous magnesium sulfate and concentrated under reduced pressure. The crude product obtained was further purified by flash chromatography over silica gel using 50% hexane/ ethyl acetate eluant to yield 1.05 g (73.8% yield) 1-(10-undecenyl)-7-methylpivaloyl-3-methylxanthine (inventive compound no. 1403).

A solution of 1-(10-undecenyl)-7-methylpivaloyl-3-methylxanthine (0.60 g, 1.39 mmol), and m-chloroperoxybenzoic acid (0.359 g; 2 mmol, 50% by wt) in dichloromethane (10 mL) was stirred for 5 hours. The reaction mixture was diluted with 40 mL of dichloromethane and washed successively with 20% aqueous sodium sulphite solution(20 mL), saturated sodium bicarbonate solution (20 mL), water and saturated aqueous sodium chloride solution. The organic layer was dried over anhydrous magnesium sulfate and concentrated under reduced pressure. The crude product obtained was further purified by flash chromatography over silica gel using 50% hexane and ethyl acetate eluant, yielding 0.443 g (72% yield) 1-(11,10-Oxidoundecanyl)-3-methyl-7-methylpivalylxanthine.

EXAMPLE 9

This example illustrates a synthesis of 1-(11,10-Oxidoundecanyl)-3-methylxanthine (inventive compound no. 1413). A solution of 1-(11,10-Oxidoundecanyl)-3-methyl-7-methylpivalylxanthine (inventive compound no. 1412), prepared as described above (104 mg; 0.23 mmol), was added to a solution of sodium methoxide (15.1 mg; 0.28 mmol) in 3 mL of methanol and stirred for 4 hours. The reaction mixture was quenched with saturated ammonium chloride solution (5 mL) and extracted with 20% ethanol/ dichloromethane (3×30 mL). The combined organic extract was dried over anhydrous magnesium sulfate and concentrated under reduced pressure. The crude product obtained was further purified by flash chromatography over silica gel using 10% methanol/ethyl acetate eluant to yield 75 mg (96.7%) of (11,10-Oxidoundecanyl)-3-methylxanthine (inventive compound no. 1413).

EXAMPLE 10

This example illustrates a synthesis of 7-(11,10-Oxidondecyl)-1,3-dimethylxanthine (inventive compound no. -1423). Sodium hydride(95%) (0.575 g, 24 mmol) was added to a solution of theophylline (3.6 g, 20 mmol) in dimethylsulfoxide (100 mL). After 20 minutes of stirring, 1-bromoundec-10-ene (4.66 g, 20 mmol) was added and stirred for 12 hours at room temperature. The reaction mixture was then poured into a separatory funnel containing water (300 mL) and extracted with dichloromethane (5×100 mL). The organic extracts were combined, washed with water (100 mL) and brine (100 mL), dried over anhydrous magnesium sulfate and concentrated under reduced pressure. The crude product obtained was further purified by flash chromatography over silica gel using 50% hexane/ ethyl acetate eluant, yielding 6.26 g (94% yield) of 7-(10-undecenyl)-1,3-dimethylxanthine (inventive compound no. 1420).

A solution of 7-(10-undecenyl)-1,3-dimethylxanthine (4.98 g, 15 mmol) and m-chloroperoxybenzoic acid (7.704 g; 22.5 mmol) (50% by wt) in dichloromethane (100 mL) was stirred for 5 hours. The reaction mixture was diluted with 80 mL of dichloromethane and washed successively with 20% aqueous sodium sulphite solution (100 mL), saturated sodium bicarbonate solution (100 mL), water (100 mL) and brine solution (100 mL). The organic layer was dried over anhydrous magnesium sulfate and concentrated under reduced pressure. The crude product obtained was further purified by flash chromatography over silica gel using 50% petroleum ether/ethyl acetate eluant to yield 3.13 g (60% yield) of 7-(11,10-Oxidondecyl)-1,3-dimethylxanthine.

EXAMPLE 11

This example illustrates a synthesis of 7-(11,10-Oxidondecyl)-1-methyl-2,4-dioxotetrahydropteridine (inventive compound no. 1426). 1-Methyl-4,5-diaminouracil (13.6 g; 59.4 mole) was suspended in water (150 mL) and converted to its hydrochloride by drop-wise addition of concentrated hydrochloric acid unitl the solution is strongly acidic. Glyoxan sodiumbisulphite (20.4 g; 71.8 mmol) was then added and the reaction mixture refluxed for 30 minutes. The reaction mixture was cooled to room temperature and the precipitated 1-methyl-2,4-dioxotetrahydropteridine isolated by filteration, yielding 6.5 g (62%). Sodium hydride (95%,) (0.575 g, 24 mmol) was added to a solution of 1-methyl-2,4-dioxotetrahydropteridine (3.56 g, 20 mmol) in dimethylsulfoxide (100 mL). After 20 minutes of stirring, 1-bromoundec-10-ene (4.66 g, 20 mmol) was added and stirred for 12 hours at room temperature. The reaction mixture was then poured into a separatory funnel containing water (300 mL) and extracted with ethyl acetate (5×100 mL). The organic extracts were combined, washed with water (100 mL) and brine (100 mL), dried over anhydrous magnesium sulfate and concentrated under reduced pressure. The crude product obtained was further purified by flash chromatography over silica gel using 50% hexane/ethyl acetate eluant to yield 5 g (94% yield) of 3-(10-undecenyl)-1-methyl-2,4-dioxotetrahydropteridine (inventive compound no. 1421). A solution of 3-(10-undecenyl)-1-methyl-2,4-dioxotetrahydropteridine (3.3 g, 10 mmol) and m-chloroperoxybenzoic acid (5.13 g; 15 mmol) (50% by wt) in dichloromethane (50 mL) was stirred for 5 hours. The reaction mixture was diluted with 40 mL of dichloromethane and washed successively with 20% aqueous sodium sulphite solution (20 mL), saturated sodium bicarbonate solution (20 mL), water (30 mL) and brine solutions (30 mL). The organic layer was dried over anhydrous magnesium sulfate and concentrated under reduced pressure. The crude product obtained was further purified by flash chromatography over silica gel using 40% petroleum ether/ethyl acetate eluant to yield 2.61 g (75% yield) of 7-(11,10-Oxidondecyl)-1-methyl-2,4-dioxotetrahydropteridine.

EXAMPLE 12

This example illustrates a synthesis of 1-Methyl-3-(5,6-oxidohexyl)xanthine (inventive compound no. 1439). A solution of 1-methyl-7-(methylpivaloyl)-3-(5,6-oxidohexyl)xanthine, prepared as described above, (120 mg, 0.3 mmol) in methanol (5 mL) was treated with a 1M methanol solution of sodium methoxide (0.33 mL). After 15 minutes of stirring, water (5 mL) was added and the reaction product was extracted with 25% ethanol/dichloromethane (4×25 mL). The aqueous layer was evaporated under vacuum leaving a solid residue which is subsequently washed with dichloromethane (4×20 mL). The combined organic washings were evaporated under vacuum to a give a solid, yellowish residue. Chromatography of the residue using silica and 50% ethyl acetate/methanol yields 55 mg (69% yield) of solid 1-methyl-3-(5,6-oxidohexyl)xanthine.

EXAMPLE 13

This example illustrates a synthesis of 1-(6,7-cis-Oxidononyl)-3,7-dimethylxanthine (inventive compound no. 1509). A mixture of cis-6-nonen-1-ol (TCI, 3.00 g, 21.1 mmol) and methanesulfonyl chloride (1.6 mL, 2.4 g, 21 mmol) in dichloromethane (100 mL) at 0° C. was treated with triethylamine (4.4 mL, 3.2 g, 32 mmol). After 1 hour the ice bath was allowed to melt. After reaching ambient temperature, the reaction was poured into a separatory funnel containing water (50 mL) and dichloromethane (50 mL). The layers were separated and the aqueous layer washed with dichloromethane (2×50 mL). The combined organic layers were dried over sodium sulfate, and solvent removed to yield 4.14 g, 18.8 mmol (89% yield) 6-cis-nonene-1-methanesulfonate as a yellow oil.

Theobromine (3.36 g, 18.8 mmol) and sodium hydride (451 mg, 18.8 mmol) in dimethylsulfoxide (40 mL) was stirred for 40 minutes after which time the mesylate (4.14 g, 18.8 mmol) was added. The reaction was stirred at 25° C. for 3 days, then heated at 80° C. for 1 hour, and cooled. The reaction mixture was poured into water (100 mL) and extracted with dichloromethane (3×60 mL). The combined organic layers were washed with saturated aqueous salt solution (2×50 mL) and dried over sodium sulfate. The solvent was removed. Chromatography using silica and ethyl acetate of the residue yields 4.54 g (79% yield) 1-(6-cis-nonenyl)-3,7-dimethylxanthine (inventive compound no. 1508).

A mixture of 1-(6-cis-nonenyl)-3,7-dimethylxanthine, prepared as described above, in dichloromethane (10 mL) was stirred with sodium bicarbonate (2.62 g, 31 mmol) in water (20 mL) and 4-chloroperoxybenzoic acid (2.0 g, or 4.0 g of a 50% mixture) for 15 hours. Sodium sulfite (1.82 g, 14.5 mmol) was added, the mixture added to water (50 mL) and extracted with dichloromethane (2×50 mL). The combined organic layers were washed with water (40 mL) and saturated aqueous salt solution (40 mL). The solvent was removed to yield a yellow oily residue which was subsequently isolated using silica and ethyl acetate chromatography, yielding 520 mg (42% yield) of a white, solid 1-(6,7-cis-oxidononyl)-3,7-dimethylxanthine.

EXAMPLE 14

This example illustrates a synthesis of 1-(5,6-Oxidohexyl)-3,7-dimethylxanthine (inventive compound no. 1541). To a mixture of bromohexene (10.7 g, 66 mmol, Aldrich) and sodium hydride (1.58 g, 66 mmol) in dimethylsulfoxide (100 mL) was added theobromine (11.9 g, 66 mmol, available from Sigma) and stirred for 43 hours. The solution was treated with water (200 mL) and extracted with dichloromethane (3×80 mL). The combined extracts were washed with water (3×100 mL), dried over magnesium sulfate, and then the solvent evaporated under vacuum to yield 17 g (65 mmol, 98% yield) of a white powder, 1-(5-Hexenyl)-3,7-dimethylxanthine (inventive compound no. 1539).

To a mixture of 1-(5-Hexenyl)-3,7-dimethylxanthine (1.07 g, 4.1 mmol) and N-methylmorpholine-N-oxide (1.44 g, 12.3 mmol) in water (20 mL) and acetone (10 mL) was added 2.5% osmium tetraoxide in t-butanol (6 drops). After stirring for 48 hours, the mixture was treated with 20% aqueous sodium dithionite solution (20 mL). After 2 minutes, the mixture is extracted with 25% ethanol-dichloromethane solution (3×30 mL). The combined extracts were dried over magnesium sulfate and the solvents were evaporated under vacuum, yielding 750 mg, 2.53 mmol (62% yield) 1-(5,6-dihydroxyhexyl)-3,7-dimethylxanthine (inventive compound no. 1502) as a white powder.

To 1-(5,6-dihydroxyhexyl)-3,7-dimethylxanthine 1.0 g, 3.38mmol) was added 30% hydrogen bromide-acetic acid (3.4 mL) over 30 seconds and then stirred for 2.5 hours until all of the solid dissolved. The solution was poured carefully over a mixture of sodium bicarbonate (12 g) and ice water (50 mL). After carbon dioxide evolution had subsided, the mixture was extracted with dichloromethane (3×25 mL). The combined extracts were dried over magnesium sulfate and the solvent evaporated under vacuum, yielding 1.3 g (3.24 mmol, 96%) 1-(5-Acetoxy-6-bromohexyl)-3,7-dimethylxanthine as a viscous oil, dissolved in methanol (5 mL). A 1M sodium methoxide in methanol solution (3.9 mL) was added over 30 seconds. After stirring for 20 minutes, the solution was reated with water (20 mL) and then extracted with dichloromethane (3×15 mL). The combined extracts were dried over magnesium sulfate and the solvents were evaporated under vacuum to yield 900 mg (3.24 mmol, 100% yield) 1-(5,6-Oxidohexyl)-3,7-dimethylxanthine as white crystals.

EXAMPLE 15

This example illustrates a synthesis of 1-(8,9-Oxidooctyl)-3,7-dimethylxanthine (inventive compound no. 1553). To a suspension of sodium hydride (580 mg, 24.2 mmol ) in dimethylsulfoxide (100 mL) was added theobromine (3.96 g, 22.0 mmol). After 30 minutes, 8-bromo-1-octene (3.96 g, 22 mmol) was added and the reaction stirred 16 hours at 25° C. The mixture was then poured into water (200 mL) and extracted with dichloromethane (3×50 mL). The combined organic portions were washed with brine (50 mL) and dried over sodium sulfate. The solvent was evaporated under vacuum to yield 6.22 g (97% yield) of thick white oil, 1-(7-octenyl )-3,7-methylxanthine (inventive compound no. 1535) which solidified upon standing.

A solution of 1-(7-octenyl)-3,7-dimethylxanthine (1.00 g, 4.5 mmol), 4-methylmorpholine-N oxide (553 mg, 4.7 mmol), and a 2.5% solution of osmium tetroxide in t-butanol (3 drops) in acetone (25 mL) and water (20 mL) was stirred for 4 days. After addition of a saturated aqueous solution of sodium hydrosulfite (10 mL) and 30 minutes of continued stirring, the reaction mixture was added to water (50 mL) and extracted with 20% ethanol/dichloromethane (3×50 mL). Evaporation of the solvent under vacuum yielded an off-white residue. The residue was recrystallized in ethanol, yielding 726 mg (63% yield) 1-(7,8-dihydroxyoctyl)-3,7-dimethylxanthine (inventive compound no. 1538) as a white solid.

A mixture of 1-(7,8-dihydroxyoctyl)-3,7-dimethylxanthine, prepared as described above, (2.11 g, 6 mmol) was stirred with a 30% solution of hydrogen bromide in acetic acid (3.58 mL, 18 mmol) for 90 minutes. The mixture was then added to a flask containing aqueous sodium bicarbonate solution (4 g in 50 mL) and dichloromethane (30 mL). After 10 minutes of vigorous stirring the layers were separated and the aqueous portion was washed with dichloromethane (2×50 mL). The combined organic portions were dried over sodium sulfate and the solvent was evaporated under vacuum, yielding 2.51 g (94%) 1-(7-acetoxy-8-bromooctyl)-3,7-dimethylxanthine (inventive compound no. 1514) as a yellow oil.

A solution of 1-(7-acetoxy-8-bromooctyl)-3,7-dimethylxanthine in methanol (10 mL) was treated with a 1M solution of sodium methoxide (1.4 mL). After 30 minutes, the reaction was added to water (20 mL) and extracted with dichloromethane (2×30 mL). Combined organic portions are dried to give an off-white residue, recrystallized in dichloromethane/petroleum ether, yielding 1.42 g (75% yield) 1-(8,9-oxidooctyl)-3,7-dimethylxanthine (inventive compound no. 1553).

EXAMPLE 16

This example illustrates a synthesis of 1-(4,5-Oxohexyl)-3,7-dimethylxanthine (inventive compound no. 1555). To a solution of 4-hexen-1-ol (1.22 g, 12.2 mmol) and methane-sulfonyl chloride (1.04 mL, 13.4 mmol) in dichloromethane (15 mL), cooled in an ice bath, was added triethylamine (2.55 mL, 18.3 mmol) dropwise. After 5 minutes, the cooling bath was removed and the mixture stirred for an additional 45 minutes and then treated with saturated aqueous sodium bicarbonate solution (25 mL). The layers were separated and the aqueous layer extracted with dichloromethane (20 mL). The combined organic layers were dried over magnesium sulfate and the solvents evaporated under vacuum, yielding 1-methanesulfonyloxy-4-hexene as a viscous oil.

A mixture of theobromine (2.16 g, 12 mmol) and sodium hydride (288 mg, 12 mequivalents) in dimethylsufoxide (10 mL) was stirred for 30 minutes and then a solution of 1-methansulfonyloxy-4-hexene in dimethylsulfoxide (10 mL) was added. After 84 hours of stirring, water (70 mL) is added and the mixture extracted with ether (3×50 mL). The combined extracts were washed with water (50 mL) and dried over magnesium sulfate. The solvent was then evaporated under vacuum. The residue was purified by flash chromatography (22 g silica gel using an ethyl acetate eluant, 500 mL), yielding 2.1 g (67%) 1-(4-hexenyl)-3,7-dimethylxanthine. To a solution of 1-(4-hexenyl)-3,7-dimethylxanthine (270 mg, 1.03 mmol) in dichloromethane (10 mL) was added saturated aqueous sodium bicarbonate solution (10 mL), followed by a solution of 50–60% 3-chloroperoxybenzoic acid (889 mg, 2.58 mmol) in dichloromethane (5 mL) over 1 minute. After 20 hours of stirring, 20% aqueous sodium metabisulfite solution (15 mL) was added over 1 minute. The mixture was then extracted with dichloromethane (3×15 mL). The combined extracts were washed with saturated aqueous sodium bicarbonate solution (3×20 mL) and dried over magnesium sulfate. The sovent was evaporated under vacuum. The residue was purified by flash chromatography using 14 g of silica gel and eluting with ethyl acetate (100 ml) followed by 8% methanol-dichloromethane (60 mL), yielding 80 mg (28% yield) of 1-(4,5-oxohexyl)-3,7-dimethylxanthine as a white powder.

EXAMPLE 17

This example illustrates a synthesis of 1-(8,9-Oxidononyl)-3,7-dimethylxanthine (inventive compound no. 1560). A mixture of theobromine (17.64 g, 98 mmol) and sodium hydride (2.35 g, 98 mmol) in dimethylsulfoxide (250 mL) was stirred for 15 minutes. After addition of 9-bromo-1-nonene (Alfebro, 20.0 g, 98 mmol) stirring was continued at ambient temperature for 3 days. The reaction mixture was then poured into water (300 mL) and extracted with dichloromethane (4×200 mL). The combined organic layers are washed with saturated aqueous salt solution (2×150 mL) and dried over sodium sulfate. The solvent was evaporated under vacuum to give a thick oil. After cooling a solution of the oil in a minimum of dichloromethane and ether, 1-(8-nonenyl)-3,7-dimethylxanthine (inventive compound no. 1550) (24.34 g, 77.5 mmol, 99% yield) formed as white crystals.

A solution of 1-(8-nonenyl)-3,7-dimethylxanthine (810 mg, 2.7 mmol), 4-methylmorpholine-N- oxide (340 mg, 2.9 mmol) and 2.5% oxmium tetroxide in t-butanol (3 drops) in acetone (20 mL) and water (20 mL) was stirred for 24 hours. Saturated aqueous sodium dithionite solution (5 mL) was added. After stirring for 15 minutes, the reaction was extracted with 25% ethanol-dichloromethane (4×50 mL). The combined organic portions were dried over sodium sulfate, and the solvents were evaporated under vacuum. The solid residue was recrystallized (ethanol-chloroform), yielding 490 mg (54%) 1-(8,9-dihydroxynonyl)-3,7-dimethylxanthine (inventive compound no. 1561).

A mixture of 1-(8,9-dihydroxynonyl)-3,7-dimethylxanthine and 30% hydrogen bromide in acetic acid (0.8 mL, 3.90 mmol) was stirred for 90 minutes. The solution was poured into a mixture of water (10 mL), sodioum bicarbonate (1.35 g, and dichloromethane (10 mL). After 10 minutes of vigorous stiring, the layers were separated and the aqueous portion extracted with dichloromethane (3×15 mL). The combined organic phases were dried over sodium sulfate and the solvent evaporated under vacuum, yielding 550 mg (96%) 1-(8-acetoxy-9-bromononyl)-3,7-dimethylxanthine as a yellow oil. Without further purification, the oil was dissoved in methanol (5 mL) and then a 1M solution of sodium methoxide in methanol (1.4 mL) was added. After 30 minutes, the reaction mixture was poured into water (30 mL) and was extracted with dichloromethanone (3×40 mL). The combined organic portions were dried over sodium sulfate and the solvents evaporated under vacuum. The solid residue was recrystallized (dichloromethane-petroleum ether) to yield 380 mg (91% yield) 1-(8,9-oxidononyl)-3,7-dimethylxanthine (inventive compound no. 1560).

EXAMPLE 18

This example illustrates a synthesis of 1-(9,10-Oxidodecyl)-3,7-dimethylxanthine (inventive compound no. 1565). To a solution of 9-decene-1-ol (Aldrich, 3.00 g, 19.2 mmol) in dichioromethane (100 mL) at 0° C. was added methanesulfonyl chloride (2.20 g, 1.5 mL, 19.2 mmol), followed by triethylamine (2.91 g, 28.8 mmol). After stirring for 15 minutes at 0° C., the reaction was allowed to warm to room temperature. After 2 hours, the reaction mixture was poured into water (100 mL) and extracted with dichloromethane (3×60 mL). The combined organic portions were dried over sodium sulfate and the solvent was evaporated under vacuum yielding 4.52 g (100%) mesylate as a yellow oil. The mesylate was used without further purification.

To a suspension of sodium hydride (461 mg, 19.2 mmol) in dimethylsulfoxide (30 mL) was added theobromine (3.45 g, 19.2 mmol). After 15 minutes, the 9-decenylmesylate (2.25 g, 11 mmol) was added and the reaction stirred 18 hours at 25° C., then at 100° C. for 40 minutes. The mixture was then poured into water (100 mL) and extracted with dichloromethane (3×50 mL). The combined organic portions were washed with saturated salt solution (60 mL) and dried over magnesium sulfate. The solvent was evaporated under vacuum to give a white solid residue. Recrystallization in ether yields 3.40 g (56% yield) 1-(9-decenyl)-3,7-dimethylxanthine (inventive compound no. 1563).

A solution of 1-(9-decenyl)-3,7-dimethylxanthine (3.2 g, 10.1 mmol), 4-methylmorpholine-N-oxide (1.41 g, 12 mmol) and a 2.5% solution in t-butanol of osmium tetroxide (3 drops) in acetone (40 mL) and water (10 mL) was stirred for 24 hours. Following addition of 5 mL of a saturated solution of sodium dithionite and an additional 15 minutes of stirring, the reaction product was extracted with 25% ethanol/dichloromethane (4×50 mL). The combined organic portions were dried over sodium sulfate. The solvents were evaporated to a give a white solid residue. Upon recrystallization of the residue in ethanol, 3.30 g (93% yield) 1-(9,10-dihydroxydecyl)-3,7-dimethylxanthine (inventive compound no. 1564) were obtained.

A mixture of 1-(5,6-dihydroxydecyl)-3,7-dimethylxanthine (2.11 g, 6 mmol) and a 30% solution of hydrogen bromide in acetic acid (3.58 mL, 18 mmol) was stirred for 90 minutes. The mixture was then added to a flask containing aqueous sodium bicarbonate solution (5 g in 40 mL ) and dichloromethane (50 mL). After 10 minutes of vigorous stirring, the layers were separated and the aqueous portion extracted with dichloromethane (2×50 mL). The combined organic phases were dried over sodium sulfate. The solvent was evaporated, yielding 2.72 g (100%) 1-(9-acetoxy-10-bromodecyl)-3,7-dimethylxanthine as a yellow oil. Without further purification, the oil was taken up in methanol (30 mL) and treated with a 1M solution of sodium methoxide (6 mL). After 30 minutes, the reaction mixture was added to water (30 mL) and extracted with dichloromethane (3×50 mL). The organic portions were combined and dried over sodium sulfate to give an off-white solid residue. Recrystalization in dichloromethane/petroleum ether yields 380 mg (91% yield) 1-(9,10-oxidodecyl)-3,7-dimethylxanthine.

EXAMPLE 19

This example illustrates a synthesis of 3,7-dimethyl-1-(6,7-trans-oxidononyl)xanthine (inventive compound no. 1569). A mixture of 6-cis-nonen-1-ol (TCI, 990 mg, 7.0 mmol) and thiophenol (60 mg) was heated at 105°–110° C. under argon for 4 hours to give 6-nonen-1-ol 872 mg, 88% yield) with a 4:1 trans:cis isomer ratio. Without further purification, the mixture was stirred with methanesulfonyl chloride (694 mg, 6.1 mmol) in dichloromethane (20 mL) at 0° C. Triethylamine (925 mg, 9.2 mg) was added dropwise and stirring continued for 1 hour. The reaction mixture was added to an aqueous saturated solution of sodium bicarbonate (10 mL) and the layers were separated. The aqueous layer was extracted with dichloromethane (2×15 mL). The combined organic layers were washed with a 5% solution of hydrogen chloride (10 mL), water (10 mL), and an aqueous saturated solution of sodium chloride (10 mL) and then dried over sodium sulfate. The solvent was removed under vacuum to give the mesylate, which was used in the next step without purification.

A mixture of the mesylate, sodium theobromine (1.21 g, 6.0 mmol) was stirred in dimethylsulfoxide (10 mL) for 24 hours. The reaction mixture was poured into water (10 mL) and extracted with dichloromethane (3×25 mL). The combined organic extracts were washed with water (15 mL) and aqueous saturated salt solution (15 mL). After removing the solvent under vacuum, the residue was purified by silica/ethyl acetate chromotography, yielding 827 mg (67% yield) 1-(6-trans-noneyl)-3,7-dimethylxanthine (inventive compound no. 2512), 20% being contaminated with the cis isomer.

1-(6-trans-noneyl)-3,7-dimethylxanthine (110 mg, 0.4 mmol), m-chloroperbenzoic acid (75 mg, 0.4 mmol), and sodium bicarbonate (150 mg, 1.8 mmol) were stirred in dichloromethane (6 ml) and water (5 mL) for 5 hours at room temperature. A saturated solution of sodium bisulfite was added (10 mL). The layers were separated and the aqueous layer washed with dichloromethane (2×20 mL). The organic layers were combined and washed with saturated sodium bicarbonate solution (10 mL), water (10 mL), and brine (15 mL), and dried over sodium sulfate. The solvent was evaporated and the residue recrystallized in ether, yielding 70 mg (54% yield) of 1-(6,7-Oxidoheptyl)-3,7-dimethylxanthine.

EXAMPLE 20

This example illustrates a synthesis of 1-(6,7-Oxidoheptyl)-3,7-dimethylxanthine (inventive compound no. 1586). To a solution of 6-hepten-1-ol (6.00 g, 52.6 mmol) in dichloromethane (120 mL) at 0° C. was added methanesulfonyl chloride (6.07 g, 4.0 mL, 53.0 mmol), followed by triethylamine (7.79 g, 77.0 mmol). After stirring for 10 minutes at 0° C., the reaction was allowed to warm to 25° C. and then stirred for 2 hours. The reaction was poured into water (100 mL) and extracted with dichloromethane (2×100 mL). The organic portions were combined, dried over magnesium sulfate, and evaporated to give the 7-methanesulfonyl-1-heptene as a yellow oil (9.30 g, 93%), which was used without further purification.

To a suspension of sodium theobromine (9.05 g, 50.0 mmol) in dimethylsulfoxide (90 mL) was added 7-methanesulfonyl-1-heptene (9.30 g, 48.2 mmol). The reaction was stirred for 16 hours at 60° C. The mixture was then poured into water (100 mL) and extracted with ethyl acetate (3×100 mL). The organic portions were combined, dried, and evaporated to give an orange solid. Chromatography (silica, ethyl acetate/hexane) yielded 6.50 g (47% yield) 1-(6-Heptenyl)-3,7-dimethylxanthine (inventive compound no. 1534) as a white solid.

A solution of 1–4(6-Heptenyl)-3,7-dimethylxanthine (6.00 g, 21.7 mmol), 4-methylmorpholine-N-oxide (6.82 g, 58.0 mmol) and potassium osmate dihydrate (70 mg, 0.19 mmol) in acetone/water 1:2 (120 mL) was stirred for 16 hours. Water (100 mL) and sodium sulfite (5 g) were added and the reaction mixture stirred for 1 hour. The reaction mixture was extracted with 25% ethanol/dichloromethane (3×120 mL), dried over magnesium sulfate and the solvent evaporated to obtain a cream solid. Recrystallization of the solid from hot methanol/ethyl acetate 1:1 yielded 6.45 g (96% yield) 1-(6,7-Dihydroxyheptyl)-3,7-dimethylxanthine (inventive compound no. 1585) as a white solid.

1-(6,7-Dihydroxyheptyl)-theobromine (4.00 g, 12.9 mmol) was stirred with hydrogen bromide (12.53 g of a 30% solution in acetic acid, 38.7 mmol) for 2 hours. The mixture was then added over 10 minutes to water (50 mL), ice (50 g) and sodium bicarbonate (30 g) and stirred for 30 minutes. The reaction mixture was extracted with dichloromethane (3×100 mL). A combined organic phase was dried over magnesium sulfate and the solvent was evaporated to obtain a residue (4.90 g, 91% yield) of 1-(6-acetoxy-7-bromoheptyl)-3,7-dimethylxanthine.

Without further purification, this crude product was taken up in methanol (10 mL) and treated with a solution of sodium methoxide (prepared from sodium (0.285 g, 12.4 mmol) and 20 mL methanol). After 60 minutes the reaction was added to water (50 mL) and extracted with dichloromethane (3×50 mL). The organic portions were combined and dried to give an off-white solid. Recrystalization in dichloromethane/petroleum ether yielded 3.30 mg (96% yield) of 1-(6,7-Oxidoheptyl)-3,7-dimethylxanthine.

EXAMPLE 21

This example illustrates a synthesis of 1-(3-(R)-methyl-7-methyl-6,7-oxidooctyl)-3,7-dimethylxanthine (inventive compound no. 1588R). Sodium hydride(95%) (631 mg, 25 mmol) was added to a solution of theobromine (4.14 g, 23 mmol) in dimethylsulfoxide (75 mL). After 20 minutes of stirring, (R)(−)Citronellyl bromide (5.0 g, 22.8 mmol) was added. After 16 hours of stirring at room temperature, the reaction was poured into a separatory funnel containing 500 mL of water and extracted with dichloromethane (3×100 mL). The organic extracts were combined, washed with water (100 mL) and brine (100 mL), dried over anhydrous magnesium sulfate and concentrated under reduced pressure. The crude product obtained was further purified by flash chromatography over silica gel using 30% petroleum ether/ethyl acetate eluant, yielding 5.9 g (81.5% yield) 1-(3-(R)-methyl-7-methyloct-6-enyl)-3,7-dimethylxanthine (inventive compound no. 1596R) as a yellowish oil. A solution of 1-(3-(R)-methyl-7-methyloct-6-enyl)-3,7-dimethylxanthine (318 mg, 1 mmol) and m-chloroperoxybenzoic acid (0.52 g; 1.5 mmol) (50% by wt) in dichloromethane (7 mL) was stirred for 5 hours. The reaction mixture was diluted with 40 mL of dichloromethane and washed successively with 20% aqueous sodium sulphite solution (10 mL), saturated sodium bicarbonate solution (10 mL), water and brine solutions. The organic layer was dried over anhydrous magnesium sulfate and concentrated under reduced pressure. The crude product obtained was further purified by flash chromatography over silica gel using 5% petroleum ether/ethyl acetate eluant, yielding 0.253 g (76% yield) of 1-(3-(R)-methyl-7-methyl-6,7-oxidooctyl)-3,7-dimethylxanthine.

EXAMPLE 22

This example illustrates a synthesis of 1-(3-(S)-methyl-7-methyl-6,7-oxidooctyl)-3,7-dimethylxanthine (inventive compound no. 1588S). Sodium hydride (95%) (631 mg, 25 mmol) was added to a solution of theobromine (4.14 g, 23 mmol) in dimethylsulfoxide (75 mL). After 20 minutes of stirring, (S)(−)Citronellyl bromide (5.0 g, 22.8 mmol) was added. After 16 hours of stirring at room temperature, the reaction mixture was poured into a separatory funnel containing 500 mL water and extracted with dichloromethane (3×100 mL). The organic portions were combined, washed with water (100 mL) and brine (100 mL), dried over anhydrous magnesium sulfate and concentrated under reduced pressure. The crude product obtained was further purified by flash chromatography over silica gel using 30% petroleum ether/ethyl acetate eluant to yield 5.7 g (80% yield) 1-(3-(S)-methyl-7-methyloct-6-enyl)-3,7-dimethylxanthine (inventive compound no. 1596S) as an yellow oil.

A solution of 1-(3-(S)-methyl-7-methyloct-6-enyl)-3,7-dimethylxanthine (636 mg, 2 mmol) and m-chloroperoxybenzoic acid (1.04 g; 3 mmol) (50% by wt) in dichloromethane (15 mL) was stirred for 5 hours. The reaction mixture was diluted with 80 mL of dichloromethane and washed successively with 20% aqueous sodium sulphite solution(20 mL), saturated sodium bicarbonate solution (20 mL), water and brine solutions. The organic layer was dried over anhydrous magnesium sulfate and concentrated under reduced pressure. The crude product obtained was further purified by flash chromatography over silica gel using 5% petroleum ether/ethyl acetate eluant to yield 0.56 g (83% yield) 1-(3-(S)-methyl-7-methyloct-6-enyl)-3,7-dimethylxanthine.

EXAMPLE 23

This example illustrates a synthesis of 1-(4,5-Oxipentyl) -3,7- dimethylxanthine. Sodium hydride (95%) (1.38 g, 55 mmol) was added to a solution of theobromine (9.0 g, 50 mmol) in dimethylsulfoxide (300 mL). After 20 minutes of stirring, 1-bromo-4-pentene(7.45 g, 50 mmol) was added. After 16 hours of stirring at room temperature, the reaction was poured into a separatory funnel containing 1 L of water and extracted with dichloromethane (5×200 mL). The organic extracts were combined, washed with water (100 mL) and brine (100 mL), dried over anhydrous magnesium sulfate and concentrated under reduced pressure. The crude product obtained was further purified by flash chromatography over silica gel using 20% petroleum ether/ethyl acetate eluant to yield 9.67 g (92% yield) 1-(4-pentenyl)-3,7-dimethylxanthine (inventive compound no. 1575).

A solution of 1-(4-pentenyl)-3,7-dimethylxanthine (2.48 g, 10 mmol), 4-methylmorpholine-N-oxide (1.49 g, 12.7 mmol) and potassium osmate dihydrate (7.3 mg; 0.02 mmol) in acetone (20 mL) and water (5 mL) was stirred for 6 hours.

A solution of 20% aqueous sodium sulphite (10 ml) was added and stirred for 30 minutes. The reaction mixture was extracted with 25% ethanol/dichloromethane (4×250 mL). The combined organic extracts were dried over anhydrous magnesium sulfate and concentrated under reduced pressure. The crude product obtained was further purified by flash chromatography over silica gel using ethyl acetate eluant to yield 2.5 g (88% yield) of 1-(4,5-dihydroxypentyl)-3,7-dimethylxanthine (inventive compound no. 1584).

1-(4,5-Dihydroxypentyl)-3,7-dimethylxanthine (2.13 g, 7.6 mmol) was stirred with hydrogen bromide (4.74 mL, 6.15 g of a 30% solution in acetic acid, 22.8 mrnol) for 90 minutes. The mixture was then added to a flask containing 50 mL aqueous sodium bicarbonate solution and 50 mL dichloromethane. After 10 minutes of vigorous stirring, the layers were separated and the aqueous portion washed with dichloromethane (3×50 mL). The organic portions were combined, dried over magnesium sulfate, and the solvent evaporated to yield 3.4 g (96%) 1-(4-acetoxy-5-bromopentyl)-3,7-dimethylxanthine as a yellow oil. Without further purification, the oil was taken up in methanol (25 mL) and treated with a solution of sodium methoxide (prepared from 0.2 g, 8.7 mmol sodium, and 25 mL methanol). After 30 minutes most of the solvent was removed under reduced pressure and the residue extracted with dichloromethane (3×50 mL). The organic portions were combined and dried over magnesium sulfate to obtain an off-white solid purified by column chromatography over silica gel using ethyl acetate/(15%) acetone eluant to yield 1.0 g (50% yield) of 1-(4,5-Oxipentyl)-3,7-dimethylxanthine.

EXAMPLE 24

This example illustrates a synthesis of 1-(10,11-Oxidoundecanyl)-3,7-dimethylxanthine (inventive compound no. 1594). Sodium hydride(95%) (1.26 g, 50 mmol) was added to a solution of theobromine (7.2 g, 40 mmol) in dimethylsulfoxide (300 mL). After 20 minutes of stirring, undecenylmesylate (7.95 g, 30 mmol) was added and stirred for 12 hours at room temperature. The reaction was warmed to 70°–80° C. and stirred for 4 hours. The reaction mixture was then poured into a separatory funnel containing 1 L of water and extracted with dichloromethane (5×200 mL). The organic extracts are combined, washed with water (100 mL) and brine (100 mL), dried over anhydrous magnesium sulfate and concentrated under reduced pressure. The crude product obtained was further purified by flash chromatography over silica gel (eluant: 20% hexane/dichloromethane) to yield 4.6 g (46.3% yield) 1-(10-Undecenyl)-3,7-dimethylxanthine (inventive compound no. 2501).

A solution of l-(10-undecenyl)-3,7-dimethylxanthine (4.3 g, 13 mmol), 4-methylmorpholine-N-oxide (1.942 g, 16.6 mmol) and potassium osmate dihydrate (9.5 mg; 0.026 mmol) in acetone (45 mL) and water (10 mL) was stirred for 6 hours. A solution of 20% aqueous sodium sulphite (12 rnl) was added and stirred for 30 minutes. The reaction mixture was extracted with 25% ethanol/dichloromethane (4×100 mL). The combined organic extracts were dried over anhydrous magnesium sulfate, concentrated under reduced pressure and purified by flash chromatography over silica gel using methanol (5%)/dichloromethane eluant to yield 3.6 g (76% yield) 1-(10,11-dihydroxyundecanyl)-3,7-dimethylxanthine (inventive compound no. 1592).

1-(10,11-Dihydroxyundecanyl)-3,7-dimethylxanthine (3.6 g, 10 mmol) was stirred with hydrogen bromide (6.2 mL, 8.4 g of a 30% solution in acetic acid, 31.1 mmol) for 90 minutes. The mixture was then added to a flask containing 100 mL aqueous sodium bicarbonate solution and 75 mL dichloromethane. After 10 minutes of vigorous stirring the layers were separated and the aqueous portion washed with dichloromethane (3×75 mnL). The organic portions were combined, dried over magnesium sulfate, and evaporated to give 1-(10-acetoxy-11-bromoundecanyl)-3,7-dimethylxanthine (3.6 g). Without further purification, the bromoacetate was taken up in methanol (25 mL) and treated with a solution of sodium methoxide (prepared from 0.28 g, 12.2 mmol sodium, and 25 mL methanol). After 30 minutes, most of the solvent was removed under reduced pressure and the residue extracted with dichloromethane (3×75 mL). The organic portions were combined, dried over magnesium sulfate and concentrated under reduced pressure to obtain an off-white solid which was purified by column chromatography over silica gel using dichloromethane/(3%) methanol eluant to yield 2.0 g (57% yield) 1-(10,11-Oxidoundecanyl)-3,7-dimethylxanthine.

EXAMPLE 25

This example illustrates a synthesis of 1-(5,6-Oxidohexyl)glutarimide (inventive compound no. 1605). Sodium hydride (425 mg, 17.7 mmol) was added to a solution of glutarimide (2.00 g, 7.7 mmol) in dimethyl sulfoxide (40 mL). After 20 minutes of stirring, 6-bromo-1-hexene (2.90 g, 17.7 mmol) is added. After 20 hours of stirring, the reaction was poured into a separatory funnel containing 100 mL water and extracted with dichlormethane (4×50 mL). The organic portions were combined, washed with water (50 mL) and brine (50 mL) and dried to yield 2.92 g (85% yield) 1-(5-Hexenyl)glutarimide (inventive compound no. 1600) as a colorless oil.

1-(5-Hexenyl)glutarirnide (630 mg, 3.2 mmol) was dissolved in dichlormethane (10 mL) and aqueous sodium bicarbonate (2.20 g, 26 mmol in 10 mL water) was added followed by m-chloroperoxybenzoic acid (2.5 g of 50% MCPBA by wt, 7.2 mmol). After 17 hours, sodium metabisulfite (1.7 g, 9.0 mmol) was added. After 30 minutes, the reaction mixture was extracted with dichlormethane (3×10 mL). Organic portions were combined and washed with sodium bicarbonate (saturated solution, 10 mL). Purification by chromatography on silica using 10% ethanol/dichlormethane yielded 180 mg (0.9 mmol, 27% yield) 1-(5,6-Oxidohexyl)glutarimide (inventive compound no. 1605).

EXAMPLE 26

This example illustrates a synthesis of N-(8,9-Oxidononyl)glutarimide (inventive compound no. 1606). Sodium hydride (1.02 g, 44 mmol) was added to a solution of glutarimide (5.00 g, 44 mmol) in dimethyl sulfoxide (150 mL). After 20 minutes of stirring, 9-bromo-1-nonene (9.02 g, 44 mmol) was added. After 16 hours of additional stirring at room temperature, the reaction was poured into a separatory funnel containing 100 mL water and extracted with dichlormethane (3×70 mL). The organic portions were combined, washed with water (2×40 mL) and brine (50 mL) and dried to yield 10.09 g (97%) of 1-(8-Nonenyl) glutarimide (inventive compound no. 1604) as a colorless oil.

1-(8-Nonenyl)glutarimide (2.00 g, 8 mmol) was dissolved in dichlormethane (15 mL) and aqueous sodium bicarbonate (3.20 g, 38 mmol in 20 mL water) was added followed by m-chloroperoxybenzoic acid (4.5 g of 50% MCPBA by wt, 13 mmol). After 17 hours sodium metabisulfite was added slowly until no foaming was observed. After 30 minutes of stirring, the layers were separated and the aqueous layer extracted with dichlormethane (3×30 mL). The organic portions were combined and washed with sodium bicarbonate (saturated solution, 30 mL), water (20 mL), and brine (20 mL). The residue was purified using chromotography on silica with ether to yield 756 mg (36% yield) N-(8,9-Oxidononyl)glutarimide as a colorless liquid.

EXAMPLE 27

This example illustrates a synthesis of N-(11,10-Oxidoundecyl)glutarimide (inventive compound no. 1611). Sodium hydride (95%) (168 mg, 7 mmol) was added to a solution of glutarimide (565.6 mg, 5 mmol) in dimethyl sulfoxide (15 mL). After 20 minutes of stirring, 1-bromundec-10-ene (1.165 g, 5 mmol) was added and stirred for 12 hours at room temperature. The reaction mixture was then poured into a separatory funnel containing 100 mL of water and extracted with dichlormethane (5×75 mL). The organic extracts were combined, washed with water (50 mL) and brine (50 mL), dried over anhydrous magnesium sulfate and concentrated under reduced pressure. The crude product obtained was further purified by flash chromatography over silica gel using 20% ethyl acetate/hexane eluant to yield 0.777 g (58.6% yield) N-(10-Undecenyl)glutarimide (inventive compound no. 1610).

A solution of N-(10-Undecenyl)glutarimide (0.6 g, 2.24 mmol) and m-chloroperoxybenzoic acid (1.16 g; 3.37 mmol) (50% by wt) in dichloromethane (15 mL) were stirred for 5 hours. The reaction mixture was diluted with 20 mL of dichloromethane and washed successively with 20% aqueous sodium sulphite solution (10 mL), saturated sodium bicarbonate solution (10 mL), water (10 mL) and brine solutions (10 mL). The organic layer was dried over anhydrous magnesium sulfate and concentrated under reduced pressure. The crude product obtained was further purified by flash chromatography over silica gel using 80% petroleum ether/acetone eluant to yield 0.6 g (94% yield) of N-(11,10-Oxidoundecyl)glutarimide.

EXAMPLE 28

This example illustrates a synthesis of N-(10,11-Oxidoundecyl)-2-piperidone (inventive compound no. 1618). A mixture of potassium hydroxide (1.55 g, 25 mmol, pellets ground in mortar and pestle) and tetrabutylammonium bromide (1.61 g, 5.0 mmol) was stirred in dry tetrahydrofuran (10 mL). A solution of d-valerolactam (2.5 g, 25 mmol) and 1-bromo-10-undecene (Lancaster, 5.9 g, 25 mmol) in tetrahydrofuran (15 mL) was added by syringe pump over 1 hour. After stirring for a further 6 hours. Water (60 mL) and dichloromethane (60 mL) was added to the reaction mixture. The layers were separated and the aqueous layer was extracted with dichloromethane (2×50 mL). The combined organic layers were washed with water (50 mL) and saturated salt solution (50 mL) and then dried with sodium sulfate. The residue was further purified by chromatography using silica and 30% hexane, ethyl acetate to yield 2.88 g (46% yield) of N-(10-Undecenyl)-2-piperidone (inventive compound no. 1616) as a colorless oil.

To a mixture of N-(10-Undecenyl)-2-piperidone (4.00 g, 16 mmol) and a 60% aqueous solution of N-methylmorpholine-N-oxide (5 mL, 29 mmol) in water (10 mL) and acetone (20 mL) was added potassium osmate dihydrate (12 mg, 0.03 mmol). After stirring for 3 days, the mixture was treated with sodium dithionite (100 mg). After 30 minutes, dichloromethane (50 mL) and water (30 mL) were added and the organic layer separated. The aqueous layer was extracted with dichloromethane/10% methanol (2×70 mL). The combined organic extracts were dried over sodium sulfate and the solvents evaporated under vacuum. The residue was purified by chromatography using silica and ethyl acetate/methanol in a 0–20% gradient to yield 4.21 g (93%) N-(10,11-Dihydroxyundecyl)-2-piperidone (inventive compound no. 1617) as a colorless oil.

To N-(10,11-dihydroxyundecyl)-2-piperidone (4.21 g, 14.8 mmol) was added 30% hydrogen bromide-acetic acid (8.7 mL) and the mixture was then stirred for 1 hour. The solution was poured carefully into a mixture of sodium bicarbonate (15 g), ice water (150 mL), and dichloromethane (100 mL). After carbon dioxide evolution has subsided, the organic layer was separated and the aqueous layer extracted with dichloromethane (2×80ML). The combined organic layers was dried over sodium sulfate and the solvent evaporated under vacuum to give 1-(10-acetoxy-11-bromoundecyl)-2-piperidone (4.9 g, 89% yield) as a viscous oil which dissolves in methanol (10 mL). A 1M sodium methoxide (15 mL, 15 mmol) in methanol solution was added all at once. After stirring for 1 hour, the solution was treated with water (50 mL) and then extracted with dichloromethane (3×50 mL). The combined extracts were dried over sodium sulfate and the solvent evaporated under vacuum. The residue was purified by chromatography using ethyl acetate to yield 2.40 g (61% yield) N-(10,11-Oxidoundecyl)-2-piperidone as a colorless oil.

EXAMPLE 29

This example illustrates a synthesis of N-(9,10-Oxidodecyl)piperidine (inventive compound no. 1619). Sodium hydride (95%) (864 mg, 36 mmol) was added to a solution of piperidine (2.554 g, 30 mmol) in dimethyl sulfoxide (75 mL). After 20 minutes of stirring, 1-bromundec-10-ene (6.99 g, 5 mmol) was added and stirred for 12 hours at room temperature. The reaction mixture was then poured into a separatory funnel containing 100 mL of water and extracted with dichlormethane (5×75 mL). The organic extracts were combined, washed with water (50 mL) and brine (50 mL), dried over anhydrous magnesium sulfate and concentrated under reduced pressure. The crude product obtained was further purified by flash chromatography over silica gel using 5% methanol/dichloromethane eluant to yield 3.12 g (44% yield) N-(10-undecenyl)piperidine (inventive compound no. 1615).

A solution of N-(10-undecenyl)piperidine (3.1 g, 13 mmol), 4-methylmorpholine-N-oxide (1.84 g, 15.7 mmol) and potassium osmate dihydrate (13 mg) in acetone (64 mL) and water (16 mL) were stirred for 6 hours. The reaction was quenched by the addition of 25 mL of a saturated solution of sodium sulphite and stirred for 15 minutes. The reaction mixture was then extracted with ethyl acetate (4×100 mL), the combined organic extract was dried over anhydrous magnesium sulphate and concentrated under reduced pressure. The crude product obtained was further purified by flash chromatography over silica gel using 10% methanol/ethyl acetate eluant to yield 2.5 g (83.4% yield) N-(11,10-dihydroxyundecyl)piperidine (inventive compound no. 1622).

A mixture of N-(11,10-dihydroxyundecyl)piperidine (2.0 g, 7.4 mmol) and a 30% solution of hydrogen bromide in acetic acid (4.45 mL, 22 mmol) was stirred for 90 minutes. The mixture was then added to a flask containing aqueous sodium bicarbonate solution (15 g in 40 mL) and dichloromethane (50 mL). After 10 minutes of vigorous stirring, the layers were separated and the aqueous portion extracted with dichloromethane (2×50 mL). The combined organic portions were dried over sodium sulfate. The solvent was evaporated to give 1-(10-acetoxy-11-bromoundecyl) piperidine which was used without further purification. Bromoacetate was dissolved in methanol (10 mL) and treated with a 1M solution of sodium methoxide (8 mL). After 30 minutes, the reaction mixture was added to water (30 mL) and extracted with dichloromethane (3×50 mL). The organic extracts were combined, washed with water (25 mL) and brine solution (25 mL) and then dried over anhydrous magnesium sulphate solution and concentrated under reduced pressure. The crude product obtained was further purified by column chromatography over alumina (grade-II) using 10% methanol/ethyl acetate eluant to yield 1.5 g (80.6%) N-(9,10-Oxidodecyl)piperidine.

EXAMPLE 30

This example illustrates a synthesis of 1-Methyl-3-(8,9-oxidononyl)uracil (inventive compound no. 1804). Sodium hydride (365 mg, 16 mmol) was added to a stirring solution of 1-methyluracil (2.00 g, 16 mmol) in dimethyl sulfoxide (40 mL). After 15 minutes, 6-bromo-1-nonene (3.26 g, 16 mmol) was added and the mixture stirred for 3 days. The reaction was then poured into water (50 mL) and extracted with dichloromethane (3×60 mL). The combined organic layers were washed with water (50 mL), and aqueous saturated salt solution (30 mL) was then dried over sodium sulfate. The solvent was evaporated under vacuum to yield 3.72 g (94%) 1-methyl-3-(8-nonenyl)uracil (inventive compound no. 1817) as a colorless oil which solidified upon standing.

A solution of 1-methyl-3-(8,9-nonenyl)uracil (3.72 g, 15 mmol), 4-methylmorpholine-N oxide (2.10 g, 18 mmol), and potassium osmate (IV) dihydrate (11 mg, 3.0×10$^{-5}$ mmol) in acetone (20 mL) and water (10 mL) are stirred for 2 days. After addition of sodium hydrosulfite (100 mg) to quench the catalyst, the reaction mixture was extracted with dichloromethane (4×50 mL). The combined organic layers were dried over sodium sulfate and the solvent evaporated under vacuum to give an oily residue. Crystallization of the residue from ether/dichloromethane yields 2.66 g (63% yields) 3-(8,9-dihydroxynonyl)-1-methyluracil (inventive compound no. 1818) as white crystals.

A mixture of 3-(8,9-dihydroxynonyl)-1-methyluracil (2.15 g, 7.6 mmol) and a 30% solution of hydrogen bromide in acetic acid (4.5 mL, 23 mmol) were stirred for 6 hours. The reaction mixture was added slowly to a mixture of sodium bicarbonate (8.4 g, 0.1 mol), water (30 mL), and dichloromethane (30 mL). The layers were separated, and the aqueous layer extracted with dichloromethane (3×40 mL). The combined organic layers were washed with aqueous saturated salt solution (20 mL) and dried over sodium sulfate. The solvent was removed under vacuum to yield 2.89 g (97% yield) 3-(8-acetoxy-9-bromononyl)-1-methyluracil (inventive compound no. 1801) as a thick, slightly orange oil.

To a solution of 3-(8-acetoxy-9-bromononyl)-1-methyluracil (2.89 g, 7.4 mmol) in methanol (10 mL) was added a 1M methanol solution of sodium methoxide (8 mL). After 3 hours, the reaction mixture was poured into water (30 mL) and extracted with dichloromethane (3×60 mL). The combined organic layers were washed with water (30 mL) and aqueous saturated salt solution (30 mL), then dried over sodium sulfate. The solvent was evaporated under vacuum and the residue crystallized in ether to yield 1.61 (82% yield) 1-methyl-3-(8,9-oxidononyl)uracil.

EXAMPLE 31

This example illustrates a synthesis of 3-(5,6-Oxidohexyl)-1-methyluracil (inventive compound no. 1808). Sodium hydride (86 mg, 3.6 mmol) was added to a stirring solution of 1-methyluracil (500 mg, 4 mmol) in dimethyl sulfoxide (25 mL). After 15 minutes, 6-bromo-1-hexene (647 mg, 4 mmol) was added and the mixture stirred further for 20 hours. The reaction mixture was then poured into water (50 mL) and extracted with 20% ethanol/dichloromethane (3×50 mL). The combined organic layers were washed with aqueous saturated salt solution (20 mL) and dried over sodium sulfate. The solvent was evaporated under vacuum to give a residue which was purified by chromatography with silica and ethyl acetate to yield 598 g (72% yield) of 3-hexenyl-1-methyluracil (inventive compound no. 1800).

A solution of 3-(5-hexenyl)-1-methyluracil (598 mg, 2.9 mmol), 4-methylmorpholine-N oxide (408 mg, 3.5 mmol), and a 2.5% solution in t-butanol of osmium tetroxide (3 drops) in acetone (15 mL) and water (5 mL) was stirred for 3 days. After addition of a saturated solution of sodium hydrosulfite (10 mL) and 15 minutes, the reaction mixture was added to water (15 mL) and extracted with 20% ethanol/dichloromethane (4×40 mL). The combined organic layers were dried over sodium sulfate and the solvent is evaporated under vacuum to give 461 mg (66%) 3-(5,6-dihydroxyhexyl)-1-methyluracil (inventive compound no. 1811) as a colorless oil.

A mixture of 3-(5,6-dihydroxyhexyl)-1-methyluracil (350 mg, 1.4 mmol) and a 30% solution of hydrogen bromide in acetic acid (0.87 mL, 4.3 mmol) was stirred for 45 minutes. The mixture was then added to a mixture of sodium bicarbonate (1.6 g), water (10 mL) and dichloromethane (20 mL). After 15 minutes of vigorous stirring, the layers were separated and the aqueous layer extracted with dichloromethane (3×40 mL). The combined organic layers were dried over sodium sulfate, then evaporated under vacuum to give 3-(5-acetoxy-6-bromohexyl)-1-methyluracil (500 mg, 100% yield).

Bromoacetate was used in the next step without further purification. A solution of 3-(5-acetoxy-6-bromohexyl)-1-methyluracil (360 mg, 1.0 mmol) in methanol (5 mL) was treated with a 1M methanol solution of sodium methoxide (1.3 mL). After 15 minutes, the reaction solution was poured into water (10 mL) and extracted with dichloromethane (3×30 mL). The combined organic layers were dried over sodium sulfate and the solvent was evaporated under vacuum to yield 150 mg (67% yield) 3-(5,6-oxidohexyl)-1-methyluracil as a colorless oil.

EXAMPLE 32

This example illustrates a synthesis of 3-(5,6-oxidohexyl)-2-methyldihydrouracil (inventive compound no. 1820). Sodium hydride (288 mg, 12 mmol) was added to a solution of N-methylhydrouracil (1.54 g, 12 mmol) and 1-bromo-5-hexene (1.63 g, 10 mmol) in 20 mL of dimethyl sulfoxide at room temperature and stirred for 12 hours. The reaction mixture was then quenched with water (80 mL) and extracted with dichloromethane (3×100 mL). The combined organic extract was washed with saturated aqueous salt solution solution (50 mL), dried over anhydrous magnesium sulfate and concentrated under reduced pressure. The crude product obtained was further purified by flash chromatography over silica gel using 20% acetone/hexane eluant to yield 2.0 g (79%) 3-(5-hexenyl)-1-methylhydrouracil (inventive compound no. 1812).

A solution of 3-(5-hexenyl)-1-methylhydrouracil (1.5 g, 7.1 mmol), and m-chloroperoxybenzoic acid (3.68 g, 10.7 mmol) (50% by wt) in dichloromethane (60 mL) was stirred for 5 hours. The reaction mixture was quenched with 20% aqueous sodium sulphite solution(75 mL) and extracted with dichloromethane (3×100 mL). The combined organic extract is washed successively with saturated aqueous saturated salt solution (50 mL), saturated sodium bicarbonate solution (50 mL), water (50 mL), aqueous saturated salt solution (50 mL), dried over anhydrous magnesium sulfate and concentrated under reduced pressure. The crude product obtained was further purified by flash chromatography over silica gel using 30% acetone/hexane eluant to yield 1.27 g (78.8% yield) 3-(5,6-oxidohexyl)-2-methyldihydrouracil (inventive compound no. 1820).

EXAMPLE 33

This example illustrates a synthesis of 3-(10,11-Oxidoundecanyl)-1-methylhydrouracil (inventive compound no. 1822). Sodium hydride (288 mg, 12 mmol) was added to a solution of N-methylhydrouracil (1.54 g, 12 mmol) and 1-bromo-10-undecene (2.33 g, 10 mmol) in 20 mL of dimethyl sulfoxide at room temperature and stirred for 12 hours. The reaction mixture was then quenched with water (80 mL) and extracted with dichloromethane (3×100 mL). The combined organic extract was washed with saturated aqueous salt solution (50 mL), dried over anhydrous magnesium sulfate and concentrated under reduced pressure. The crude product obtained was further purified by flash chromatography over silica gel using a 20% acetoneihexane eluant to yield 2.04 g (61.8% yield) of 3-(10-undecenyl)-1-methylhydrouracil (inventive compound no. 1819).

A solution of 3-(10-undecenyl)-1-methylhydrouracil (0.28 g, 1 mmol), and m-chloroperoxybenzoic acid (0.517 g, 1.5 mmol) (50% by wt) in dichloromethane (6 mL) was stirred for 5 hours. The reaction mixture was diluted with 75 mL of dichloromethane and washed successively with 20% aqueous sodium sulphite solution(25 mL), saturated NaHCO3 solution (25 mL), water (25 mL), aqueous saturated salt solution (25 mL), dried over anhydrous magnesium sulfate and concentrated under reduced pressure. The crude product obtained was further purified by flash chromatography over silica gel using 20% acetone/hexane eluant to yield 0.22 g (74.3%) 3-(10,11-Oxidoundecanyl)-1-methylhydrouracil.

EXAMPLE 34

This example illustrates a synthesis of 3-(5,6-Oxidohexyl)-1-methylthymine (inventive compound no. 1906). Sodium hydride (343 mg, 14 mmol) was added to a stirring solution of 1-methylthymine (Sigma, 2.00 g, 14 mmol) in dimethylsulfoxide (30 mL). After 15 minutes, 6-bromo-1-hexene (Lancaster, 2.30 g, 14 mmol) was added and stirring continued for 69 hours. The reaction mixture was then poured into water (100 mL) and extracted with dichloromethane (4×50 mL). The combined organic layers were washed with saturated aqueous salt solution (40 mL) and dried over sodium sulfate. The solvent was evaporated under vacuum to give a residue which was crystallized in dichloromethane/ethyl ether to yield 2.80 g (88% yield) 3-(5-hexenyl)-1-methylthymine (inventive compound no. 1905).

A solution of 3-(5-hexenyl)-1-methylthymine (2.00 g, 9 mmol), 4-methylmorpholine-N oxide (1.17 mg, 10 mmol), and a 2.5% sol. in t-butanol of osmium tetroxide (0.15 mL ) in acetone (15 mL) and water (10 mL) was stirred for 20 hours. After addition of a saturated solution of sodium hydrosulfite (10 mL) and 15 minutes of stirring, the reaction mixture was extracted with 20% ethanolldichloromethane (4×40 mL). The combined organic layers were dried over sodium sulfate and the solvent evaporated under vacuum to a give white solid residue. The solid was recrystallized in ethanol to yield 2.00 g (89%) of 3-(5,6-dihydroxyhexyl)-1-methylthymine (inventive compound no. 1907).

A mixture of 3-(5,6-dihydroxyhexyl)-1-methylthymine (1.65 g, 6.4 mmol) and a 30% solution of hydrogen bromide in acetic acid (3.8 mL, 19.3 mmol) in water (5 mL) and acetone (10 mL) was stirred for 1.5 hours. The mixture was then added to a flask containing sodium bicarbonate (6.7 g), water (40 mL) and dichloromethane (50 mL). After 15 minutes of vigorous stirring, the layers were separated and the aqueous layer washed with dichloromethane (2×50 mL). The combined organic layers were dried over sodium sulfate. The solvent was evaporated under vacuum to yield 2.30 g (100%) of 3-(5-acetoxy-6-bromohexyl)-1-methylthymine as a yellow oil. The bromoacetate was used in the next step without further purification. A solution of 3-(5-acetoxy-6-bromohexyl)-1-methylthymine (2.30 g, 6.4 mmol) in methanol (10 mL) was treated with a 1M methanol solution of sodium methoxide (7 mL). After stirring for 15 minutes, the solution was poured into water (60 mL) and extracted with 20% ethanovdichloromethane (2×70 mL). The combined organic layers were dried over sodium sulfate and the solvent evaporated under vacuum to yield 1.30 g (85%) 3-(5,6-oxidohexyl)-1-methylthymine as a white solid.

EXAMPLE 35

This example illustrates a synthesis of 1-Methyl-3-(8,9-oxidononyl)thymine (inventive compound no. 1910). Sodium hydride (343 mg, 14 mmol) was added to a stirring solution of 1-methylthymine (2.00 g, 14 nmuol) in dimethylsulfoxide (40 mL). After 15 minutes, 9-bromo-1-nonene (2.93 g, 14 mmol) was added and the mixture stirred for 20 hours. The reaction was poured into 40 mL water and extracted with dichloromethane (3×50 mL). The organic layers were combined, washed with water (40 mL), saturated aqueous salt solution (20 mL), and dried over sodium sulfate. The solvent was evaporated to yield 2.76 g (73% yield) 1-Methyl-3-(8-nonenyl)thymine (inventive compound no. 1917) as a colorless oil which solidified upon standing.

A solution of 1-methyl-3-(8-nonenyl)thymine (2.63 g, 9.9 mmol), 4-methylmorpholine-N oxide (1.39 g, 12 mmol), and potassium osmate (IV) dihydrate (7 mg, 2×10$^{-5}$ mol) in acetone (20 mL) and water (10 mL) was stirred for 18 hours. After addition of a saturated aqueous solution of sodium hydrosulfite (10 mL) and 15 minutes of stirring, the reaction mixture was extracted with dichloromethane (50 mL) and with dichloromethane/20% methanol (2×50 mL). The combined organic layers were washed with water (15 mL) and saturated aqueous salt solution (15 mL), and then dried over sodium sulfate. The solvent was evaporated under vacuum to give a white solid residue. The solid was recrystallized in ethanol to yield 2.68 g (91% yield) 3-(8,9-dihydroxynonyl)-1-methylthymine (inventive compound no. 1918).

A mixture of 3-(8,9-dihydroxynonyl)-1-methylthymine (2.16 g, 7.6 mmol) and a 30% solution of hydrogen bromide in acetic acid (4.5 mL, 23 mmol ) was stirred for 1 hour. The reaction was added slowly to a beaker containing sodium bicarbonate (8.4 g, 0.1 mol), ice water (30 mL), and dichloromethane (30 mL). The layers were separated and the aqueous layer extracted with dichloromethane (2×60 mL). The combined organic layers were washed with water (30 mL), saturated aqueous salt solution (30 mL), and dried over sodium sulfate. The solvent was removed to yield 2.59 g (85% yield) 3-(8-acetoxy-9-bromononyl)-1-methylthymine (inventive compound no. 1908) as a thick, slightly orange oil.

To a solution of 3-(8-acetoxy-9-bromononyl)-1-methylthymine (2.04 g, 5.1 mmol) in methanol (15 mL) was added a 1M solution of sodium methoxide (6 mL). After 3 hours, the reaction was poured into water (20 mL) and extracted with dichloromethane (3×30 mL). The combined organic layers were washed with water (20 mL) and saturated aqueous salt solution (20 mL), then dried over sodium sulfate. The solvent was evaporated under vacuum and the residue crystallized in dichloromethane-ether to yield 1.09 g (76% yield) white crystals of 1-methyl-3-(8,9-oxidononyl) thymine.

EXAMPLE 36

This example illustrates a synthesis of 3-(11,10-Oxidoundecyl)-1-methylthymine (inventive compound no. 1932). Sodium hydride (95%) (168 mg, 7 mmol) was added to a solution of 1-methylthymine (700.5 mg, 5 mmol) in dimethylsulfoxide (15 mL). After 20 minutes of stirring, 1-bromundec-10-ene (1.165 g, 5 mmol) was added and stirred for 12 hours at room temperature. The reaction mixture was then poured into a separatory funnel containing 100 mL of water and extracted with dichloromethane (5×75 mL). The organic extracts were combined, washed with water (50 mL) and saturated aqueous salt solution (50 mL), dried over anhydrous magnesium sulfate and concentrated under reduced pressure. The crude product obtained was further purified by flash chromatography over silica gel using a 20% ethyl acetate/hexane eluant to yield 1.22 g (83.7% yield) 3-(10-undecenyl)-1-methylthymine (inventive compound no. 1931).

A solution of 3-(10-undecenyl)-1-methylthymine (2 g, 6.8 mmol), and m-chloroperoxybenzoic acid (3.5 g, 10.2 mmol) (50% by wt) in dichioromethane (50 mL) was stirred for 5 hours. The reaction mixture was diluted with 80 mL of dichloromethane and washed successively with 20% aqueous sodium sulphite solution (30 mL), saturated sodium bicarbonate solution (30 mL), water (30 mL) and brine solutions (30 mL). The organic layer was dried over anhydrous magnesium sulfate and concentrated under reduced pressure. The crude product obtained was further purified by flash chromatography over silica gel using a 70% hexane/ethyl acetate eluant to yield 1.73 g (82% yield) 3-(11,10-Oxidoundecyl)-1-methylthymine (inventive compound no. 1932).

EXAMPLE 37

This example illustrates a synthesis of 1-(3,4-Oxidobutyl)-3,7-dimethylxanthine (inventive compound no. 2513). Sodium hydride (95%) (1.26 g, 50 mmol) was added to a solution of theobromine (7.2 g, 40 mmol) in dimethylsulfoxide (300 mL). After 20 minutes of stirring, 4-bromobutene (5.4 g, 40 mmol) was added. After 16 hours of stirring at room temperature, the reaction was poured into a separatory funnel containing 1 L of water and extracted with dichloromethane (5×200 mL). The organic extracts were combined, washed with water (100 mL) and brine (100 mL), dried over anhydrous magnesium sulfate and concentrated under reduced pressure. The crude product obtained was further purified by flash chromatography over silica gel using a 20% petroleum ether/ethyl acetate eluant to yield 6.3 g (67.7% yield) 1-(3-Butenyl)-3,7-dimethylxanthine (inventive compound no. 2503) as a white solid.

A solution of 1-(3-Butenyl)-3,7-dimethylxanthine (5.8 g, 24.8 mmol), 4-methylmorpholine-N-oxide (3.63 g, 31 mmol) and potassium osmate dihydrate (18.3 mg; 0.05 mmol) in acetone (40 mL) and water (10 mL) was stirred for 6 hours. A solution of 20% aqueous sodium sulphite (20 ml) was added and stirred for 30 minutes. The reaction mixture was extracted with 25% ethanol/dichloromethane (4×250 mL). The combined organic extracts were dried over anhydrous magnesium sulfate and concentrated under reduced pressure. The crude product obtained was further purified by flash chromatography over silica gel using an acetone eluant to yield 4.5 g (67.7% yield) 1-(3,4,-dihydroxybutyl)-3,7-dimethylxanthine (inventive compound no. 2509).

1-(3,4-Dihydroxybutyl)-3,7-dimethylxanthine (3.98 g, 14.9 mmol) was stirred with hydrogen bromide (9.2 mL, 12.06 g of a 30% solution in acetic acid, 44.7 mmol) for 90 minutes. The mixture was then added to a flask containing 200 mL aqueous saturated sodium bicarbonate solution and 75 mL dichloromethane. After 10 minutes of vigorous stirring, the layers were separated and the aqueous portion washed with dichloromethane (3×150 mL). The organic portions were combined, dried (magnesium sulfate), and evaporated to give 1-(3-acetoxy-4-bromobutyl)-3,7-dimethylxanthine(5.6 g). Without further purification, the bromoacetate was taken up in methanol (50 mL) and treated with a solution of sodium methoxide (prepared from 0.414 g, 12.2 mmol sodium, and 25 mL methanol). After 30 minutes, most of the solvent was removed under reduced pressure and the residue extracted with 25% ethanol/dichloromethane (3×150 mL). The organic portions were combined, dried (magnesium sulfate) and concentrated under reduced pressure to give an off-white solid which is purified by column chromatography over silica gel using an ethyl acetate eluant to yield 2.2 g (58% yield) 1-(3,4-Oxidobutyl)-3,7-dimethylxanthine.

EXAMPLE 38

This example illustrates a synthesis of 1-(11,12-Oxidododecyl)-3,7-dimethylxanthine (inventive compound no. 2518). To a suspension of magnesium (6.4 g, 265 mmol) and a crystal of iodine in tetrahydrofuran (40 mL) was added 10-undecenyl bromide (12.25 g, 53.0 mmol, available from MTM) in tetrahydrofuran (30 mL) over 30 minutes and the reaction stirred for a further 30 minutes after the addition was complete. The solution was added via a canula over 5 minutes to a suspension of paraformaldehyde (1.80 g, 60.0 mmol) in tetrahydrofuran (40 mL) and stirred at 25° C. for 16 hours. Saturated ammonium chloride (80 mL) is added and extracted with diethyl ether (2×100 mL). The combined organic extracts are dried using magnesium sulfate and evaporated to give a residue which is distilled at 2 mm Hg to yield 6.53 g (67% yield, b.p. 105°–107° C.) of 11-dodecenyl alcohol as a clear liquid.

To a solution of 11-dodecen-1-ol (5.5 g, 29.9 mmol) in dichloromethane (70 mL) at 0° C. was added methanesulfonyl chloride (3.55 g, 2.40 mL, 31.0 mmol) followed by triethylamine (4.38 g, 46.0 mmol). After stirring for 10 minutes at 0° C., the reaction was allowed to warm to 25° C. and stirred for 2 hours. The reaction was poured into water (60 mL), separated and washed with dichloromethane (50 mL). The organic portions were combined, dried using magnesium sulfate, and evaporated to yield 12-methanesulfonyl-1-dodecene as a yellow oil which was then used without further purification.

To a suspension of sodium theobromine (6.00 g, 30.0 mmol) in dimethylsulfoxide (60 mL) was added 12-methanesulfonyl-1-dodecene and the reaction stirred for 16 hours at 60° C. The mixture was then poured into water (120 mL) and extracted with diethyl ether (2×100 mL). The organic portions were combined, dried using magnesium sulfate and evaporated to give a cream solid. Recrystallization from ethyl acetate/hexane 1:1 yields 6.97 g (67% yield) 1-(11-dodecenyl)-3,7-dimethylxanthine (inventive compound no. 2516) as a white solid.

A solution of 1-(11-Dodecenyl)-3,7-dimethylxanthine (4.70 g, 13.6 mmol), 4-methylmorpholine-N-oxide (4.79 g, 40.7 mmol) and potassium osmate dihydrate (52 mg, 0.14 mmol) in acetone/water 1:2 (75 mL) was stirred for 16 hours. Water (50 mL) and sodium sulfite (5 g) were added and the mixture stirred for 1 hour. The reaction mixture was extracted with dichloromethane (3×100 mL), dried using magnesium sulfate and evaporated to obtain a pale green solid. Recrystallization from hot ethyl acetate yields 4.32 g (84% yield) 1-(11,12-dihydroxydodecyl)-3,7-dimethylxanthine (inventive compound no. 2517) as a white solid.

1-(11,12-Dihydroxydodecyl)-3,7-dimethylxanthine (2.50 g, 6.58 mmol) was stirred with hydrogen bromide (6.39 mL of a 30% solution in acetic acid, 19.73 mmol) for 2 hours. The mixture was then added over 10 minutes to water (25 mL), ice (30 g) and sodium hydride $CO_3$ (15 g) and stirred for 30 minutes. The reaction mixture was extracted with dichloromethane (3×50 mL), and the combined organic phases were dried using magnesium sulfate and evaporated to obtain 3.18 g (99% yield) of 1-(11-acetoxy-12-bromododecyl)-3,7-dimethylxanthine. Without further purification, this crude product was taken up in methanol (10 mL) and treated with a solution of sodium methoxide (prepared from sodium, 0.160 g, 6.90 mmol, and 20 mL methanol). After 60 minutes, the reaction was added to water (30 mL) and extracted with dichloromethane (3×50 mL). The organic portions were combined, dried and evaporated to yield 2.20 g (93% yield) 1-(11,12-oxidododecyl)-3,7-dimethylxanthine as a white solid.

EXAMPLE 39

This example illustrates a synthesis of 1-(9,10-Oxidoctadecyl)-3,7-dimethylxanthine (inventive compound no. 2541). Triphenylphosphine (5.24 g; 20 mmol) was added in portions to a solution of oleyl alcohol (5.37 g; 20 mmol) and carbontetrabromide (6.63 g; 20 mmol) in 400 mL of dichloromethane and stirred for an hour at room temperature. The solvent was removed under reduced pressure and the residue extracted with hexane (3×200 mL). Further purification was done by flash chromatography over silica gel using hexane as eluant to yield 5.82 g (88% yield) of 1-bromo-9-octadecene.

Sodium hydride (95%) (84 mg, 3.5 mmol) was added to a solution of theobromine (0.595 g, 3.2 mmol) in dimethylsulfoxide (15 mL). After 20 minutes of stirring, 1-bromo-9-ctadecene(0.995 g, 3 mmol) was added. After 6 hours of stirring at room temperature, the reaction mixture was warmed to 60° C. for 3 hours and then poured into a separatory funnel containing 50 mL of water and extracted with dichloromethane (5×40 mL). The organic extracts were combined, washed with water (50 mL) and brine (50 mL), dried over anhydrous magnesium sulfate and concentrated under reduced pressure. The crude product obtained was further purified by flash chromatography over silica gel using a 30% acetone/petroleum ether eluant to yield 0.44 g (34% yield) of ) 1-(9-octadecenyl)-3,7-dimethylxanthine (inventive compound no. 2539).

A solution of 1-(9-octadecenyl)-3,7-dimethylxanthine (0.15 g, 0.35 mmol) and m-chloroperoxybenzoic acid (0.15 g, 0.43 mmol) (50% by wt) in dichloromethane (7 mL) was stirred for 5 hours. The reaction mixture was diluted with 40 mL of dichloromethane and washed successively with 20% aqueous sodium sulphite solution (10 mL), saturated sodium bicarbonate solution (10 mL), water and brine solutions. The organic layer was dried over anhydrous magnesium sulfate and concentrated under reduced pressure. The crude product obtained was further purified by flash chromatography over silica gel using a 30% acetone/hexane eluant to yield 0.73 g (48.4% yield) of 1-(9,10-oxidoctadecyl)-3,7-dimethylxanthine.

EXAMPLE 40

This example illustrates a synthesis of 1-(4-(S)-Methyl-7,8-oxido-8-methylnonyl)-3,7-dimethylxanthine (inventive compound no. 2548S). To a suspension of magnesium (2.74 g, 140 mmol) and a crystal of iodine in tetrahydrofuran (15 mL) was added (S)-citronellyl bromide (5.0 g, 22.8 mmol) in tetrahydrofuran (10 mL) over 30 minutes and the reaction stirred for a further 30 minutes after the addition was complete. The solution was added via a canula over 5 minutes to a suspension of paraformaldehyde (1.80 g, 60.0 mmol) in tetrahydrofuran (15 mL) and stirred at 25° C. for 6 hours. Saturated ammonium chloride (40 mL) was added and extracted with diethyl ether (2×30 mL). The combined organic extracts were dried (magnesium sulfate) and evaporated to yield 3.25 g (84% yield) 4-(S)-methyl-8-methylnon-7-enyl alcohol as a clear liquid.

To a solution of 4-(S)-methyl-8-methylnon-7-enyl alcohol (3.25 g, 19.1 mmol) in dichloromethane (50 mL) at 0° C. is added methanesulfonyl chloride (2.29 g, 20.0 mmol) followed by triethylamine (3.04 g, 30.0 mmol). After stirring for 10 minutes at 0° C., the reaction was allowed to warm to 25° C. and stirred for 3 hours. The reaction was poured into water (50 mL), separated and washed with dichloromethane (50 mL). The organic portions were combined, dried using magnesium sulfate, and evaporated to give the 1-methanesulfonyl-4-(S)-methyl-8-methylnon-7-ene as a yellow oil which is used without further purification.

To a suspension of sodium theobromine (4.05 g, 20.0 mmol) in dimethylsulfoxide (50 mL) was added 1-methanesulfonyl-4-(S)-methyl-8-methylnon-7-ene and the reaction stirred for 16 hours at 60° C. The mixture was then poured into water (100 mL) and extracted with ethyl acetate (100 mL, 2×50 mL). The organic portions were combined, dried using magnesium sulfate, and evaporated to give a residue which was purified by column chromatography (ethyl acetate/hexane) to yield 1.83 g (30% yield) 1-(4-(S)-Methyl-8-methylnon-7-enyl)-3,7-dimethylxanthine (inventive compound no. 2536S) as a white solid.

A solution of (0.65 g, 1.96 mmol), 4-methylmorpholine-N-oxide (0.69 g, 5.87 mmol) and potassium osmate dihydrate (7 mg, 0.021 mmol) in acetone/water 1:2 (12 mL) was stirred for 16 hours. Water (10 mL) and sodium sulfite (1 g) were added and the reaction mixture stirred for 1 hour. The reaction mixture was extracted with dichloromethane (3×30 ml), dried using magnesium sulfate and the solvent evaporated to yield 0.675 g (94%) of 1-(4-(S)-methyl-7,8-dihydroxy-8-methylnonyl)-3,7-dimethylxanthine (inventive compound no. 2537S) as a colorless oil.

1-(4-(S)-Methyl-7,8-dihydroxy-8-methylnonyl)-3,7-dimethylxanthine (0.37 g, 1.00 mmol) was stirred with hydrogen bromide (1.25 mL of a 30% solution in acetic acid, 3.00 mmol) for 4 hours. The mixture was then added over 10 minutes to water (10 mL), ice (5 g) and sodium bicarbonate (2 g) and stirred for 30 minutes. The reaction mixture was extracted with dichloromethane (2×15 mL), and the combined organic phases were dried using magnesium sulfate and the solvent evaporated to yield a residue of 1-(4-(S)-methyl-7-acetoxy-8-bromo-8-methylnonyl)-3,7-dimethylxanthine.

Without further purification, the crude residue was taken up in methanol (5 mL) and treated with a solution of sodium methoxide (prepared from sodium (0.025 g, 1.09 mmol) and 5 mL methanol). After 40 minutes, the reaction mixture was added to water (10 mL) and extracted with dichloromethane (3×10 mL). The organic portions were combined, dried and the solvent evaporated to yield 0.32 g (92%) 1-(4-(S)-Methyl-7,8-oxido-8-methylnon)-3,7-dimethylxanthine as a white solid.

EXAMPLE 41

This example illustrates a synthesis of 1-(4-(R)-Methyl-7,8-oxido-8-methylnon)-3,7-dimethylxanthine (inventive compound no. 2548R). To a suspension of magnesium (2.74 g, 140 mmol) and a crystal of iodine in tetrahydrofuran (15 mL) was added (R)-citronellyl bromide (5.0 g, 22.8 mmol) in tetrahydrofuran (10 mL) over 30 minutes and the reaction stirred for a further 30 minutes after the addition was complete. The solution was added via a canula over 5 minutes to a suspension of paraformaldehyde (1.80 g, 60.0 mmol) in tetrahydrofuran (15 mL) and stirred at 25° C. for 6 hours. Saturated armnonium chloride (40 mL) was added and extracted with diethyl ether (2×30 mL). The combined organic extracts were dried (magnesium sulfate) and the solvent evaporated to yield 3.25 g (84% yield) 4-(R)-methyl-8-methylnonyl-7-enyl alcohol as a clear liquid.

To a solution of 4-(R)-methyl-8-methylnonyl-7-enyl alcohol (3.25 g, 19.1 mmol) in dichloromethane (50 mL) at 0° C. is added methanesulfonyl chloride (2.29 g, 20.0 mmol) followed by triethylamine (3.04 g, 30.0 mmol). After stirring for 10 minutes at 0° C., the reaction was allowed to warm to 25° C. and stirred for 3 hours. The reaction was poured into water (50 mL), separated and washed with dichloromethane (50 mL). The organic portions were combined, dried using magnesium sulfate and the solvent evaporated to give the 1-methanesulfonyl-4-(R)-methyl-8-methylnon-7-ene as a yellow oil which was used without further purification.

To a suspension of sodium theobromine (4.05 g, 20.0 mmol) in dimethylsulfoxide (50 mL) was added 1-methanesulfonyl-4-(R)-methyl-8-methylnon-7-ene and the reaction stirred for 16 hours at 60° C. The mixture was then poured into water (100 mL) and extracted with ethyl acetate (100 mL, 2×50 mL). The organic portions were combined, dried using magnesium sulfate and the solvent evaporated to give a residue which was purified by column chromatography using ethyl acetate/hexane to yield 1.70 g (28% yield) 1-(4-(R)-Methyl-8-methylnon-7-enyl)-3,7-dimethylxanthine (inventive compound no. 2536R) as a white solid.

A solution of 1-(4-(R)-Methyl-8-methylnon-7-enyl)-3,7-dimethylxanthine (0.48 g, 1.44 mmol), 4-methylmorpholine-N-oxide (0.51 g, 4.38 mmol) and potassium osmate dihydrate (5 mg, 0.015 mmol) in acetone/water 1:2 (9 mL) was stirred for 16 hours. Water (10 mL) and sodium sulfite (1 g) were added and the reaction mixture stirred for 1 hour. The reaction mixture was extracted with dichloromethane (3×30 ml) using dried magnesium sulfate and the solvent evaporated to yield 0.51 g (97% yield) 1-(4-(R)-Methyl-7,8-dihydroxy-8-methylnonyl)-3,7-dimethylxanthine (inventive compound no. 2537R) as a colorless oil.

1-(4-(R)-Methyl-7,8-dihydroxy-8-methylnonyl)-3,7-dimethylxanthine (0.29 g, 0.80 mmol) was stirred with hydrogen bromide (1.00 mL of a 30% solution in acetic acid, 2.40 mmol) for 4 hours. The mixture was then added over 10 minutes to water (10 mL), ice (5 g) and sodium bicarbonate (2 g) and stirred for 30 minutes. The reaction mixture was extracted with dichloromethane (2×15 mL), the combined organic phases dried using magnesium sulfate and the solvent evaporated to obtain a residue of 1-(4-(R)-methyl-7-acetoxy-8-bromo-8-methylnonyl)-3,7-dimethylxanthine.

Without further purification, this crude residue was taken up in methanol (5 mL) and treated with a solution of sodium methoxide (prepared from sodium (0.020 g, 0.85 mmol) and 5 mL methanol). After 40 minutes, the reaction was added to water (10 mL) and extracted with dichloromethane (3×10 mL). The organic portions were combined, dried and evaporated to yield 0.24 g (86% yield) of 1-(4-(R)-Methyl-7,8-oxido-8-methylnonyl)-3,7-dimethylxanthine (inventive compound no. 2548R) as a white solid.

EXAMPLE 42

This example illustrates a synthesis of 1-(3,7-Dimethyl-2,3,6,7-dioxidoctyl)-3,7-dimethylxanthine (inventive compound no. 2552). Sodium hydride (95%) (0.28 g, 12 mmol) was added to a solution of theobromine (2.16 g, 12 mmol) in dimethylsulfoxide (50 mL). After 20 minutes of stirring, geranyl bromide (2.17 g, 10 mmol) was added. After 6 hours of stirring at room temperature, the reaction mixture was warmed to 60° C. for 3 hours and then poured into a separatory funnel containing 150 mL of water and extracted with dichloromethane (5×75 mL). The organic extracts were combined, washed with water (50 mL) and brine (50 mL), dried over anhydrous magnesium sulfate and concentrated under reduced pressure. The crude product obtained was further purified by flash chromatography over silica gel using 30% acetone/petroleum ether eluant to yield 2.1 g (66.5% yield) 1-(Geranyl)-3,7-dimethylxanthine (inventive compound no. 2545).

A solution of 1-(geranyl)-3,7-dimethylxanthine (0.316 g, 1 mmol), and m-chloroperoxybenzoic acid (1.035 g; 3 mmol) (50% by wt) in dichloromethane (15 mL) was stirred for 6 hours. The reaction mixture was diluted with 80 mL of dichloromethane and washed successively with 20% aqueous sodium sulphite solution (20 mL), saturated sodium hydride $CO_3$ solution (20 mL), water and brine solutions. The organic layer was dried over anhydrous magnesium sulfate and concentrated under reduced pressure. The crude product obtained was further purified by flash chromatography over silica gel using a 30% acetone/hexane eluant to yield 0.25 g (72% yield) 1-(3,7-dimethyl-2,3,6,7-dioxidoctyl)-3,7-dimethylxanthine.

EXAMPLE 43

This example illustrates a synthesis of 1-(12,13-Oxidotridecyl)-3,7-dimethylxanthine (inventive compound no. 2562). To a suspension of magnesium (4.12 g, 172 mmol) and a crystal of iodine in tetrahydrofuran (40 mL) was added 10-undecenyl bromide (8.00 g, 34.3 mmol) in tetrahydrofuran (30 mL) over 30 minutes and the reaction stirred for a further 30 minutes after the addition was complete. The solution was added via a canula over 5 minutes to a solution of ethylene oxide (2.65 g, 60.0 mmol) in tetrahydrofuran (30 mL) and stirred at 25° C. for 16 hours.

Saturated ammonium chloride (100 mL) and 1M hydrogen chloride (200 mL) were added and extracted with diethyl ether (2×200 mL). The combined organic extracts were dried (magnesium sulfate) and evaporated to give a residue which was distilled at 1.5 mm Hg to afford 12-tridecenyl alcohol as a clear liquid (4.11 g, 61%, b.p. 98°–101° C.).

To a solution of 12-tridecen-1-ol (2.11 g, 10.7 mmol) and carbon tetrabromide (4.37 g, 13.1 mmol) in dichloromethane (15 mL) at 0° C. was added triphenyl phosphine (3.45 g, 13.1 mmol) in portions over 5 minutes. After stirring for 1.5 hours at 25° C. the solvent was evaporated and the residue extracted with hexane (3×30 mL), filtering off any solids. The solvent was evaporated to afford 12-tridecenyl bromide as a clear oil which was used without further purification.

To a suspension of sodium theobromine (2.22 g, 11.0 mmol) in dimethylsulfoxide (25 mL) was added 12-tridecenyl bromide and the reaction stirred for 16 hours at 60° C. The mixture was then poured into water (80 mL) and extracted with dichloromethane (3×50 mL). The combined organic portions were washed with water (3×100 mL), dried using magnesium sulfate, and evaporated to give a gummy residue. Purification by column chromatography using an ethyl acetate/hexane eluant yields 1.89 g (50% yield) 1-(12-Tridecenyl)-3,7-dimethylxanthine (inventive compound no. 2555) as a white solid.

A solution of 1-(12-Tridecenyl)-3,7-dimethylxanthine (1.39 g, 3.86 mmol), 4-methylmorpholine-N-oxide (1.36 g, 11.6 mmol) and potassium osmate dihydrate (14 mg, 0.040 mmol) in acetone/water 1:2 (25 mL) was stirred for 16 hours. Water (25 mL) and sodium sulfite (2 g) were added and the reaction mixture stirred for 1 hour. The reaction mixture was extracted with dichloromethane (3×50 mL), dried using magnesium sulfate and the solvent evaporated to yield 1.25 g (82%) of 1-(12,13-dihydroxytridecyl)-3,7-dimethylxanthine (inventive compound no. 2556) as a white solid.

1-(12,13-Dihydroxy-tridecyl)-3,7-dimethylxanthine (1.15 g, 2.92 mmol) was stirred with hydrogen bromide (2.84 mL of a 30% solution in acetic acid, 8.76 mmol) for 2 hours. The mixture was then added over 10 minutes to water (20 mL), ice (15 g) and sodium bicarbonate (5 g) and stirred for 30 minutes. The reaction mixture was extracted with dichloromethane (2×50 mL), and the combined organic phases were dried using magnesium sulfate and the solvent evaporated to obtain a residue of 1-(12-acetoxy-13-bromotridecyl)-3,7-dimethylxanthine. Without further purification, this crude residue was taken up in methanol (5 mL) and treated with a solution of sodium methoxide (prepared from sodium, 0.069 g, 3.00 mmol, and 5 mL methanol). After 40 minutes, the reaction mitxure was added to water (15 mL) and extracted with dichloromethane (3×30 mL). The organic portions were combined, dried and the solvent evaporated to yield 1.00 g (91% yield) 1-(12,13-Oxidotridecyl)-3,7-dimethylxanthine (inventive compound no. 2562) as a white solid.

EXAMPLE 44

This example illustrates a synthesis of 1-(7,8-cis-Oxidodecyl)-3,7-dimethylxanthine (inventive compound no. 2563). 7-cis--Decenal (Johnson Matthey Catalog Co., 10.00 g, 6.5 mmol) was added dropwise to a stirring suspension of sodium borohydride (2.45 g, 65 mmol) in ethanol (100 mL) at 0° C. The ice bath was allowed to melt and stirring continued for 3 hours. Ammonium chloride solution (sat., 60 mL) was added with water (50 mL) and the mixture was extracted with dichloromethane (3×100 mL). The organic extracts were combined and washed with water (50 mL) and brine (50 mL) and dried (sodium sulfate). Evaporation of solvent gave the alcohol 7-cis--decen-1-ol as a colorless oil (9.19 g, 91% yield).

7-cis-Decen-1-ol (5.00 g, 32.1 mmol) and methanesulfonyl chloride (2.5 mL, 3.70 g, 32.3 mmol) in dichloromethane (150 mL) at 0° C. is treated dropwise with triethylamine (6.7 mL, 4.9 g, 48 mmol), after which time, the ice bath is allowed to melt. After stirring 3 hours at room temperature, the reaction was poured into a separatory funnel containing saturated sodium bicarbonate solution (50 mL) and dichloromethane (50 mL). The layers were separated and the aqueous layer washed with dichloromethane (2×50 mL). The organic layers were combined, washed with hydrogen chloride solution (50 mL, 1%), water (50 mL), and brine (40 mL), then dried (sodium sulfate). The solvent was removed to yield 6.97 g (92%) 7-cis-decene-1-methanesulfonate as a yellow oil. The mesylate was used in the next step without further purification.

1-Sodiotheobromine (6.00 g, 29.7 mmol) and 7-cis-decene-1-methanesulfonate (6.97 g, 29.7 mmol) were stirred in dimethylsulfoxide (60 mL) for 15 hours, then at 80° C. for 3 hours, then cooled. The reaction mixture was poured into water (100 mL) and extracted with dichloromethane (3×60 mL). The organic layers were combined and washed with water (60 mL) and brine (50 mL) and dried using sodium sulfate. Addition of ether and petroleum ether to the residue precipitates a white solid, yielding 3.25 g (32% yield) 1-(7-cis-Decenyl)-3,7-dimethylxanthine (inventive compound no. 2560).

1-(7-cis-Decenyl)-3,7-dimethylxanthine (0.50 g, 1.6 mmol) in dichloromethane (25 mL) was added to a solution of sodium bicarbonate (1.30 g, 16 mmol) in water (20 mL). 4-Chloroperoxybenzoic acid (326 mg, or 652 mg of a 50% mixture, 1.9 mmol) was added and the reaction mixture stirred at room temperature for 20 hours. Sodium sulfite (100 mg) was added to quench residual MCPBA. To the reaction mixture was added dichloromethane (30 mL) and water (20 mL). The organic layer was separated and the aqueous layer washed with dichloromethane (3×30 mL). The organic layers were combined and washed with saturated sodium bicarbonate solution (20 mL), and brine (20 mL) and then dried using sodium sulfate. Removal of solvent results in an oil which solidifies upon standing. The white solid was washed with ether and dried to yield 460 mg (86% yield) of 1-(7,8-cis-Oxidodecyl)-3,7-dimethylxanthine.

EXAMPLE 45

This example illustrates a synthesis of 1-(13,14-Oxidotetradecyl)-3,7-dimethylxanthine (inventive compound no. 3503). To a suspension of magnesium (1.86 g, 77.2 mmol) and a crystal of iodine in THF (20 mL) was added 10-undecenyl bromide (6.00 g, 25.8 mmol) in THF (14 mL) over 40 minutes and the reaction stirred for a further 30 minutes after the addition was complete. The solution was added via a canula over 50 minutes to a suspension of copper iodide (0.50 g, 2.58 mmol) and 1-bromo-3-chloropropane (3.84 mL, 38.7 mmol) in THF (20 mL) and stirred at 25° C. for 16 hours. Sulfuric acid (1.0M, 50 mL) was added, extracted with diethyl ether (2×60 mL) and the organic solvent dried using magnesium sulfate and evaporated. The residue was distilled at 0.25 mmHg to obtain 3.06 g (51% yield, b.p. 98°–100° C.)13-tetradecenyl chloride as a colourless liquid.

To a suspension of sodium theobromine (1.82 g, 8.68 mmol) in dimethylsulfoxide (20 mL) was added 13-tridecenyl chloride and the reaction stirred for 48 hours at 50° C. The mixture was then poured into water (60 mL) and extracted with ethyl acetate (3×50 mL). The organic portions were combined, dried using magnesium sulfate and evaporated to give a cream solid. Recrystallization from hot hexane yields 2.38 g (73% yield) 1-(13-Tetradecenyl)-3,7-dimethylxanthine as a white solid.

A solution of 1-(13-Tetradecenyl)-3,7-dimethylxanthine (2.00 g, 5.35 mmol), 4-methylmorpholine-N-oxide (2.72 mL, 60% wt in water, 15.8 mmol) and potassium osmate dihydrate (21 mg, 0.05 mmol) in acetone/water 3:1 (80 mL) was stirred for 16 hours. Water (100 mL) and sodium sulfite (1 g) were added and stirred for 1 hour. The reaction mixture was extracted with dichloromethane (3×100 mL) and the organic phase dried (magnesium sulfate) and evaporated to yield 2.10 g (96% yield) 1-(13,14-Dihydroxytetradecyl)-3,7-dimethylxanthine as a white solid.

1-(13,14-Dihydroxytetradecyl)-3,7-dimethylxanthine (0.80 g, 1.96 mmol) was stirred with HBr (1.94 mL of a 30% solution in acetic acid, 5.88 mmol) for 2 hours. The mixture was then added over 10 minutes to water (20 mL), ice (15 g) and NaHCO3 (3.5 g) and stirred for 30 minutes. The reaction mixture was extracted with dichloromethane (2×50 mL), the combined organic phases were dried using magnesium sulfate and the solvent was evaporated to obtain a residue of 1-(13-acetoxy-14-bromotetradecyl)-3,7-dimethylxanthine.

Without further purification, this crude residue was taken up in methanol (5 mL) and treated with a solution of sodium methoxide (prepared from sodium (0.069 g, 3.00 mmol) and 5 mL methanol). After 40 minutes, the reaction was added to water (15 mL) and extracted with dichloromethane (3×30 mL). The organic portions were combined, dried and the solvent evaporated to yield 0.71 g (93% yield) of 1-(13,14-Oxidotetradecyl)-3,7-dimethylxanthine as a white solid.

EXAMPLE 46

This example illustrates a synthesis of 1-(16,17-Oxidoheptadecyl)-3,7-dimethylxanthine (inventive compound no. 3516). To a suspension of magnesium (3.10 g, 129 mmol) and a crystal of iodine in THF (10 mL) was added 10-undecenyl bromide (6.00 g, 25.8 mmol, available from MTM) in THF (20 mL) over 40 minutes and the reaction stirred for a further 30 minutes after the addition was complete. The solution was added via a canula over 50 minutes to a suspension of copper iodide (0.50 g, 2.58 mmol) and 1-bromo-6-chloro hexane (6.00 mL, 40.0 mmol) in THF (20 mL) and stirred at 25° C. for 16 hours. Sulfuric acid (1.0M, 50 mL) was added, extracted with diethyl ether (2×60 mL) and the organic solvent dried using magnesium sulfate and the solvent subsequently evaporated. The residue was distilled at 0.75 mmHg to yield 1.78 g (25% yield, b.p. 130°–135° C.) 16-heptadecenyl chloride as a colourless liquid.

To a suspension of sodium theobromine (2.02 g, 10.0 mmol) in dimethylsulfoxide/tetrahydrofuran (2:1, 30 mL) was added 16-heptadecenyl chloride and the reaction stirred for 16 hours at 60° C. The mixture was poured into water (75 mL) and extracted with ethyl acetate (3×75 mL). The organic portions were combined, dried using magnesium sulfate, and the solvent evaporated to give a cream solid. Recrystallization from hot hexane yields 2.31 g (85% yield) 1-(16-Heptadecenyl)-3,7-dimethylxanthine as a white solid.

A solution of 1-(16-Heptadecenyl)-3,7-dimethylxanthine (1.50 g, 3.60 mmol), 4-methylmorpholine-N-oxide (1.83 mL, 60% wt in water, 10.6 mmol) and potassium osmate dihydrate (16 mg, 0.04 mmol) in acetone/water/ tetrahydrofuran (10:7:5, 110 mL) was stirred for 60 hours. Water (100 mL) and sodium sulfite (1 g) were added and the reaction mixture stirred for 1 hour. The reaction mixture was extracted with dichloromethane (2×100 mL) and the organic phase dried using magnesium sulfate and the solvent evaporated to afford a cream solid. Recrystallization from hot ethyl acetate yields 1.31 g (81% yield) of 1-(16,17-dihydroxyheptadecyl)-3,7-dimethylxanthine (inventive compound no. 3514).

1-(16,17-Dihydroxyheptadecyl)-3,7-dimethylxanthine (1.10 g, 2.44 mmol) was stirred with HBr (3.50 mL of a 30% solution in acetic acid, 17.1 mmol) for 4 hours. The mixture was then added over 10 minutes to water (50 mL),and NaHCO3 (10 g) and stirred for 30 minutes. The reaction mixture was extracted with dichloromethane (3×30 mL), the combined organic phases were dried using magnesium sulfate and the solvent was evaporated to obtain a residue of 1-(16-acetoxy-17-bromoheptadecyl)-3,7-dimethylxanthine.

Without further purification, 1-(1 6-acetoxy-17-bromoheptadecyl)-3,7-dimethylxanthine was taken up in methanol (5 mL) and treated with a solution of sodium methoxide (prepared from sodium (0.074 g, 3.20 mmol) and 5 mL methanol). After 40 minutes, the reaction mixture was added to water (15 mL) and extracted with dichloromethane (3×30 mL). The organic portions were combined, dried and the solvent evaporated to 1.00 g (95% yield) 1-(16,17-Oxidoheptadecyl)-3,7-dimethylxanthine as a white solid.

EXAMPLE 47

This example illustrates a synthesis of N-(5,6-Oxidohexylamido)glutaric acid, methyl ester (inventive compound no. 1301). Sodium hydride (425 mg, 17.7 mmol) was added to a solution of glutarimide (2.00 g, 7.7 mmol) in dimethyl sulfoxide (40 mL). After 20 minutes of stirring, 6-bromo-1-hexene (2.90 g, 17.7 mmol) was added. After 20 hours of stirring, the reaction was poured into a separatory funnel containing 100 mL water and extracted with dichloromethane (4×50 mL). The organic portions were combined, washed with water (50 mL) and brine (50 mL) and dried to yield 2.92 g (85% yield) 1-(5-Hexenyl)glutarimide (inventive compound no. 1600) as a colorless oil.

A solution of 1-(5-hexenyl)glutarimide (1.50 g, 7.7 mmol), 4-methylmorpholine-N-oxide (1.08 g, 9.2 mmol) and osmium tetraoxide (3 drops of a 2.5% sol. by wt. in tert-butanol) in acetone (10 mL) and water (10 mL) was stirred for 69 hours. Following addition of 10 mL of a saturated solution of sodium dithionite and a further 15 minutes of stirring, the reaction was extracted with 25% ethanol/dichlormethane (4×50 mL). The organic layers were combined and dried (sodium sulfate) and evaporated to a thick oil which was purified by chromatography using silica and an ethyl acetate eluant to yield 1.29 g (73% yield) N-(5,6-Dihydroxyhexyl)glutarimide (inventive compound no. 1603) as a colorless oil.

To 1-(5,6-dihydroxyhexyl)glutarimide (1.29 g, 5.6 mmol) was added 30% hydrogen bromide-acetic acid (3.4 mL) and the resulting mixture stirred until all of the solid had dissolved (45 minutes). The solution was poured carefully over a mixture of sodium bicarbonate (6.5 g), ice water (40 mL), and dichloromethane (40 mL). After carbon dioxide evolution had subsided, the organic layer was separated, and the aqueous layer extracted with dichloromethane (2×30 mL). The combined organic layers were dried over magnesium sulfate and the solvent was evaporated under vacuum to yield 1.73 g (92% yield) 1-(5-Acetoxy-6-bromohexyl)

glutarimide as a viscous oil which was dissolved in methanol (5 mL). A 0.7M sodium methoxide in methanol solution (6 mL) was added all at once. After stirring for 15 minutes, the solution was treated with water (20 mL) and then extracted with dichloromethane (3×15 mL). The combined extracts were dried over magnesium sulfate and the solvents were evaporated under vacuum. The residue was chromatographed (80% ethyl acetate/20% petroleum ether) to yield 256 mg (18% yield) N-(5,6-Oxidohexylamido)glutaric acid, methyl ester as a colorless oil.

EXAMPLE 48

This example illustrates the effects of inventive compound no. 1541 as hair growth stimulant in nude mice. In a procedure similar to that used in a commercial model for predicting human hair-growing ability of minoxidil, nu/nu (nude) mice were painted twice daily for 16 days on the right flank with compound no. 1541 using sterile applicators. Researches handled the mice under a laminar flow hood with applicator, wearing face mask and sterile gloves.

After 16 days, one mouse was sacrificed by cervical dislocation and skin biopsies taken from the treated areas of the shoulder/flank and the non-treated area of the dorsal pelvis (rump). Specimens were placed in 10% buffered formalin solution.

A microscopic analysis of the skin biopsies confirmed that follicles in the treated areas had hair shafts which sometimes exit to the surface. There were mild accumulations of mixed inflammatory cells in the dermis. In contrast, hair follicles from untreated skin biopsies were smaller/shorter and less often extend into the subcutis. Hair shafts were rarely seen. A few mixed inflammatory cells were in the dermis in the untreated areas as well.

The treated sections had more normal appearing hair follicles than the untreated sections. In addition, numerous hair shafts were seen exiting follicles in the treated sections.

Six weeks following treatment, a second mouse was euthanatized and biopsied the same as previous mouse after 16 days.

A microscopic examination of the skin biopsies taken after six weeks confirmed hair loss. The biopsies showed slightly more acanthosis (epidermal hyperplasta) in treated areas and slightly straighter superficial portions of follicles with less curling of hair shafts. In treated sections, the subcutis contained active anagen bulbs located deeply in the subcutis. The follicles were slightly dilated. Scattered mast cells, lymphocytes and a few neutrophils were present. One section had a few increased cells in the subcutis.

These data show that 1541, when applied topically, can be used to treat or prevent baldness or allopecia.

EXAMPLE 49

This example illustrates the effects of inventive compounds nos. 1105, 1114, 1413, 1439, 1594, 2518, 2548R, 2548S, 2562 and 3503 as effective inhibitors of IL-2 induced proliferation of thymocytes. Single cell suspensions of thymus gland cells obtained from 4–6 week old mice were prepared. Two-hundred thousand cells were plated into individual wells of flat-bottom 96-well plates in RPMI-1640–10% FCS medium. The invention compounds were then added to the wells at varying concentrations and the cells incubated for 1–2 hours at 37° C.

Following this pre-incubation a mixture of Concanavalin A (ConA) and Interleukin-2 (IL2) was added to the experimental wells at a final concentration of (0.25 ug/ml ConA)/(20 ng/ml IL2). Appropriate positive and negative controls were set up on each plate. Each variable was set up in quadruplicate.

The plates were incubated for 4 days at 37° C. in a humidified $CO_2$ incubator. On day 4 the wells were pulsed with 1 $\mu$Ci of tritiated thymidine(3H-TdR) and the plates incubated for an additional 4 hours. The plates were then harvested and the incorporation of 3H-TdR was determined in a liquid scintillation counter. From the CPM obtained from each experimental well an IC-50 for each inventive compound tested was determined. Therefore, a lower reported IC-50 value is indicative of greater inhibition of IL-2-induced proliferation of thymocytes. Table II illustrates IC-50 values (in $\mu$M) for inventive compounds inhibiting proliferation at very low concentrations of compound.

TABLE II

| Inventive Compound | IC-50 ($\mu$M) |
|---|---|
| 2562 | 3.1 |
| 2518 | 3.4 |
| 2548S | 4.6 |
| 2548R | 7.5 |
| 1413 | 7.7 |
| 1439 | 8.0 |
| 1105 | 8.5 |
| 1594 | 8.5 |
| 1114 | 10.0 |
| 3503 | 10.0 |

These data show that the illustrated inventive compounds are effective therapeutic agents for the treatment or prevention of autoimune disorders or inflammatory diseases.

EXAMPLE 50

This example illustrates the effects of inventive compounds nos. 1114, 1413, 1560, 1565, 1594, 2518, 2548R, 2548S and 3503 as effective inhibitors of normal human bone marrow stromal cells (MSC) proliferation in response to Platelet Derived Growth Factor BB (PDGF B) and IL-1α (50 and 10 ng/ml, respectively). Maximum proliferation occurs when both PDGF B and IL-1α are present, hence a combination of both were used in the following assay.

MSC were obtained and malintained in exponential growth, released from a growth plate with trypsin and plated into 96 well tissue culture plates in the presence of Fibroblast Growth Factor (FGFβ) for 48 hours. Growth media were removed and the cells were washed once with serum free media. The cells were then incubated 20–24 hours in serum free media.

After incubation, inventive compounds were added to the cells at the appropriate concentration and then the cells again incubated for 1 hour. PDGF B and IL-1α were added to the cells along with 3H-thymidine and the cells again incubated for an additional 24 hours.

After 24 hours of incubation, the cells were then harvested to assess incorporation of $^3$H-thymidine into DNA (proliferation). From each harvested cell culture, an IC-50 for each inventive compound tested was determined. Therefore, a lower reported IC-50 value is indicatilve of greater activity of the invention compounds in inhibiting MSC proliferation. Table III illustrates IC-50 values (in $\mu$M) for invention compounds inhibiting MSC proliferation at very low concentrations of compound.

TABLE III

| Inventive Compound | IC-50 (μM) |
|---|---|
| 1413 | 3.7 |
| 1114 | 5.1 |
| 2548S | 5.9 |
| 1560 | 6.6 |
| 2548R | 8.7 |
| 1594 | 14.0 |
| 3503 | 14.0 |
| 2518 | 16.7 |
| 1565 | 17.0 |
| 1539 | 18.0 |

These data illustrate the inventive compounds illustrated are usefule to treat or prevent restenosis and atheroscherosis.

EXAMPLE 51

Figure 1:
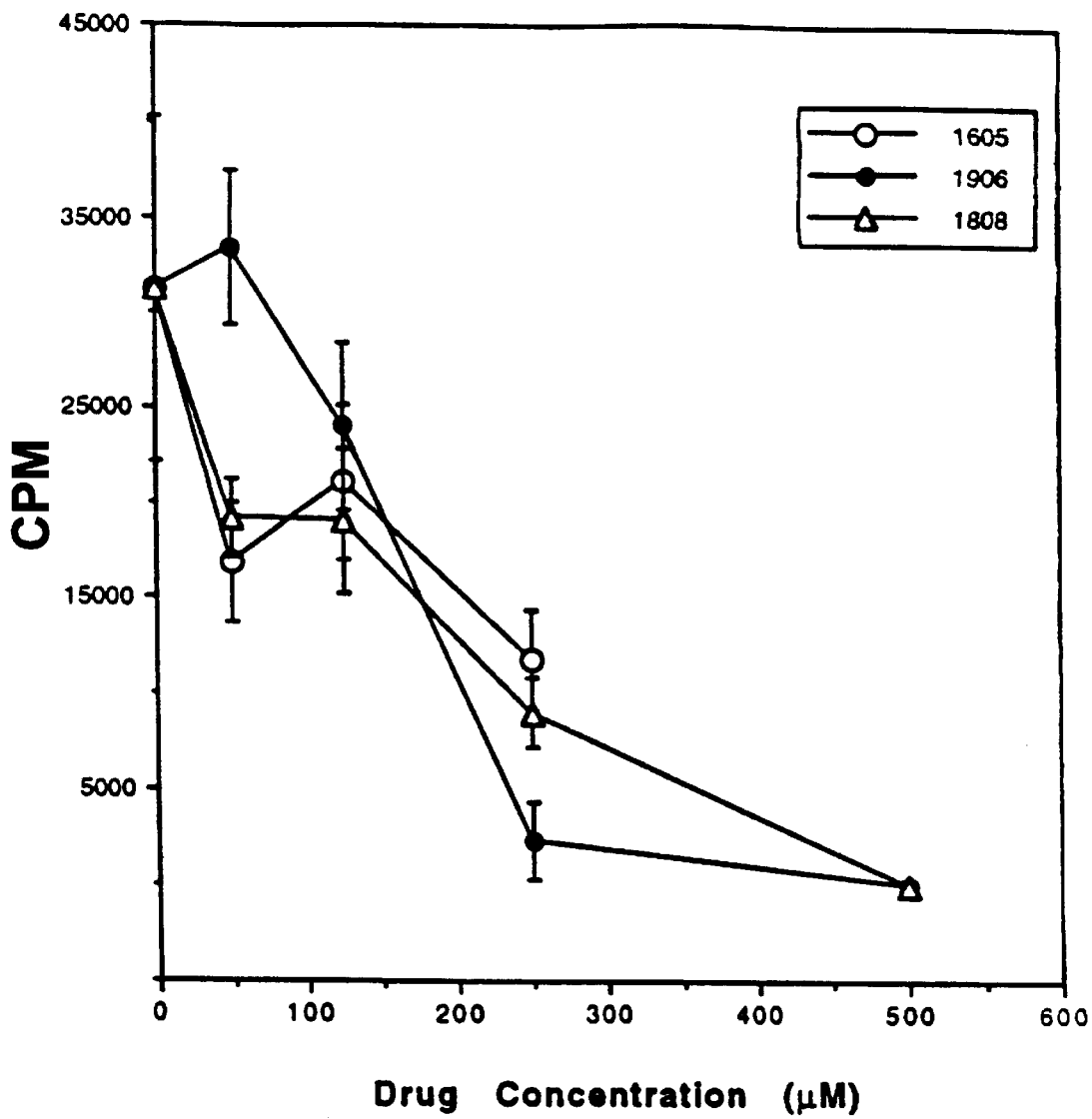
FIG. 1 shows a mixed lymphocyte reaction of three inventive compounds CT1605 (N-(5,6-oxidohexyl) glutarimide), 1808 ($N^3$-(5,6-oxidohexyl)-$N^1$-methyluracil), and 1906 ($N^3$-(5,6-oxidohexyl) $N^1$-methylthymine). The mixed lymphocyte reaction shows a proliferative response of PBMC (peripheral blood mononuclear cells) to allogeneic stimulation determined in a two-way mixed lymphocyte reaction. Each of the inventive compounds tested was effective (and more potent than PTX although not shown on this graph) in this immune modulating activity assay procedure.

This example illustrates the effects of inventive compounds nos. 1605, 1808 and 1906 as immune modulators in a mixed lymphocyte reaction. FIG. 1 shows the effects of three inventive compounds nos. 1605, 1808 and 1906. The mixed lymphocyte reaction shows a proliferative response of PBMC (peripheral blood mononuclear cells) to allogeneic stimulation determined in a two-way mixed lymphocyte reaction. Each of the inventive compounds tested demonstrated activity in this immune modulating activity assay procedure.

EXAMPLE 52

Figure 2:
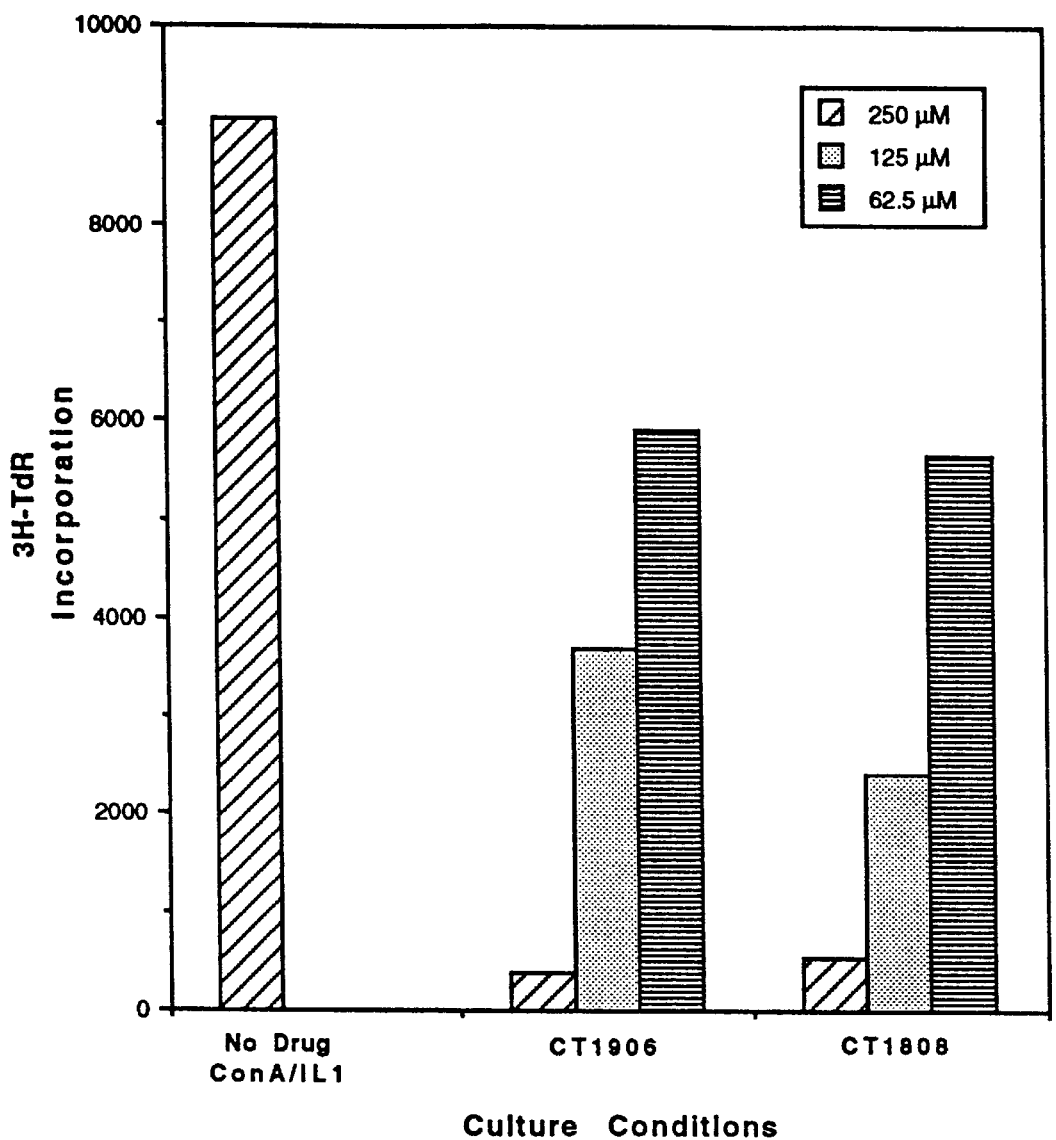
FIG. 2 shows a comparison of three dose levels of 1808 and 1906 and no drug control to inhibit thymocyte proliferation. The thymocytes were obtained from normal female Balb/C mice and stimulated with Concanavalin A (Con A) and/or interleukin-1 alpha (L-1α). Drugs were added to the cell cultures two hours before activation with Con A and/or IL-1α.

This example illustrates a comparison of three dose levels of inventive compounds nos. 1808 and 1906 and no drug control to inhibit thymocyte proliferation. The thymocytes were obtained from normal female Balb/C mice and co-stimulated with Concanavalin A (Con A) and/or IL-1α (interleukin-1 alpha). The thymuses were dissociated and plated into 96-well plates at a density of $2 \times 10^5$ cells/well. Dilutions of Con A and/or IL-1α were added to the wells and the cells were incubated for 4 days at 37° C. Drugs were added to the cell cultures two hours before activation with Con A and/or IL-1α. On day 4, the cells were pulsed with tritiated thymidine and allowed to incubate an additional 4 hrs. The cells were harvested and counted. As shown in FIG. 2, both compounds inhibited thymocyte proliferation is a dose-dependent fashion.

EXAMPLE 53

Figure 3:
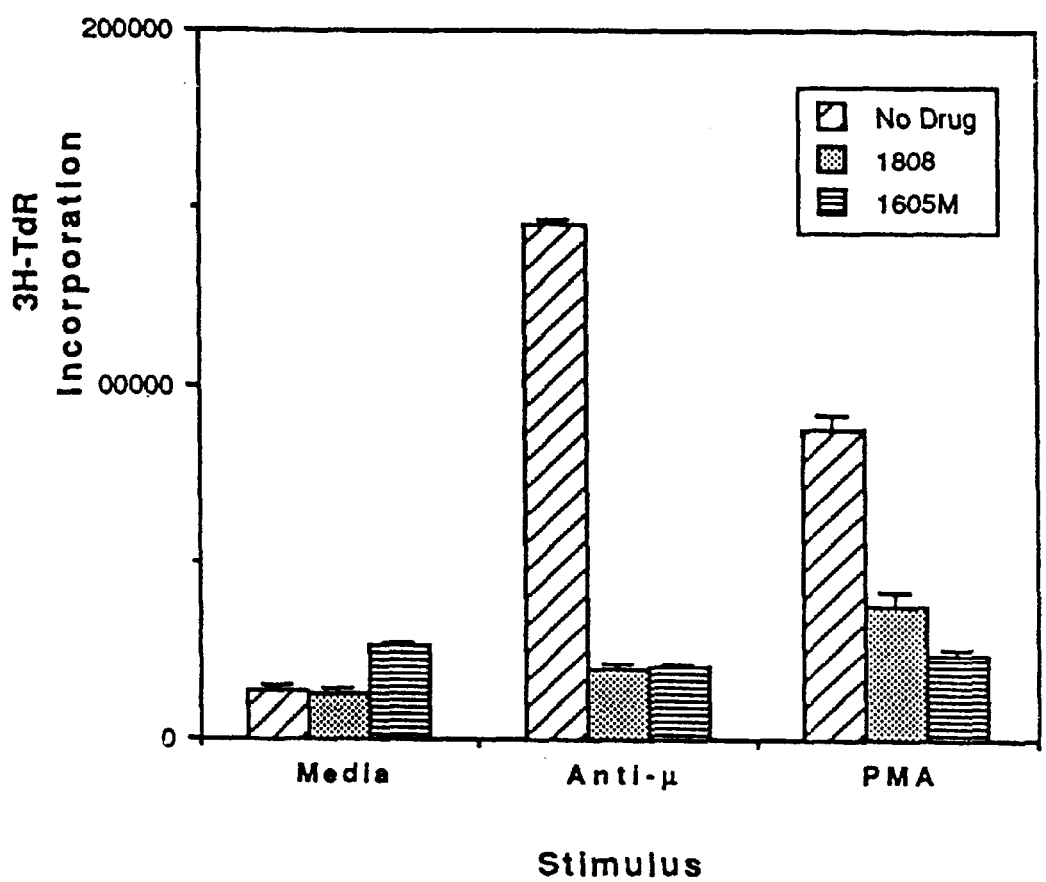
FIG. 3 shows a comparison of 1605 and 1808 on inhibition of B-cell proliferation. A Ramos C-cell tumor line was treated with 250 μM 1808 or 1605 for one hour prior to stimulation of proliferation with anti-mu antibody or phorbol myristic acid (PMA, 5 nM). One day later, proliferation was measured with tritiated thymidine. Both 1605 and 1808 inhibited proliferation in this model.

This example illustrates a comparison of inventive compounds nos. 1605 and 1808 for inhibition of B-cell proliferation. A Ramos B-cell tumor line was treated with 250 μM 1808 or 1605 for one hour prior to stimulation of proliferation with anti-mu antibody or PMA (5 nM). One day later, proliferation was measured with tritiated thymidine. As shown in FIG. 3, both compounds tested inhibited proliferation in this model.

EXAMPLE 54

Figure 4:
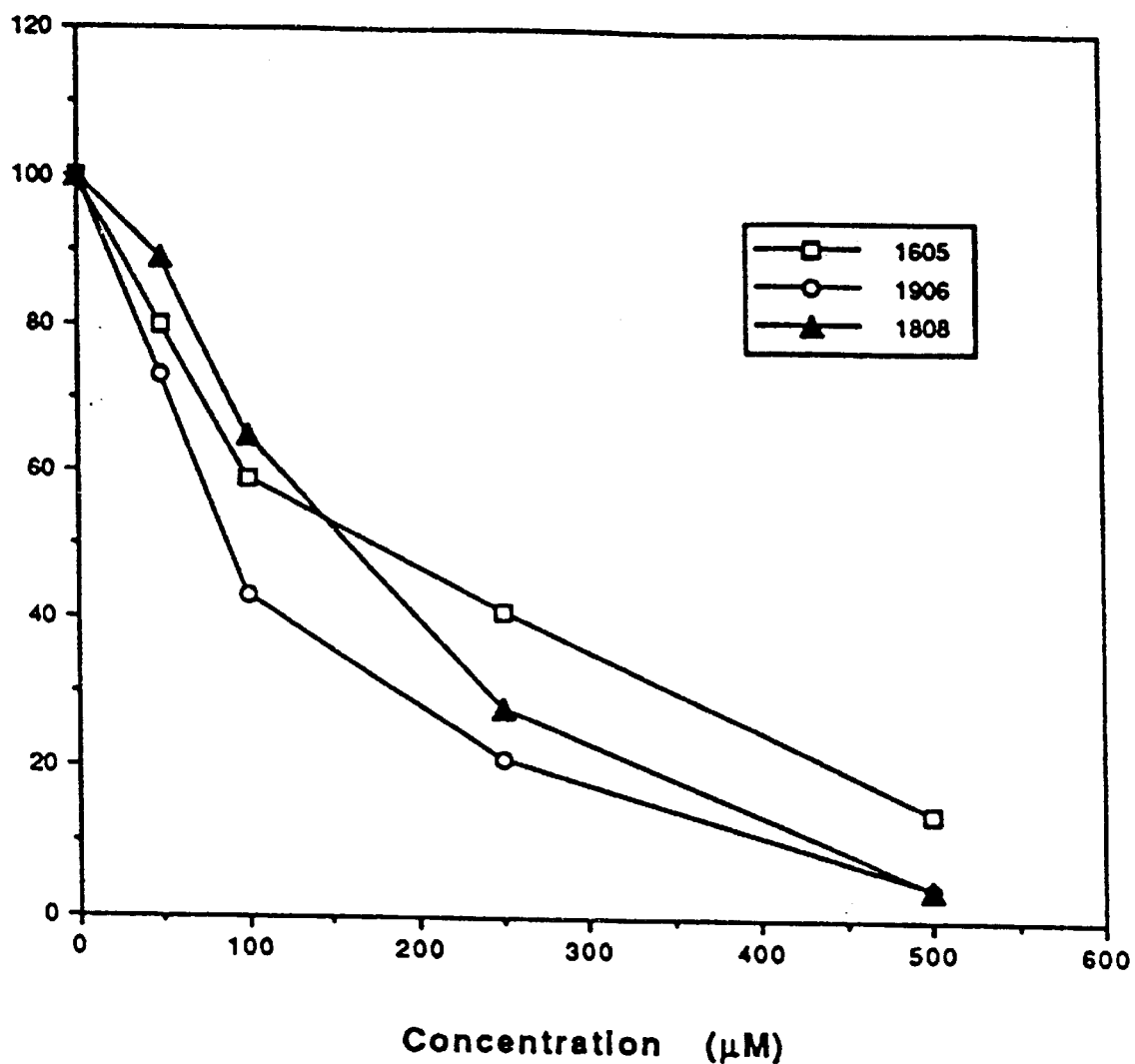
FIG. 4 shows a comparison of 1605, 1808 and 1906 on PDGF-induced (platelet derived growth factor) proliferation of human stromal cells. Human stromal cells were starved in serum-free media for 24 hours and then stimulated with 50 ng/ml of PDGF-BB. The drugs were added at various indicated concentrations one hour prior to PDGF stimulation. Tritiated thymidine was added for 24 hrs at the time of PDGF stimulation to measure cellular proliferation. Background counts were approximately 5% of control levels. All three drugs inhibited PDGF-induced stimulation in a dose response fashion.

This example illustrates a comparison of inventive compounds nos. 1605, 1808 and 1906 on PDGF-induced (platelet derived growth factor) proliferation of human stromal cells. Human stromal cells were starved in serum-free media for 24 hours and then stimulated with 50 ng/ml of PDGF-BB. The drugs were added at various indicated concentrations one hour prior to PDGF stimulation. Tritiated thymidine was added for 24 hours at the time of PDGF stimulation to measure cellular proliferation. Background counts were approximately 5% of control levels. As shown in FIG. 4, all three drugs inhibited PDGF-induced stimulation in a dose response fashion.

EXAMPLE 55

This example illustrates a comparison of the effects of inventive compounds nos. 1605, 1808 and 1906 to inhibit adhesion of U937 cells to activated human umbilical vein endothelial cells (HUVEC). HUVEC cells (4000/ well, seeded 72 hours in advance) were activated with 20 ng/ml of TNF-α for 12 hours. Drug was added to the HUVEC (except for controls) one hour prior to adding TNF-α. U937 cells, preloaded with the fluorescent dye BCECF, were added to each culture well and then washed twice with PBS. Cell adhesion was determined by measuring the fluorescence of adhering U937 cells on a fluorescence plate reader. As illustrated in FIG. 5, all three drugs showed a decrease in cell adhesion induced by TNF-α in a dose dependent fashion.

EXAMPLE 56

This example illustrates the effects of inventive compounds nos. 1605, 1808 and 1906 to inhibit cell surface expression of vascular cell adhesion molecule-1 (VCAM) in human umbilical vein endothelial cells (HUVEC). The HUVEC cells were stimulated with 20 ng/ml TNF-α for 20 hrs and then stained for immunofluorescence using a monoclonal antibody recognizing VCAM, followed by a goat anti-mouse antibody conjugated to phycoerythrin. The cells were analyzed for antibody binding using flow cytometry. FIG. 6 shows an analysis of mean relative fluorescence intensity of the HUVEC, as analyzed by flow cytometry. Mean fluorescence levels were decreased by all three drugs from the stimulated cells (TNF treatment, no drug).

EXAMPLE 57

Figure 7A:
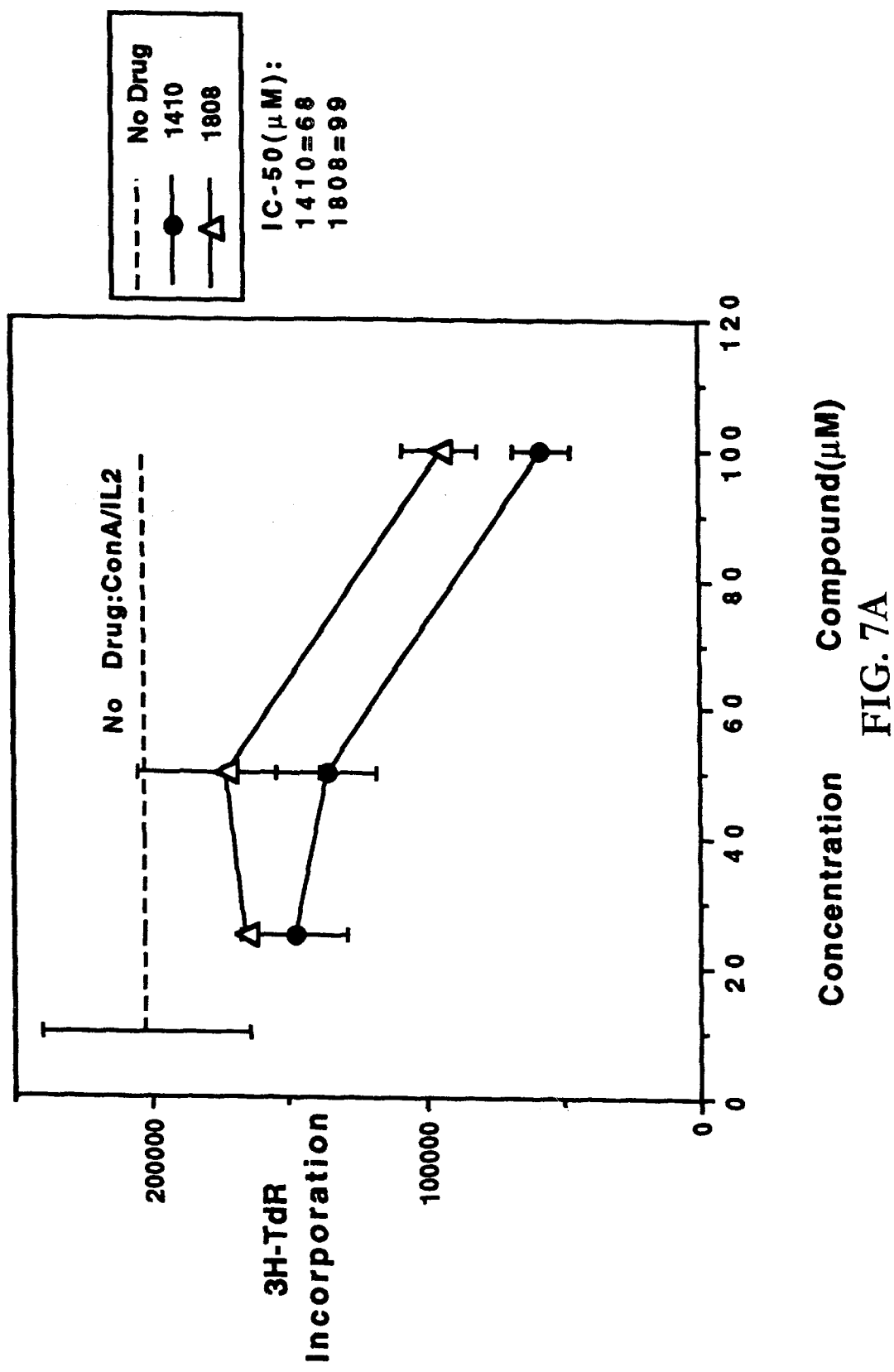
Figure 7B:
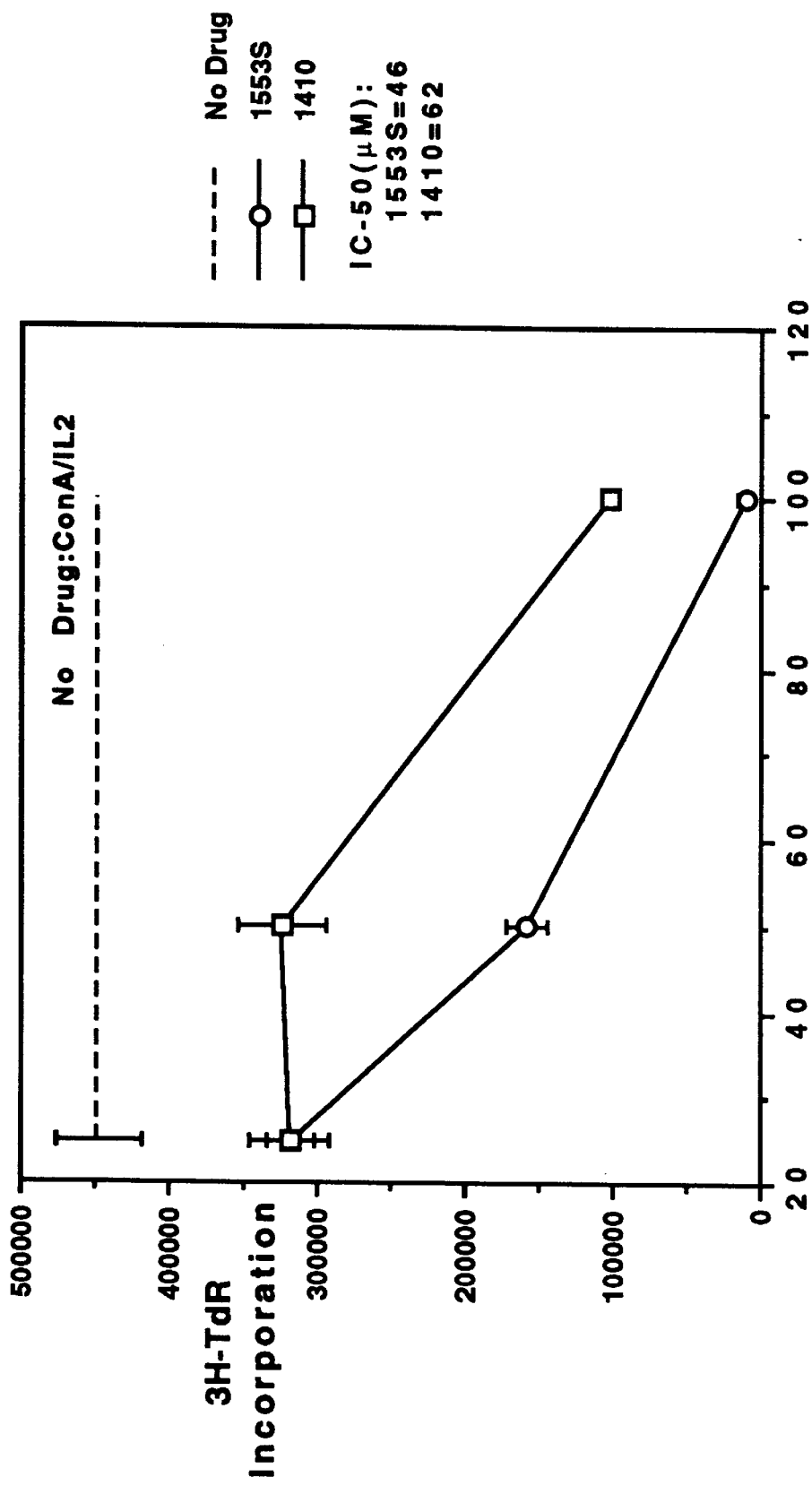
Figure 7C:
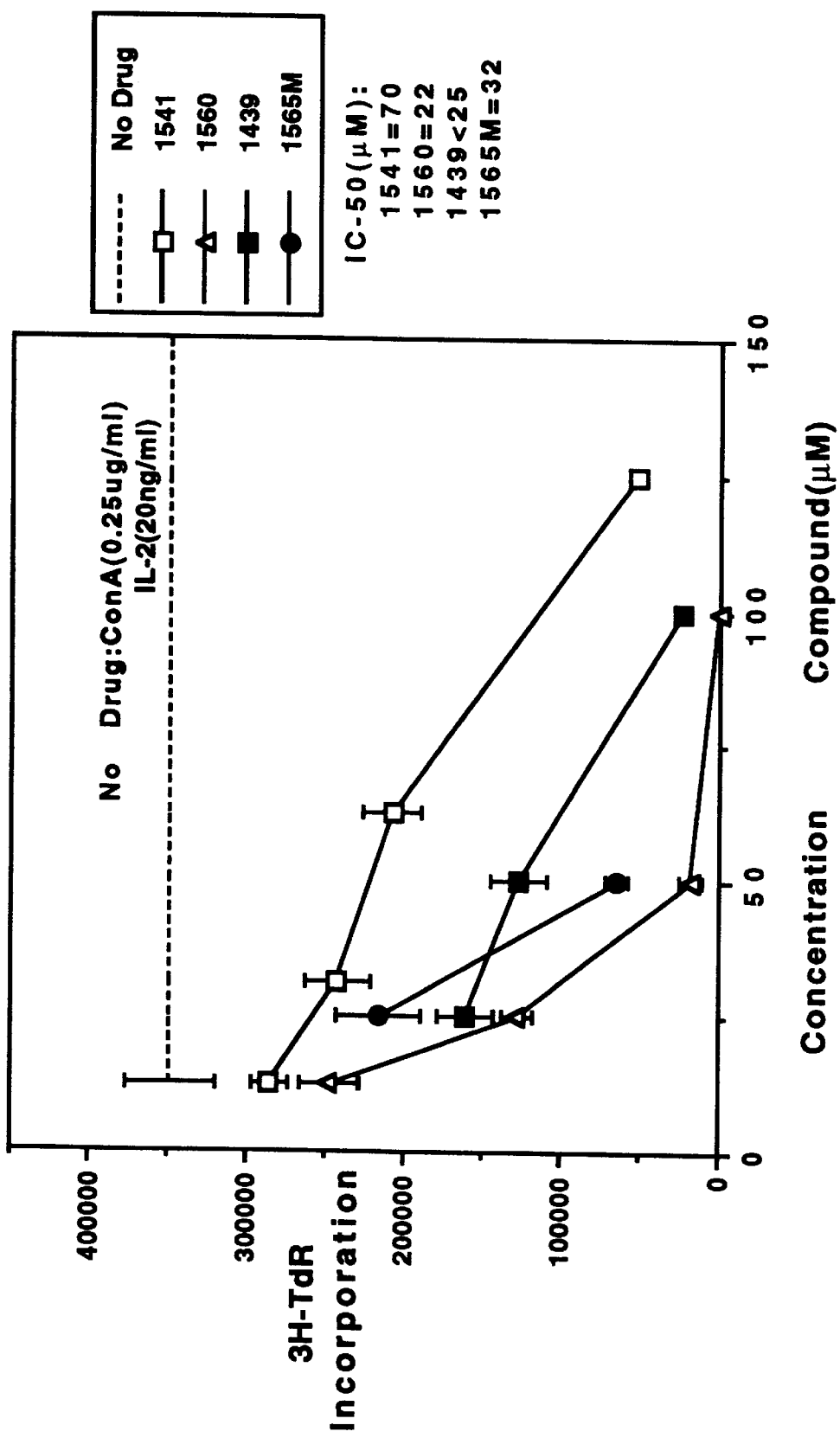
Figure 7D:
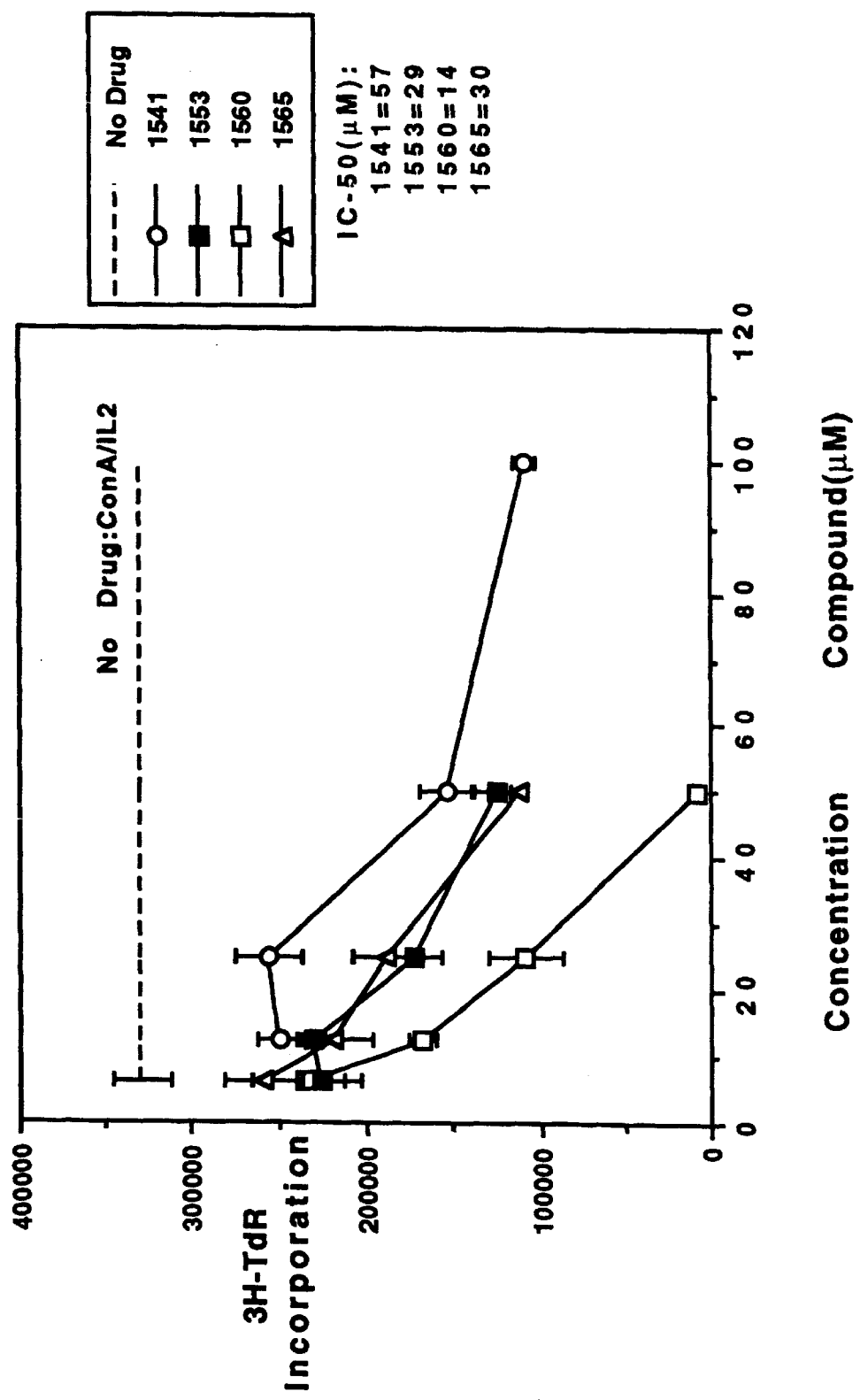
Figure 7E:
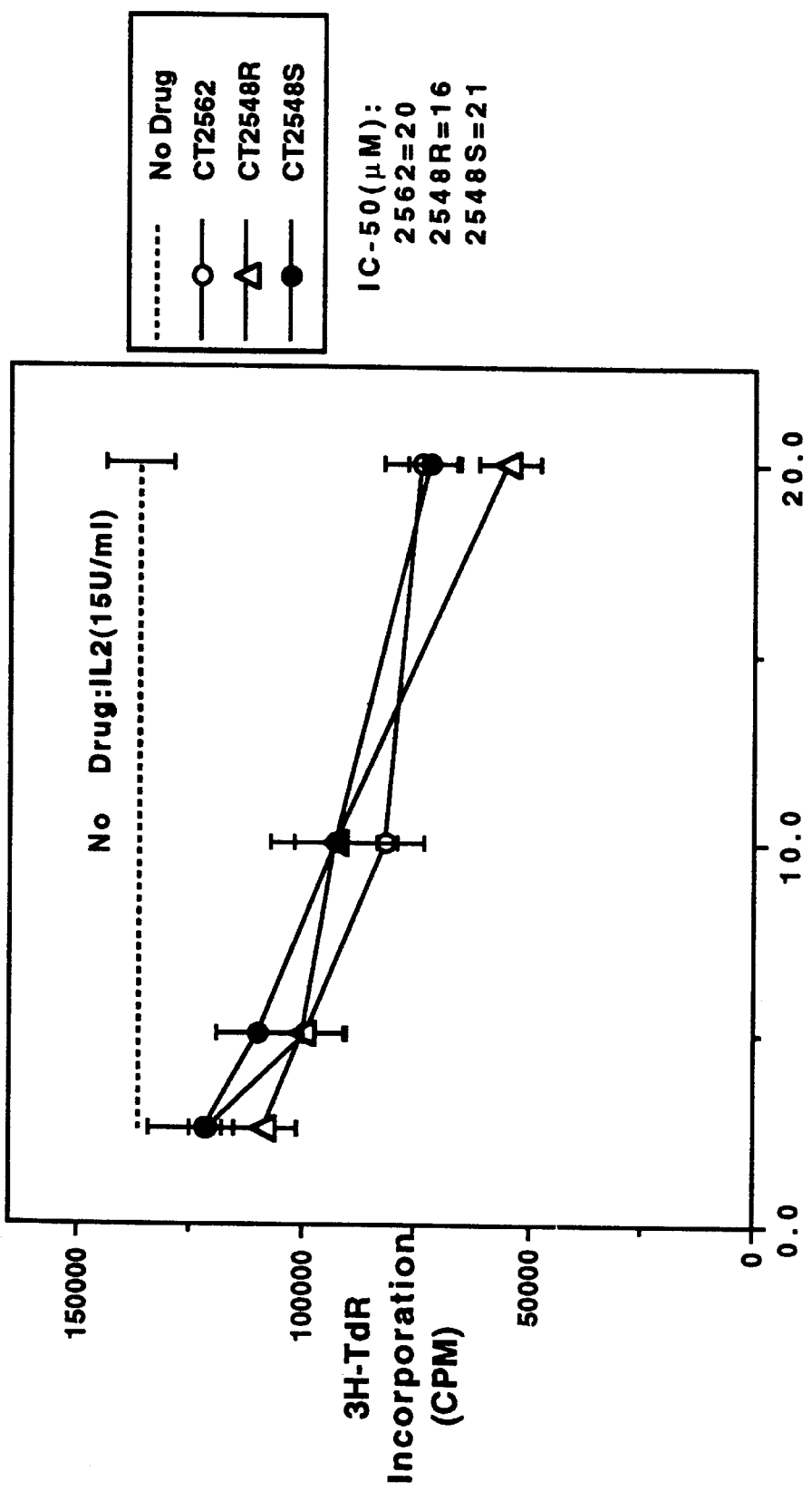

This example illustrates dose response curves used to generate 50% inhibition concentrations (IC50) for inventive compounds nos. 1410, 1439, 1541, 1553, 1553S, 1560, 1565, 2548R, 2548S and 2562 in a murine thymocyte proliferation assay, co-stimulated by Concanavalin A (ConA) and interleukin-2 alpha (IL-2). ConA, used to activate the T-cell receptor (TCR), along with IL-2 co-stimulation, induces T-cell proliferation and differentiation. Thymuses, obtained from normal, female Balb/C mice, were dissociated and plated into 96-well plates at a density of $2 \times 10^5$ cells/well. ConA (0.25 mg/ml) and IL-2 (15 U/ml) were added to the wells. The cells were incubated for 4 days at 37° C. On day 4, the cells were pulsed with tritiated thymidine and incubated for an additional 4 hours. The amount of tritiated thymidine incorporated by the harvested cells was determined in a liquid scintillation counter. Doses of inventive compounds (shown in FIGS. 7A–7E) were added two hours prior to ConA and IL-2 activation. Background counts were less than 200 cpm. Results obtained, illustrate the ability of the inventive compounds to inhibit thymocyte proliferation and activation. In FIG. 7A, inventive compounds nos. 1410 and 1808 inhibit thymocyte proliferation, with an experimental IC50 of 68 or 99 μM, respectively. FIG. 7B presents additional data for compound no. 1410 and 1553S in this assay. Again, both inventive compounds inhibit thymocyte proliferation and have experimental IC50 values of 62 and 46 μM, respectively. FIG. 7C reports assay results for inventive compounds nos. 1439, 1541, 1560 and 1565. All compounds exhibit inhibitive effects on thymocyte proliferation with observed IC50 values of <25, 70, 22 and 32 μM, respectively. FIGS. 7D and 7E illustrate assay results for inventive compounds nos. 1541, 1553, 1560 and 1565 (FIG. 7D) and 2562, 2584R and 2584S (FIG. 7E). As is true of other inventive compounds tested, all these compounds represented in FIGS. 7D and 7E inhibit thymocyte proliferation. Reported IC50 values for the inventive compounds show more potent inhibitive characteristics when compared with inventive compounds previously tested in this assay. Reported IC50 values are 57, 29, 14, 30, 20, 16 and 21 for compounds nos. 1541, 1553, 1560, 1565, 2562, 2548R and 2548S, respectively.

EXAMPLE 58

This example illustrates inhibitive effects of the inventive compounds on Balb/3T3 cell proliferation in response to PDGF stimulation.

Balb/3T3 cells respond vigorously to PDGF stimulation, and are useful in vitro models for further study of PDGF-induced proliferation. Disregulated PDGF-proliferative response has been linked to a variety of diseases, including, e.g., restenosis, atherosclerosis, fibrosis, and tumor cell angiogenesis. In an assay, useful in predicting therapeutic activity for preventing or treating restenosis, atherosclerosis and coronary artery disease, research indicates that the inventive compounds possess inhibitory effects on PDGF-induced proliferation of Balb/3T3 cells.

Balb/3T3 cells were maintained in exponential growth. The cells were removed from a flask with EDTA and plated into 96 well plates at 3000 cells/well. After 48 hours, the media was removed, the cells washed once with PBS and serum free media and the cultures allowed to rest for a 24 hour period. Inventive compounds were added to the wells containing media and Balb/3T3 cells one hour prior to incubation with PDGF/BB, added at constant 10 μM concentrations along with 1 μ Ci 3-H-thymidine dye. Cells were subsequently incubated for 18–24 hours, harvested, and incorporated thymidine assessed on a Packard Topcount to determine degree of cell proliferation. Data obtained in this assay was used to determine experimental 50% inhibition concentrations for the inventive compounds tested.

In conjuction with the Balb/3T3 proliferation assay conducted above, a Balb/3T3 cytotoxicity assay was conducted to determine that the inhibition on proliferation was not due to cytotoxic effects. This assay is similar to the assay decribed above except tritiated thymidine was not added and after 18–24 hours incubation with PDGF/BB and a 10uM solution of 2,7-bis-(2-carboxyethyl)-5(and-6) carboxyflouresceinacetoxymethyl ester (BCECF-AM) was added for 30 minutes at 37° C. (BCECF is a compound that when cleaved by esterases, yields a fluorescent product in viable cells only, therefore providing a measure of viable cell numbers). Following sufficient incubation, BCECF is replaced with PBS and the plate examined with flourescence in a Millipore "cytofluor." The data is compiled and plotted.

Figure 8A:
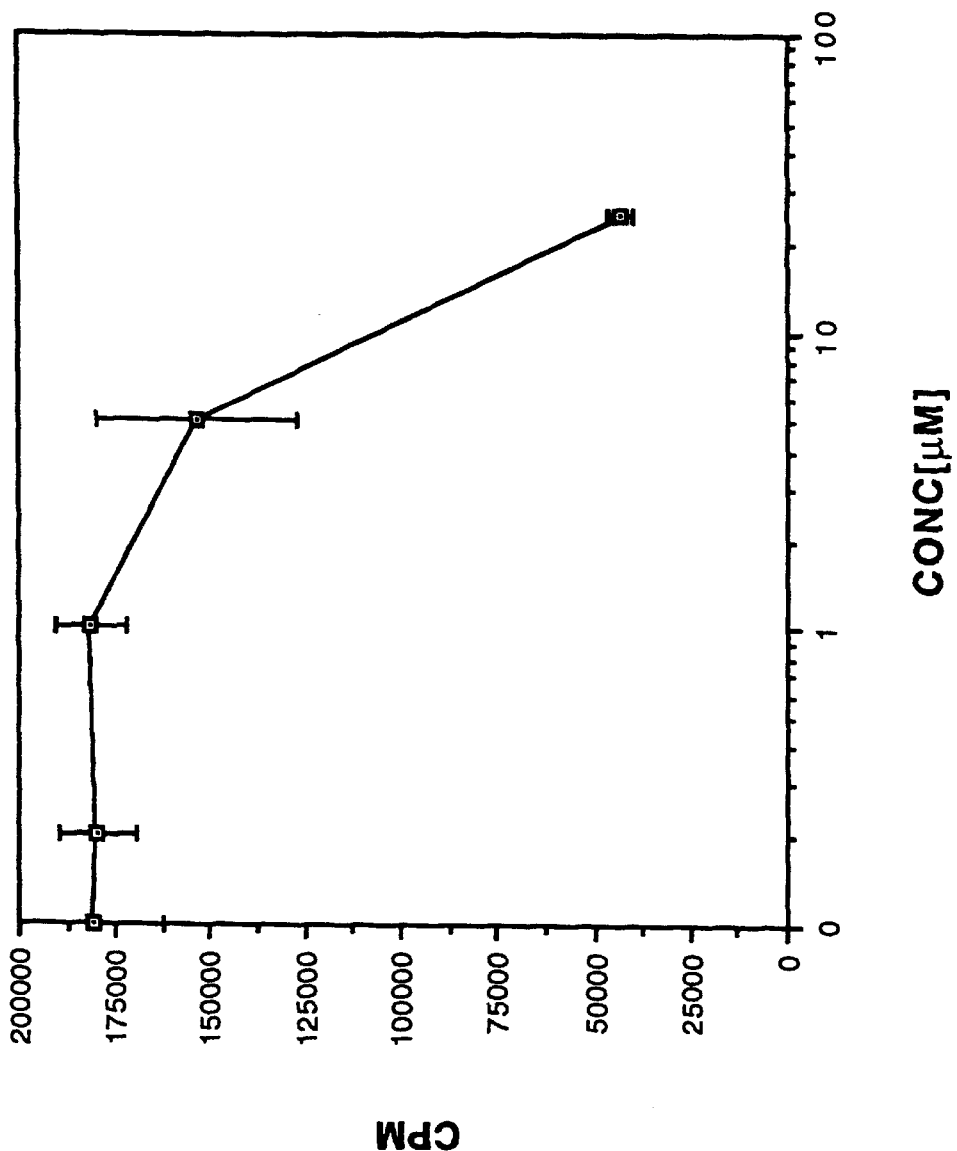
Figure 8B:
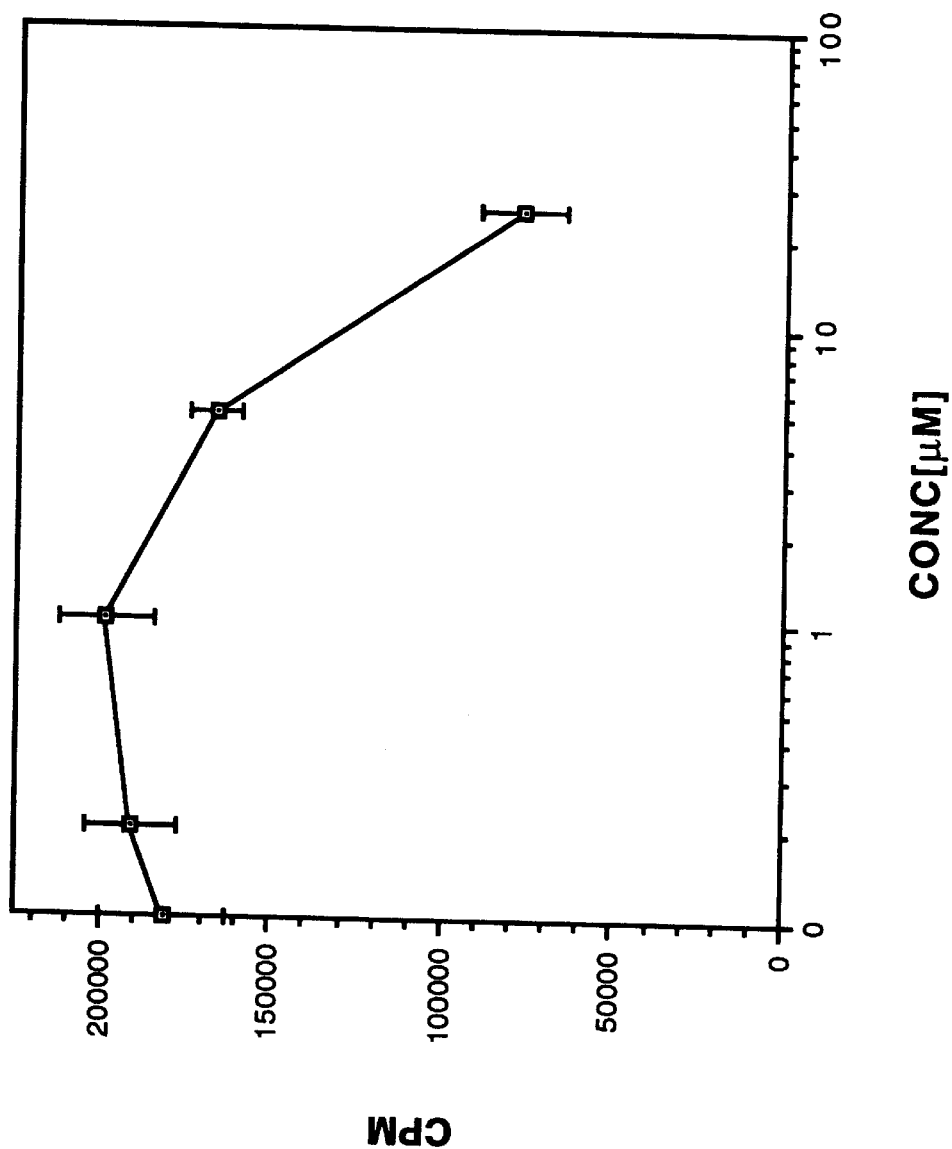
Figure 8C:
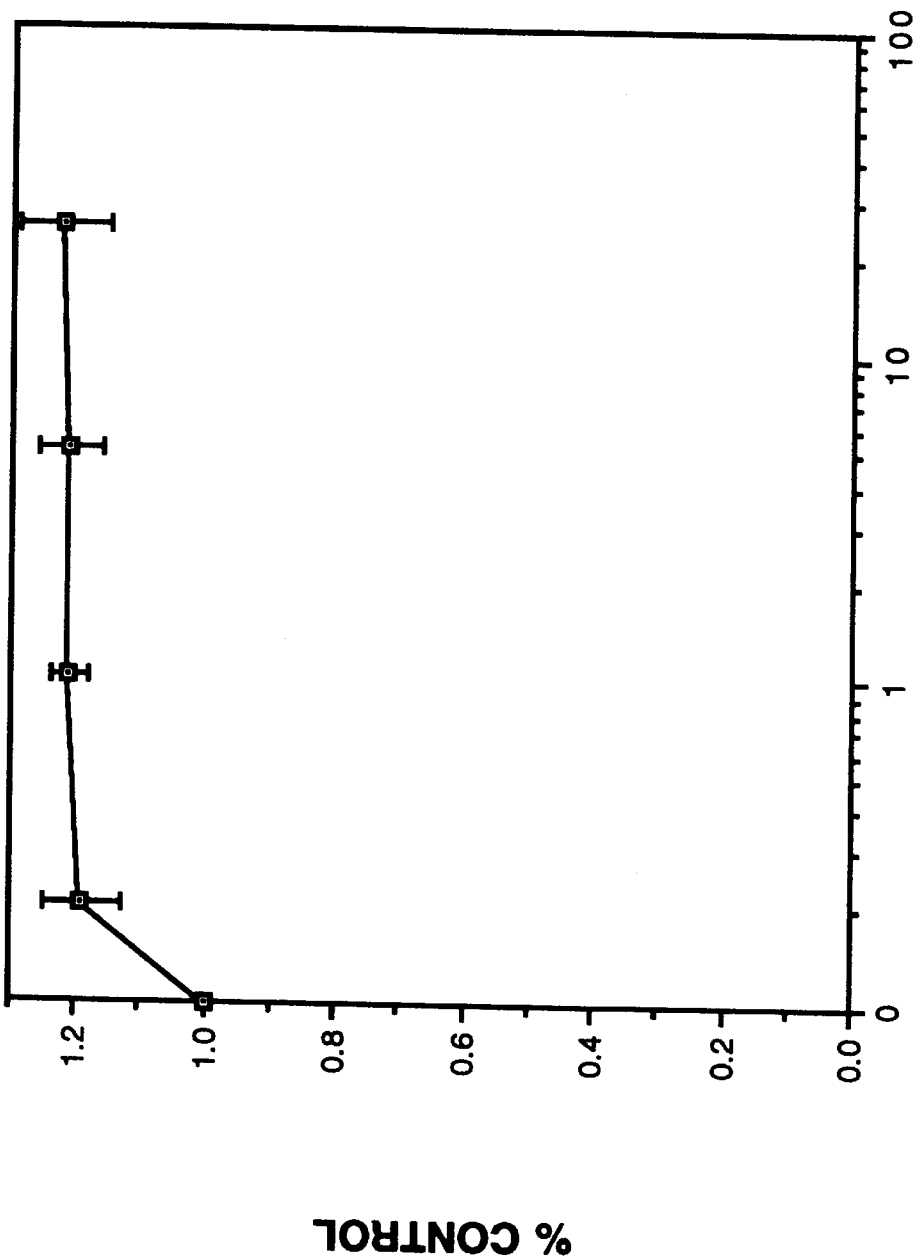
Figure 8D:
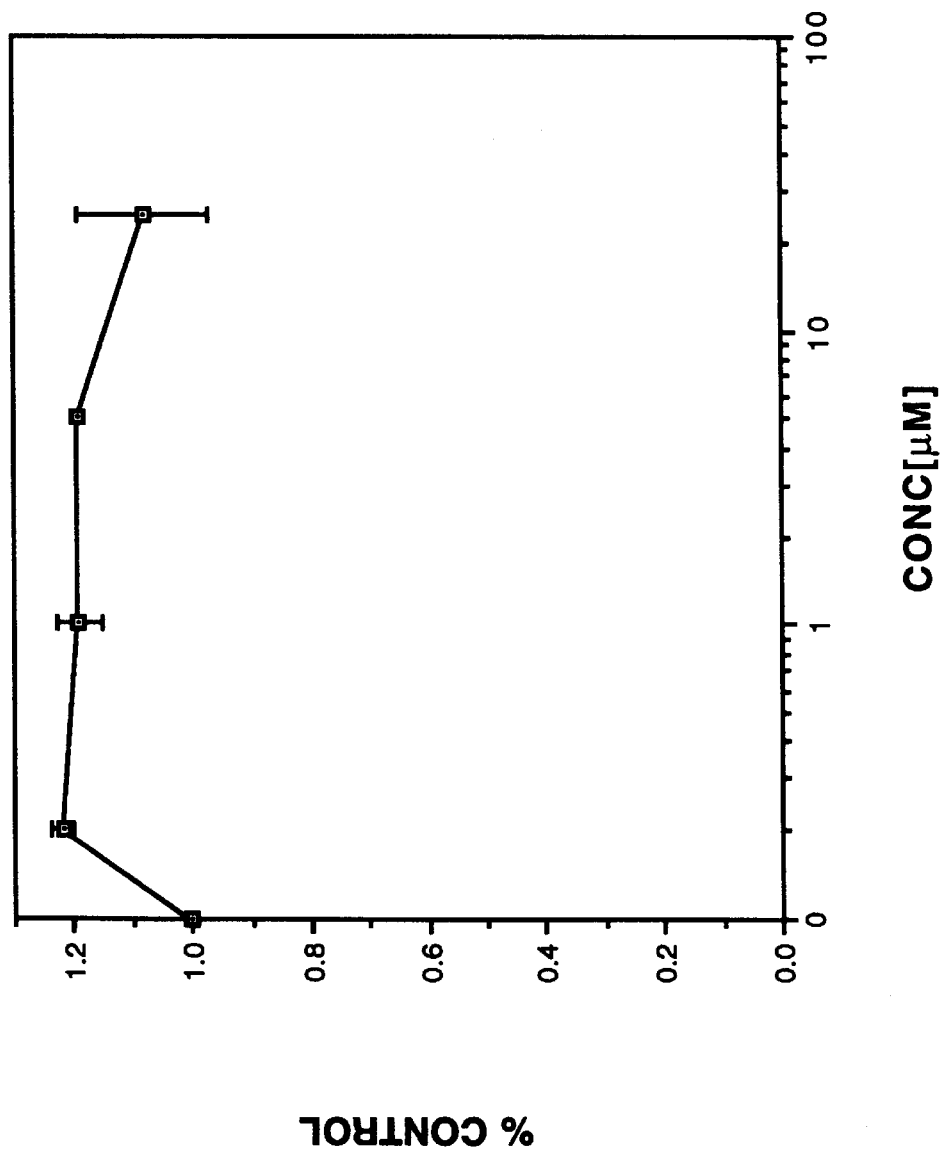

FIGS. 8A–8D report results for inventive compounds nos. 1409 and 1560 in the above proliferation and cytotoxicity assays. The inventive compounds tested inhibit Balb/3T3 proliferation without exhibiting cytotoxic effects. Specifically, FIGS. 8A (1409) and 8B (1560) illustrate proliferative inhibition at various concentration of inventive compound. FIGS. 8C and 8D confirm that the inhibitive effects exhibited at the concentrations tested do not result from any cytotoxic effects of the compounds tested.

EXAMPLE 59

Human umbilical vein endothelial cells (HUVEC) were plated at 4000 cells/well two days prior to conducting an adhesion assay used to determine the effect of various inventive compounds on adherence of cancerous cells to TNF-stimulated HUVECs. After two days, the HUVECs were stimulated with TNF (20 ng/ml) overnight. Specific cancerous cells chosen from among: Jurkat (a human, acute T-cell leukemia cell line); Ramos (a human Burkitt lymphoma cell line); HT-29 (a human adenocarcinoma cell line—of colon origin); NCI-H460 (a human large cell carcinoma cell line—of lung origin); and THP-1 (a human acute monocytic leukemia cell line) were prestained with BCECF and added at 250,000 per well in RPMI containing 1% fetal calf serum. The cells are allowed to adhere for 20 minutes at 37° C., after which time, the plate is inverted and spun at 800 rpm. The wells are washed once with PBS and resuspended in 100 μl PBS prior to reading fluorescence on a Millipore fluorescence plate reader. Data is recorded as percent adherence (Jurkat, Ramos, HT-29, NCI-H460 or THP-1 cells to HUVECs) at selected concentrations of inventive compounds nos. 1587 and/or 3524.

FIGS. 9A, 9B, 9C and 9D report data for inventive compound no. 3524 obtained in this TNF adherence assay using the Jurkat, Ramos, HT-29 and NCI-H460 cell lines, respectively. As shown in these four figures, the compound tested reduces the percentage of Jurkat, Ramos, HT-29 or NCI-H460 cells which adhere to the HUVECs, with generally significant inhibition in adherence at 0.1 to 1.0 μM concentrations of compound.

FIGS. 9E and 9F report data for inventive compounds nos. 1587 and 3524 in reducing percent adherence of THP-1 cells to HUVECs in this assay. Again, significant reductions were observed at approximately 0.1 μM.

In an almost identical assay protocol to that described in this example, HUVECs were similarly stimulated with IL-1β instead of THF. HUVECs were stimulated with IL-1β (10 ng/ml), both in the absence and presence of varying concentrations of drugs for 8 hours in a 96-well microtiter plate. In the wellplate, human monocytic leukemia cell line THP-1 cells were added at 50,000 cells per well. The THP-1 cells were pre-incubated with BCECF, a fluorescence dye that can be used to measure cell number using a fluorescence plate reader. After 10 minutes at 37° C., the microtiter plate was inverted and spun at 900 rpm. The remaining adhering THP-1 cells were then analyzed.

The effect of representative inventive compounds on adherence of THP-1 cells to the IL-1β-stimulated HUVECs was measured as percentage adherence. FIGS. 9G and 9H report data obtained in this modified adherence assay. As shown in the plotted experimental results, both inventive compounds nos. 1587 and 3524 reduce percent adherence of THP-1 cells to stimulated HUVECs, the degree of percent decrease in adherence increasing at higher concentrations of compound. In all experimental trials in these assays, all compounds tested exhibited a significant reduction in adherence of the respective cells to the stimulated HUVEC cells at concentrations generally between 0.1 and 1.0 μM, suggesting potential uses for the inventive compounds in treating cancers of various origins.

EXAMPLE 60

This example was used to investigate inhibition of vascular cell adhesion molecule (VCAM) expression on HUVEC by compound no. 3524. VCAM expression by endothelial cells is an early event in atherogenesis and multiple sclerosis, among other various autoimmune diseases. In the absence of TNF, VCAM expression on HUVEC is at a very low level. HUVECs stimulated with TNF exhibit approximately a 10-fold increase in VCAM expression. In the presence of inventive compound no. 3524, VCAM expression (measured as percent expression) decreased with increasing concentrations of compound. FIG. 10 illustrates results obtained in this assay. The results shown indicate an effectiveness of the inventive compounds in inhibiting VCAM expression in stimulated cells.

EXAMPLE 61

This example illustrates inhibitive effects of compounds nos. 1439, 1553S, 1560 and 1565 on murine splenocyte proliferation co-stimulated by anti-mu (10 mg/ml) and interleukin-4 (IL-4, 12.5 ng/ml). This in vitro assay, described above, is indicative of immune-suppressive/autoimmune treatment assay emphasizing humoral or B cell immune response. This assays are a predictive model for treatment or prevention of autoimmune diseases, such as diabetes, lupus, arthritis, and the like. The assay measures immunosuppressive activity of a drug at the B cell level. Spleens from adult mice contain immature B cells that express surface IgM. Cross-linking the surface IgM with an anti-mu antibody results in B cell proliferation. Additionally, this activation results in an increased expression of interleukin-4 receptors(IL-4R) on the surface of such cells. IL-4 acts as a growth factor for B cells and will increase the amount of proliferation induced by anti-mu.

A mixture of anti-mu and murine IL-4 is added to murine splenocytes to cause their proliferation. Mice spleens are obtained from adult mice and a single cell suspension is prepared in RPMI 1640 medium supplemented with 10% FCS. Cells (200,000) are plated into flat-bottomed wells and pre-incubated for 1–2 hours with various concentrations of inventive compound or PBS if it is a control. A mixture of anti-mu and murine is added to the wells at a final concentration of 5 $\mu$g/ml anti-mu and 12.5 ng/ml IL-4 and plates are incubated for three days. Proliferation is determined on the third day with a pulse of tritiated thymidine. The IC50 concentration of a particular drug is the concentration of drug that results in a 50% inhibition of the proliferation obtained from the positive control.

Results for the assay, shown in FIG. 11 illustrate the inhibitive effect of the inventive compounds tested on anti-mu/IL-4-induced proliferation in a dose response manner. IC50 values for compounds nos. 1439, 1553S, 1560 and 1565 were 31, 50, 29 and 40 $\mu$M, respectively. Background counts were less than 200 cpm.

EXAMPLE 62

This example illustrates an inhibitive effect of compound no. 1206 in a mixed lymphocyte reaction (MLR). This MNR is used to screen potentially immunosuppressive drugs. Lymphocytes ($2 \times 10^5$) from normal human donors are grown for 6 days in the presence and absence (control) of inventive compound no. 1206. Tritiated thymidine is added and the lymphocytes grown for a final 6 hours. Incorporation of the tritiated thymidine occurs when the cells are in cell cycle. Thus, differences in scintillation counts provide evidence that the inventive compounds tested exhibit proliferative inhibition characteristics. The results at various concentrations of inventive compounds are shown in FIG. 12. An experimentally determined IC50 value for compound no. 1206 is 70 $\mu$M.

EXAMPLE 63

This example illustrates effects of the inventive compounds on ovalbumin-induced proliferation in murine lymph cells. Lymphnode cells contain a mixture of lymphoid cells: T-cells, B-cells and macrophages. Although proliferating cells in this assay are T-cells, the response obtained depends on type of antigen-presenting cell (e.g., macrophages) as well as elaboration of various immunoregulatory cytokines. Thus, this assay serves as a good model for T-cell mediated responses and as a valuable screening tool in identifying compounds useful in immunosuppressive therapeutic applications.

Murine T-cells proliferate in vitro in response to a soluble protein antigen if first primed with a corresponding antigen in vivo. This in vivo priming usually involves emulsifying the antigen in complete Freunds adjuvant and injecting this preparation into an appropriate site on a mouse. In this assay the antigen employed was chicken ovalbumin(OVA). Following emulsification in Freund's complete adjuvant, 50 $\mu$g of OVA were injected into both hind footpads of adult Balb/C mice. Fourteen days later the draining lymph nodes (popliteal) were removed and a single cell suspension was prepared in RPMI-1640 (10%FCS) medium. Two hundred thousand lymph node cells are then plated into wells of flat-bottom 96-well plates. Inventive compouds nos. 1410, 1553 (racemic), 1553(S), 1560 and 1565 were added to appropriate wells at various concentrations. OVA, at a final concentration of 200 $\mu$g/ml, was added to appropriate wells. Positive and negative controls were established on each plate, all assay variables being set up in quadruplicate.

The plates were incubated in a humidified, 5% $CO_2$ incubator for 5 days. On the fifth day, 1 $\mu$Ci of tritiated thymidine was added to each well and the plates were incubated for an additional 4 hours. The plates were harvested and the incorporation of 3H-TdR was determined in a liquid scintillation counter. The CPM data was then used to calculate experimental IC50 values for the compounds tested. Again, IC50 is defined as that concentration of compound resulting in 50% inhibition of 3H-TdR incorporation of the positive control.

FIG. 13 reports results obtained for compounds nos. 1410, 1553 (racemic), 1553(S), 1560 and 1565, indicating experimental IC50 values of 55, 45, 43, 34 and 38 $\mu$M, respectively. All compounds exhibit inhibitive characteristics in this assay, suggesting activity as immunosuppressive, therapeutic compounds.

EXAMPLE 64

This example illustrates inhibitive effects of the inventive compounds on LPS-induced TNF release. Data collected is reported as percent inhibition of LPS induced TNF release in whole human blood as compared with control values of TNF release.

In this assay, whole blood was collected from a healthy human donor into Vacutainer tubes containing ACD citrate anti-coagulant. Compounds to be tested were diluted in RPMI medium and added (5 $\mu$l) to tubes containing whole blood (225 $\mu$l). The tubes were mixed and incubated for a maximum of 1 hour at 37° C. LPS *Salmonella abortus* equi was diluted in RPMI and added to samples at 20 $\mu$l per tube (10 ng/ml final concentration). The prepared tubes were mixed and incubated for 4–6 hours at 37° C. The reaction was terminated by adding 750 $\mu$l of RPMI to each tube, then centrifuged to remove cells. Supernatants are collected and stored overnight at 4° C. Supernatant samples are assayed for TNF release using commercial immunoassay kits.

FIG. 14 reports data obtained in this assay for compounds nos. 2518, 1541 and 2548S. Plotted data represent percent inhibition of the maximal response such as, for example, TNF-α levels in the supernatants of LPS-stimulated cells. These stimulated values ranged between 500–1200 pg/mL, depending on experimental parameters and specific blood donor. At 50 μM, inventive compounds 2518, 2541 and 2548 inhibit THF-α induction by 35, 25 or 38% respectively.

We claim:

1. A compound, including enantiomers, diastereomers, salts, solvates, hydrates and mixtures thereof, having the formula I:

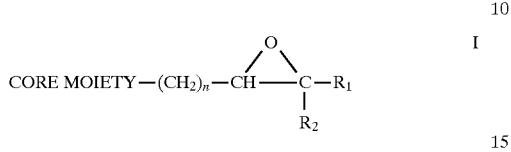

wherein the core moiety is a monocyclic ring structure having five to six ring atoms and two nitrogen atoms at the 1 and 3 positions, n is an integer from 4 to 16, $R_1$ and $R_2$ are a hydrogen or halogen atom, or substituted or unsubstituted $C_{1-12}$ alkyl or alkenyl, and $(CH_2)_n$ is optionally substituted by a hydroxyl, halogen, oxygen, a $C_{1-4}$ alkyl group or a dimethylamino group.

2. The compound according to claim 1, wherein the integer is not greater than 12.

3. The compound according to claim 1, wherein the integer is not greater than 10.

4. The compound according to claim 1, wherein the alkyl or alkenyl groups is substituted by a hydroxyl or $C_{1-4}$ alkyl group, halogen atom or dimethylamino group or interrupted by an oxygen atom.

5. The compound according to claim 4, wherein the halogen is selected from the group consisting of bromine, chlorine, fluorine and iodine.

6. The compound according to claim 1, wherein the core moiety is a member selected from the group consisting of: substituted or unsubstituted pyrimidinyl; thyminyl; and uracilyl.

7. The compound according to claim 1, wherein the core moiety is selected from the group consisting of: orotic acid; methyldihydroxypyrazolopyrimidinyl; methylpyrrolopyrimidinyl; dihydrothyminyl; alkyl-substituted ($C_{1-6}$) thyminyl; methylthyminyl; alkyl-substituted ($C_{1-6}$) uracil; 6-aminouracil; 1-methyldihydrouracil; 1-methyluracil; 5- and 6-position substituted uracils; and 5-bromouracil.

8. A pharmaceutical composition comprising atheraputically effective amount of a compound of claim 1 in admixture with a pharmaceutically acceptable excipient or carrier.

9. A compound selected from the group consisting of:

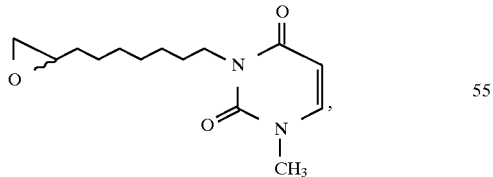

-continued

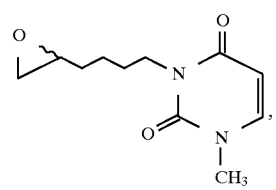

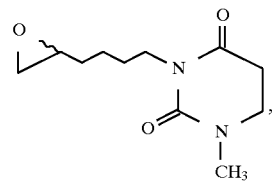

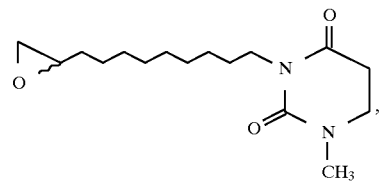

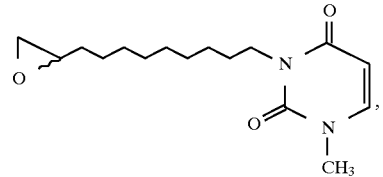

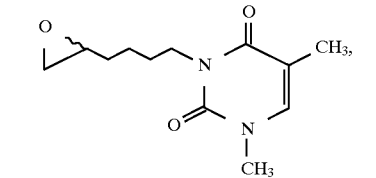

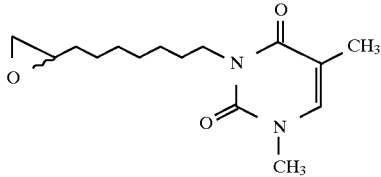

and

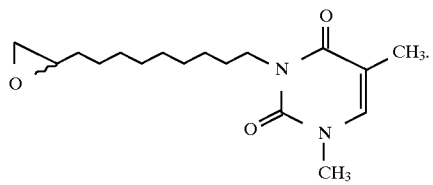

* * * * *

UNITED STATES PATENT AND TRADEMARK OFFICE
CERTIFICATE OF CORRECTION

PATENT NO. : 5,866,576
DATED : February 2, 1999
INVENTOR(S) : Underiner et al.

It is certified that error appears in the above-identified patent and that said Letters Patent is hereby corrected as shown below:

In the Claims:

Claim 4, Line 30, delete "groups" and insert --group--.

Claim 8, Line 47, delete "atheraputically" and insert --a therapeutically--.

Signed and Sealed this

Eighth Day of June, 1999

Attest:

Q. TODD DICKINSON

Attesting Officer

Acting Commissioner of Patents and Trademarks